US010077444B2

(12) United States Patent
Fitzgerald et al.

(10) Patent No.: US 10,077,444 B2
(45) Date of Patent: Sep. 18, 2018

(54) COMPOSITIONS AND METHODS FOR INHIBITING EXPRESSION OF THE LECT2 GENE

(71) Applicant: ALNYLAM PHARMACEUTICALS, INC., Cambridge, MA (US)

(72) Inventors: Kevin Fitzgerald, Brookline, MA (US); Alfica Sehgal, Medford, MA (US); Brian Bettencourt, Groton, MA (US); Gregory Hinkle, Plymouth, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/026,897

(22) PCT Filed: Oct. 1, 2014

(86) PCT No.: PCT/US2014/058624
§ 371 (c)(1),
(2) Date: Apr. 1, 2016

(87) PCT Pub. No.: WO2015/050990
PCT Pub. Date: Apr. 9, 2015

(65) Prior Publication Data
US 2016/0264966 A1    Sep. 15, 2016

Related U.S. Application Data

(60) Provisional application No. 62/035,819, filed on Aug. 11, 2014, provisional application No. 61/885,693, filed on Oct. 2, 2013.

(51) Int. Cl.
| C12N 15/11 | (2006.01) |
| C12N 15/113 | (2010.01) |
| C07H 21/02 | (2006.01) |
| A61K 31/712 | (2006.01) |
| A61K 31/7125 | (2006.01) |

(52) U.S. Cl.
CPC ........ *C12N 15/113* (2013.01); *C12N 15/1136* (2013.01); *C12N 2310/14* (2013.01); *C12N 2310/315* (2013.01); *C12N 2310/321* (2013.01); *C12N 2310/322* (2013.01); *C12N 2310/351* (2013.01); *C12N 2310/3515* (2013.01); *C12N 2310/3533* (2013.01)

(58) Field of Classification Search
None
See application file for complete search history.

(56) References Cited

U.S. PATENT DOCUMENTS

| 8,106,022 B2 * | 1/2012 | Manoharan ...... A61K 47/48092 514/25 |
| 2002/0086356 A1* | 7/2002 | Tuschl ..................... C12Q 1/66 435/69.1 |
| 2005/0246794 A1* | 11/2005 | Khvorova ............ A61K 31/713 800/286 |
| 2005/0255487 A1* | 11/2005 | Khvorova ............ A61K 31/713 435/6.11 |
| 2010/0120893 A1* | 5/2010 | Sah ........................ C12N 15/111 514/44 A |
| 2014/0343123 A1* | 11/2014 | Prakash ............... C12N 15/113 514/44 A |

FOREIGN PATENT DOCUMENTS

| CN | 102552882 A | | 7/2012 |
| WO | WO 2010/006342 | * | 1/2010 |
| WO | 2011076095 A1 | | 6/2011 |
| WO | 2012009567 A2 | | 1/2012 |
| WO | 2012135246 A2 | | 10/2012 |
| WO | 2013075035 A1 | | 5/2013 |
| WO | 2015050990 A1 | | 4/2015 |
| WO | 2016164746 A1 | | 10/2016 |

OTHER PUBLICATIONS

"Poster Session 4: HCV: Virology, Pathogenesis, and Immunology" Hepatology (2014) vol. 60, pp. 1048A-1087A.
International Search Report and Written Opinion for International Application No. PCT/US2016/026676 dated Jul. 12, 2016.
Wu et al. "The Roles of Leukocyte Cell-Derived Chemotaxin 2 Gene in Hepatocellular Carcinoma Invasion and Angiogenesis" Proceedings of the American Association for Cancer Research Annual Meeting (2008) pp. 1-35.
Benson et al., "Leukocyte Chemotactic Factor 2: A Novel Renal Amyloid Protein", Kidney International, vol. 74, No. 2, Apr. 30, 2008, pp. 218-222.
Benson, Merrill D., "LECT2 Amyloidosis", Kidney International, vol. 77, No. 9, May 1, 2010, pp. 757-759.
International Search Report and Written Opinion in International Application No. PCT/US2014/058624 dated Jan. 13, 2015.
Larsen et al., "Prevalence and Morphology of Leukocyte Chemotactic Factor 2-Associated Amyloid in Renal Biopsies", Kidney International, vol. 77, No. 9, Feb. 24, 2010, pp. 816-819.
Yamagoe et al., "Molecular Cloning of Human and Bovine LECT2 Having a Neutrophil Chemotactic Activity and Its Specific Expression in the Live", Biochimica Et Biophysica Acta, Elsevier, NL, vol. 1396, No. 1, Mar. 4, 1998, pp. 105-113.

* cited by examiner

*Primary Examiner* — Richard A Schnizer
(74) *Attorney, Agent, or Firm* — Lando & Anastasi, LLP

(57) ABSTRACT

The invention relates to double-stranded ribonucleic acid (dsRNA) compositions targeting the LECT2 gene, and methods of using such dsRNA compositions to alter (e.g., inhibit) expression of LECT2.

71 Claims, 1 Drawing Sheet
Specification includes a Sequence Listing.

```
   1 aaatcaaata gctatccatg gaatattaga acttgacttg ctccatcctc ttaaacttt
  61 tgtgtctcac actaaagaaa tgagagatgc agaattctaa ggctaaatag ctaggaagta
 121 ttcattcaaa cttgaatatt cttcaaagag agtgtggggg caactctaat cagaggaaga
 181 aactaaagga agtaaaacca gatgttttcc accaaagccc tccttttggc tggtctgatt
 241 tctaccgcac tggcagggcc atgggctaat atatgtgctg gcaagtcttc caatgagatc
 301 cggacgtgtg accgccatgg ctgtggacag tactctgctc aaagaagtca gaggcctcac
 361 cagggtgtgg acatcttgtg ctctgctgga tctactgtgt acgcaccatt cactggaatg
 421 attgtgggcc aggagaaacc ttatcaaaac aagaatgcta tcaataatgg tgttcgaata
 481 tctggaagag gtttttgtgt caaaatgttc tacattaagc caattaagta taaaggtcct
 541 attaagaagg gagaaaaact tggaactcta ttgcccttgc agaaagttta tcctggcata
 601 caatcgcatg tgcacattga aaactgtgac tcgagtgacc ctactgcata cctgtaaatc
 661 gaaggccaat ggtcagatct tcaaaataaa aagtcatctt aaaaacctgg atgcataccc
 721 ttctcttcaa gaaatttgtg ttcacaaagg aaaaatgcat gaagggatgg atacccatt
 781 ttccatgaca tgattattac acattgcatg cctgtatcaa aacatctcac gtacctcata
 841 aacatataca cctatgtacc cacaaaaatt ttttaattaa aaaaggaaa tttgagttta
 901 aatagaaaca tgataaatgc aagaaagaaa acattttgat tttaactcat tgtcactctg
 961 atgttcatgt gaactggttg cttcgggctc tttgatctgt cacctatgga atctgagtgg
1021 tttttattttt tagatttctc agtcccaaag atctaagata aataaacaag agaactt
```

SEQ ID NO:1

SEQUENCE LISTING

<160> NUMBER OF SEQ ID NOS: 1053

<210> SEQ ID NO 1
<211> LENGTH: 1077
<212> TYPE: DNA
<213> ORGANISM: Homo sapiens

<400> SEQUENCE: 1

| aaatcaaata gctatccatg gaatattaga acttgacttg ctccatcctc ttaaactttt | 60 |
| tgtgtctcac actaaagaaa tgagagatgc agaattctaa ggctaaatag ctaggaagta | 120 |
| ttcattcaaa cttgaatatt cttcaaagag agtgtggggg caactctaat cagaggaaga | 180 |
| aactaaagga agtaaaacca gatgttttcc accaaagccc tccttttggc tggtctgatt | 240 |
| tctaccgcac tggcagggcc atgggctaat atatgtgctg gcaagtcttc caatgagatc | 300 |
| cggacgtgtg accgccatgg ctgtggacag tactctgctc aaagaagtca gaggcctcac | 360 |
| cagggtgtgg acatcttgtg ctctgctgga tctactgtgt acgcaccatt cactggaatg | 420 |
| attgtgggcc aggagaaacc ttatcaaaac aagaatgcta tcaataatgg tgttcgaata | 480 |
| tctggaagag gtttttgtgt caaaatgttc tacattaagc caattaagta taaaggtcct | 540 |
| attaagaagg gagaaaaact tggaactcta ttgcccttgc agaaagttta tcctggcata | 600 |
| caatcgcatg tgcacattga aactgtgac tcgagtgacc ctactgcata cctgtaaatc | 660 |
| gaaggccaat ggtcagatct tcaaaataaa aagtcatctt aaaaacctgg atgcataccc | 720 |
| ttctcttcaa gaaatttgtg ttcacaaagg aaaaatgcat gaagggatgg atacccccatt | 780 |
| ttccatgaca tgattattac acattgcatg cctgtatcaa aacatctcac gtacctcata | 840 |
| aacatataca cctatgtacc cacaaaaatt ttttaattaa aaaaaggaaa tttgagttta | 900 |
| aatagaaaca tgataaatgc aagaaagaaa acattttgat tttaactcat tgtcactctg | 960 |
| atgttcatgt gaactggttg cttcgggctc tttgatctgt cacctatgga atctgagtgg | 1020 |
| ttttattttt tagatttctc agtcccaaag atctaagata aataaacaag agaactt | 1077 |

<210> SEQ ID NO 2
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
aaaucaaaua gcuauccau                                                  19

<210> SEQ ID NO 3
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
auggauagcu auuugauuu                                                  19

<210> SEQ ID NO 4
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 4
aauagcuauc cauggaaua                                                      19

<210> SEQ ID NO 5
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
uauuccaugg auagcuauu                                                      19

<210> SEQ ID NO 6
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
uauccaugga auauuagaa                                                      19

<210> SEQ ID NO 7
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
uucuaauauu ccauggaua                                                      19

<210> SEQ ID NO 8
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
auggaauauu agaacuuga                                                      19

<210> SEQ ID NO 9
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ucaaguucua auauuccau                                                      19
```

```
<210> SEQ ID NO 10
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gaauauuaga acugacuu                                                  19

<210> SEQ ID NO 11
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
aagucaaguu cuaauauuc                                                 19

<210> SEQ ID NO 12
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agaacuugac uugcuccau                                                 19

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
auggagcaag ucaaguucu                                                 19

<210> SEQ ID NO 14
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gaacuugacu ugcuccauc                                                 19

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 15
gauggagcaa gucaaguuc                                                  19

<210> SEQ ID NO 16
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ugacuugcuc cauccucuu                                                  19

<210> SEQ ID NO 17
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
aagaggaugg agcaaguca                                                  19

<210> SEQ ID NO 18
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
ccauccucuu aaacuuuuu                                                  19

<210> SEQ ID NO 19
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
aaaaaguuua agaggaugg                                                  19

<210> SEQ ID NO 20
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ccucuuaaac uuuuugugu                                                  19

<210> SEQ ID NO 21
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
acacaaaaag uuuagagg                                                      19

<210> SEQ ID NO 22
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ucuuaaacuu uuugugucu                                                     19

<210> SEQ ID NO 23
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
agacacaaaa aguuuaaga                                                     19

<210> SEQ ID NO 24
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24 cuuuugugu cucacacua                                                      19

<210> SEQ ID NO 25
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
uagugugaga cacaaaaag                                                     19

<210> SEQ ID NO 26
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gugucucaca cuaaagaaa                                                     19
```

<210> SEQ ID NO 27
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
uuucuuuagu gugagacac                                              19

<210> SEQ ID NO 28
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ucacacuaaa gaaaugaga                                              19

<210> SEQ ID NO 29
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ucucauuucu uuaguguga                                              19

<210> SEQ ID NO 30
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
acacuaaaga aaugagaga                                              19

<210> SEQ ID NO 31
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ucucucauuu cuuuagugu                                              19

<210> SEQ ID NO 32
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 32
agaaaugaga gaugcagaa         19

<210> SEQ ID NO 33
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
uucugcaucu cucauuucu         19

<210> SEQ ID NO 34
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gagagaugca gaauucuaa         19

<210> SEQ ID NO 35
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
uuagaauucu gcaucucuc         19

<210> SEQ ID NO 36
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
augcagaauu cuaaggcua         19

<210> SEQ ID NO 37
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
uagccuuaga auucugcau         19

<210> SEQ ID NO 38
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gaauucuaag gcuaaauag                                              19

<210> SEQ ID NO 39
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
cuauuuagcc uuagaauuc                                              19

<210> SEQ ID NO 40
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
uucuaaggcu aaauagcua                                              19

<210> SEQ ID NO 41
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
uagcuauuua gccuuagaa                                              19

<210> SEQ ID NO 42
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
cuaaauagcu aggaaguau                                              19

<210> SEQ ID NO 43
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
```
auacuuccua gcuauuuag                     19

<210> SEQ ID NO 44
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
auagcuagga aguauucau                     19

<210> SEQ ID NO 45
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
augaauacuu ccuagcuau                     19

<210> SEQ ID NO 46
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
ggaaguauuc auucaaacu                     19

<210> SEQ ID NO 47
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
aguuugaaug aauacuucc                     19

<210> SEQ ID NO 48
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
cauucaaacu ugaauauuc                     19

<210> SEQ ID NO 49
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 49
gaauauucaa guuugaaug                                                    19

<210> SEQ ID NO 50
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
cuugaauauu cuucaaaga                                                    19

<210> SEQ ID NO 51
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
ucuuugaaga auauucaag                                                    19

<210> SEQ ID NO 52
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
cuucaaagag agugugggg                                                    19

<210> SEQ ID NO 53
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
ccccacacuc ucuuugaag                                                    19

<210> SEQ ID NO 54
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
caaagagagu guggggca                                                     19

<210> SEQ ID NO 55
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ugcccccaca cucucuuug                                                      19

<210> SEQ ID NO 56
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56 guguggggc aacucuaau                                                       19

<210> SEQ ID NO 57
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
auuagaguug cccccacac                                                      19

<210> SEQ ID NO 58
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gggggcaacu cuaaucaga                                                      19

<210> SEQ ID NO 59
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
ucugauuaga guugccccc                                                      19

<210> SEQ ID NO 60
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
```
aacucuaauc agaggaaga                                               19

<210> SEQ ID NO 61
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ucuuccucug auuagaguu                                               19

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
aaucagagga agaaacuaa                                               19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
uuaguuucuu ccucugauu                                               19

<210> SEQ ID NO 64
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
aucagaggaa gaaacuaaa                                               19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
uuuaguuucu uccucugau                                               19

<210> SEQ ID NO 66
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 66
agaaacuaaa ggaaguaaa                                                        19

<210> SEQ ID NO 67
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
uuuacuuccu uuaguuucu                                                        19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
gaaacuaaag gaaguaaaa                                                        19

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
uuuuacuucc uuuaguuuc                                                        19

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
uaaaggaagu aaaaccaga                                                        19

<210> SEQ ID NO 71
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
ucugguuuua cuuccuuua                                                        19
```

```
<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
aaguaaaacc agauguuuu                                              19

<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
aaaacaucug guuuuacuu                                              19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
ccagauguuu uccaccaaa                                              19

<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
uuuggtggaa aacaucugg                                              19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
cagauguuuu ccaccaaag                                              19

<210> SEQ ID NO 77
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 77
cuuuggugga aaacaucug                                                  19

<210> SEQ ID NO 78
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
uccaccaaag cccuccuuu                                                  19

<210> SEQ ID NO 79
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
aaaggagggc uuuggugga                                                  19

<210> SEQ ID NO 80
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
ccaccaaagc ccuccuuuu                                                  19

<210> SEQ ID NO 81
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
aaaaggaggg cuuuggugg                                                  19

<210> SEQ ID NO 82
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
cccuccuuuu ggcuggucu                                                  19

<210> SEQ ID NO 83
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 83
agaccagcca aaaggaggg                                                      19

<210> SEQ ID NO 84
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
ggcuggucug auuucuacc                                                      19

<210> SEQ ID NO 85
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
gguagaaauc agaccagcc                                                      19

<210> SEQ ID NO 86
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ggucugauuu cuaccgcac                                                      19

<210> SEQ ID NO 87
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
gugcgguaga aaucagacc                                                      19

<210> SEQ ID NO 88
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
gauuucuacc gcacuggca                                                      19
```

```
<210> SEQ ID NO 89
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ugccagugcg guagaaauc                                                    19

<210> SEQ ID NO 90
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
uaccgcacug gcagggcca                                                    19

<210> SEQ ID NO 91
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
uggcccugcc agugcggua                                                    19

<210> SEQ ID NO 92
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ccgcacuggc agggccaug                                                    19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
cauggcccug ccagugcgg                                                    19

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 94
ggcagggcca ugggcuaau                                                    19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
auuagcccau ggcccugcc                                                    19

<210> SEQ ID NO 96
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
gccaugggcu aauauaugu                                                    19

<210> SEQ ID NO 97
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
acauauauua gcccauggc                                                    19

<210> SEQ ID NO 98
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
ccaugggcua auauaugug                                                    19

<210> SEQ ID NO 99
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
cacauauauu agcccaugg                                                    19

<210> SEQ ID NO 100
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
cuaauauaug ugcuggcaa                                                   19

<210> SEQ ID NO 101
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
uugccagcac auauauuag                                                   19

<210> SEQ ID NO 102
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
auaugugcug gcaagucuu                                                   19

<210> SEQ ID NO 103
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
aagacuugcc agcacauau                                                   19

<210> SEQ ID NO 104
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
cuggcaaguc uuccaauga                                                   19

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
ucauuggaag acuugccag                                                   19
```

<210> SEQ ID NO 106
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106 gcaagcuuc caaugagau                                                    19

<210> SEQ ID NO 107
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
aucucauugg aagacuugc                                                   19

<210> SEQ ID NO 108
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 108
ucuuccaaug agauccgga                                                   19

<210> SEQ ID NO 109
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 109
uccggaucuc auuggaaga                                                   19

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 110
augagauccg gacguguga                                                   19

<210> SEQ ID NO 111
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

```
<210> SEQ ID NO 111
...
Synthetic oligonucleotide"

<400> SEQUENCE: 111
ucacacgucc ggaucucau                                                19

<210> SEQ ID NO 112
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gauccggacg ugugaccgc                                                19

<210> SEQ ID NO 113
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
gcggucacac guccggauc                                                19

<210> SEQ ID NO 114
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
cggacgugug accgccaug                                                19

<210> SEQ ID NO 115
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
cauggcgguc acacguccg                                                19

<210> SEQ ID NO 116
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
acgugugacc gccauggcu                                                19

<210> SEQ ID NO 117
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
agccauggcg gucacacgu                                              19

<210> SEQ ID NO 118
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
ccgccauggc uguggacag                                              19

<210> SEQ ID NO 119
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
cuguccacag ccauggcgg                                              19

<210> SEQ ID NO 120
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ccauggcugu ggacaguac                                              19

<210> SEQ ID NO 121
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
guacugucca cagccaugg                                              19

<210> SEQ ID NO 122
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
```
ggcuguggac aguacucug                                    19

<210> SEQ ID NO 123
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
cagaguacug uccacagcc                                    19

<210> SEQ ID NO 124
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
guacucugcu caaagaagu                                    19

<210> SEQ ID NO 125
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
acuucuuuga gcagaguac                                    19

<210> SEQ ID NO 126
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ucugcucaaa gaagucaga                                    19

<210> SEQ ID NO 127
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
ucugacuucu uugagcaga                                    19

<210> SEQ ID NO 128
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 128
caaagaaguc agaggccuc                                              19

<210> SEQ ID NO 129
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gaggccucug acuucuuug                                              19

<210> SEQ ID NO 130
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
aagucagagg ccucaccag                                              19

<210> SEQ ID NO 131
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
cuggugaggc cucugacuu                                              19

<210> SEQ ID NO 132
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gaggccucac cagggugug                                              19

<210> SEQ ID NO 133
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
cacacccugg ugaggccuc                                              19

<210> SEQ ID NO 134
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gccucaccag gguguggac                                              19

<210> SEQ ID NO 135
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
guccacaccc uggugaggc                                              19

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
ccagggugug gacaucuug                                              19

<210> SEQ ID NO 137
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
caagaugucc acacccugg                                              19

<210> SEQ ID NO 138
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
gguguggaca ucuugugcu                                              19

<210> SEQ ID NO 139
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
```

```
agcacaagau guccacacc                                              19

<210> SEQ ID NO 140
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
acaucuugug cucugcugg                                              19

<210> SEQ ID NO 141
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
ccagcagagc acaagaugu                                              19

<210> SEQ ID NO 142
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
gugcucugcu ggaucuacu                                              19

<210> SEQ ID NO 143
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
aguagaucca gcagagcac                                              19

<210> SEQ ID NO 144
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
cugcuggauc uacugugua                                              19

<210> SEQ ID NO 145
<211> LENGTH: 19
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 145
uacacaguag auccagcag                                                    19

<210> SEQ ID NO 146
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
ggaucuacug uguacgcac                                                    19

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gugcguacac aguagaucc                                                    19

<210> SEQ ID NO 148
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
cuacugugua cgcaccauu                                                    19

<210> SEQ ID NO 149
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
aauggugcgu acacaguag                                                    19

<210> SEQ ID NO 150
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
cuguguacgc accauucac                                                    19
```

```
<210> SEQ ID NO 151
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
gugaauggug cguacacag                                                    19

<210> SEQ ID NO 152
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
gcaccauuca cuggaauga                                                    19

<210> SEQ ID NO 153
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ucauuccagu gaauggugc                                                    19

<210> SEQ ID NO 154
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ccauucacug gaaugauug                                                    19

<210> SEQ ID NO 155
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
caaucauucc agugaaugg                                                    19

<210> SEQ ID NO 156
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 156
cuggaaugau uguggcca                              19

<210> SEQ ID NO 157
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
uggcccacaa ucauuccag                             19

<210> SEQ ID NO 158
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
gaaugauugu gggccagga                             19

<210> SEQ ID NO 159
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
uccuggccca caaucauuc                             19

<210> SEQ ID NO 160
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
gauugugggc caggagaaa                             19

<210> SEQ ID NO 161
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
uuucuccugg cccacaauc                             19

<210> SEQ ID NO 162
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 162
gggccaggag aaaccuuau                                                  19

<210> SEQ ID NO 163
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
auaagguuuc uccuggccc                                                  19

<210> SEQ ID NO 164
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
caggagaaac cuuaucaaa                                                  19

<210> SEQ ID NO 165
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
uuugauaagg uuucuccug                                                  19

<210> SEQ ID NO 166
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
aaaccuuauc aaacaaga                                                   19

<210> SEQ ID NO 167
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167 ucuuguuug auaagguuu                                                   19
```

```
<210> SEQ ID NO 168
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
uaucaaaaca agaaugcua                                                   19

<210> SEQ ID NO 169
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
uagcauucuu guuugaua                                                    19

<210> SEQ ID NO 170
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aacaagaaug cuaucaaua                                                   19

<210> SEQ ID NO 171
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
uauugauagc auucuuguu                                                   19

<210> SEQ ID NO 172
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
caagaaugcu aucaauaau                                                   19

<210> SEQ ID NO 173
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 173
auuauugaua gcauucuug                                          19

<210> SEQ ID NO 174
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
caauaauggu guucgaaua                                          19

<210> SEQ ID NO 175
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
uauucgaaca ccauuauug                                          19

<210> SEQ ID NO 176
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
uaaugguguu cgaauaucu                                          19

<210> SEQ ID NO 177
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
agauauucga acaccauua                                          19

<210> SEQ ID NO 178
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
uguucgaaua ucuggaaga                                          19

<210> SEQ ID NO 179
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
ucuuccagau auucgaaca                                                  19

<210> SEQ ID NO 180
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
auaucuggaa gagguuuuu                                                  19

<210> SEQ ID NO 181
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
aaaaaccucu uccagauau                                                  19

<210> SEQ ID NO 182
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aucuggaaga gguuuuugu                                                  19

<210> SEQ ID NO 183
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
acaaaaaccu cuuccagau                                                  19

<210> SEQ ID NO 184
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
agagguuuuu gugucaaaa                                                  19
```

```
<210> SEQ ID NO 185
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
uuuugacaca aaaccucu                                                    19

<210> SEQ ID NO 186
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gguuuuugug ucaaaaugu                                                   19

<210> SEQ ID NO 187
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
acauuuugac acaaaaacc                                                   19

<210> SEQ ID NO 188
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
gugucaaaau guucuacau                                                   19

<210> SEQ ID NO 189
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
auguagaaca uuuugacac                                                   19

<210> SEQ ID NO 190
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 190
ucaaaauguu cuacauuaa					19

<210> SEQ ID NO 191
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
uuaauguaga acauuuuga					19

<210> SEQ ID NO 192
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
uguucuacau uaagccaau					19

<210> SEQ ID NO 193
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
auuggcuuaa uguagaaca					19

<210> SEQ ID NO 194
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
guauaaaggu ccuauuaag					19

<210> SEQ ID NO 195
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
cuuaauagga ccuuuauac					19

<210> SEQ ID NO 196
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
uauaaagguc cuauuaaga                                                    19

<210> SEQ ID NO 197
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
ucuuaauagg accuuuaua                                                    19

<210> SEQ ID NO 198
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
ccuauuaaga agggagaaa                                                    19

<210> SEQ ID NO 199
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
uuucucccuu cuuaauagg                                                    19

<210> SEQ ID NO 200
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
cuauuaagaa gggagaaaa                                                    19

<210> SEQ ID NO 201
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
```

```
uuuucucccu ucuuaauag                                                    19

<210> SEQ ID NO 202
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aagaagggag aaaaacuug                                                    19

<210> SEQ ID NO 203
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
caaguuuuuc ucccuucuu                                                    19

<210> SEQ ID NO 204
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
agaaaaacuu ggaacucua                                                    19

<210> SEQ ID NO 205
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
uagaguucca aguuuuucu                                                    19

<210> SEQ ID NO 206
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aaaacuugga acucuauug                                                    19

<210> SEQ ID NO 207
<211> LENGTH: 19
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 207
caauagaguu ccaaguuuu                                                   19

<210> SEQ ID NO 208
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
cuuggaacuc uauugcccu                                                   19

<210> SEQ ID NO 209
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
agggcaauag aguccaag                                                    19

<210> SEQ ID NO 210
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
cucuauugcc cuugcagaa                                                   19

<210> SEQ ID NO 211
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
uucugcaagg gcaauagag                                                   19

<210> SEQ ID NO 212
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
gcccuugcag aaaguuuau                                                   19

<210> SEQ ID NO 213
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
auaaacuuuc ugcaagggc                                            19

<210> SEQ ID NO 214
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
cccuugcaga aaguuuauc                                            19

<210> SEQ ID NO 215
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gauaaacuuu cugcaaggg                                            19

<210> SEQ ID NO 216
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
agaaaguuua uccuggcau                                            19

<210> SEQ ID NO 217
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
augccaggau aaacuuucu                                            19

<210> SEQ ID NO 218
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
```
aguuuauccu ggcauacaa                                              19

<210> SEQ ID NO 219
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
uuguaugcca ggauaaacu                                              19

<210> SEQ ID NO 220
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
ccuggcauac aaucgcaug                                              19

<210> SEQ ID NO 221
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
caugcgauug uaugccagg                                              19

<210> SEQ ID NO 222
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
auacaaucgc augugcaca                                              19

<210> SEQ ID NO 223
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
ugugcacaug cgauuguau                                              19

<210> SEQ ID NO 224
<211> LENGTH: 19
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 224
aucgcaugug cacauugaa                                              19

<210> SEQ ID NO 225
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
uucaaugugc acaugcgau                                              19

<210> SEQ ID NO 226
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
gcaugugcac auugaaaac                                              19

<210> SEQ ID NO 227
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227 guuucaaug ugcacaugc                                               19

<210> SEQ ID NO 228
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ugcacauuga aaacuguga                                              19

<210> SEQ ID NO 229
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
ucacaguuuu caaugugca                                              19

```
<210> SEQ ID NO 230
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
auugaaaacu gugacucga                                                  19

<210> SEQ ID NO 231
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
ucgagucaca guuuucaau                                                  19

<210> SEQ ID NO 232
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
aaaacuguga cucgaguga                                                  19

<210> SEQ ID NO 233
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
ucacucgagu cacaguuuu                                                  19

<210> SEQ ID NO 234
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
ugugacucga gugacccua                                                  19

<210> SEQ ID NO 235
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 235
uagggucacu cgagucaca                                          19

<210> SEQ ID NO 236
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
gagugacccu acugcauac                                          19

<210> SEQ ID NO 237
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
guaugcagua gggucacuc                                          19

<210> SEQ ID NO 238
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gacccuacug cauaccugu                                          19

<210> SEQ ID NO 239
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
acagguaugc aguaggguc                                          19

<210> SEQ ID NO 240
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
ccuacugcau accuguaaa                                          19

<210> SEQ ID NO 241
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 241
uuuacaggua ugcaguagg                                                    19

<210> SEQ ID NO 242
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
cugcauaccu guaaaucga                                                    19

<210> SEQ ID NO 243
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
ucgauuuaca gguaugcag                                                    19

<210> SEQ ID NO 244
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
ccuguaaauc gaaggccaa                                                    19

<210> SEQ ID NO 245
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
uuggccuucg auuuacagg                                                    19

<210> SEQ ID NO 246
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
aaucgaaggc caaugguca                                                    19
```

```
<210> SEQ ID NO 247
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ugaccauugg ccuucgauu                                                    19

<210> SEQ ID NO 248
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
aggccaaugg ucagaucuu                                                    19

<210> SEQ ID NO 249
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
aagaucugac cauuggccu                                                    19

<210> SEQ ID NO 250
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
caauggucag aucuucaaa                                                    19

<210> SEQ ID NO 251
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
uuugaagauc ugaccauug                                                    19

<210> SEQ ID NO 252
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 252
cagaucuuca aaauaaaaa                                          19

<210> SEQ ID NO 253
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
uuuuuauuuu gaagaucug                                          19

<210> SEQ ID NO 254
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
auaaaaaguc aucuuaaaa                                          19

<210> SEQ ID NO 255
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
uuuuaagaug acuuuuuau                                          19

<210> SEQ ID NO 256
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
aagucaucuu aaaaaccug                                          19

<210> SEQ ID NO 257
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
cagguuuuua agaugacuu                                          19

<210> SEQ ID NO 258
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
cuuaaaaacc uggaugcau                                               19

<210> SEQ ID NO 259
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
augcauccag guuuuuaag                                               19

<210> SEQ ID NO 260
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
uuaaaaaccu ggaugcaua                                               19

<210> SEQ ID NO 261
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
uaugcaucca gguuuuuaa                                               19

<210> SEQ ID NO 262
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
ccuggaugca uacccuucu                                               19

<210> SEQ ID NO 263
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
agaaggguau gcauccagg                                               19
```

<210> SEQ ID NO 264
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
ggaugcauac ccuucucuu                                                    19

<210> SEQ ID NO 265
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
aagagaaggg uaugcaucc                                                    19

<210> SEQ ID NO 266
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
uacccuucuc uucaagaaa                                                    19

<210> SEQ ID NO 267
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
uuucuugaag agaagggua                                                    19

<210> SEQ ID NO 268
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ccuucucuuc aagaaauuu                                                    19

<210> SEQ ID NO 269
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 269
aaauuucuug aagagaagg                                                19

<210> SEQ ID NO 270
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
caagaaauuu guguucaca                                                19

<210> SEQ ID NO 271
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
ugugaacaca aauuucuug                                                19

<210> SEQ ID NO 272
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
agaaauuugu guucacaaa                                                19

<210> SEQ ID NO 273
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
uuugugaaca caaauuucu                                                19

<210> SEQ ID NO 274
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
uuguguucac aaaggaaaa                                                19

<210> SEQ ID NO 275
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
uuuuccuuug ugaacacaa                                                    19

<210> SEQ ID NO 276
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
cacaaaggaa aaaugcaug                                                    19

<210> SEQ ID NO 277
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
caugcauuuu uccuuugug                                                    19

<210> SEQ ID NO 278
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
caaaggaaaa augcaugaa                                                    19

<210> SEQ ID NO 279
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
uucaugcauu uuccuuug                                                     19

<210> SEQ ID NO 280
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
```
gaaaaaugca ugaagggau                    19

<210> SEQ ID NO 281
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
aucccuucau gcauuuuuc                    19

<210> SEQ ID NO 282
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
augcaugaag ggauggaua                    19

<210> SEQ ID NO 283
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
uauccauccc uucaugcau                    19

<210> SEQ ID NO 284
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
agggauggau accccauuu                    19

<210> SEQ ID NO 285
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285 aaaugggua uccaucccu                     19

<210> SEQ ID NO 286
<211> LENGTH: 19
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 286
gggauggaua ccccauuuu                                               19

<210> SEQ ID NO 287
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
aaaauggggu auccauccc                                               19

<210> SEQ ID NO 288
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
accccauuuu ccaugacau                                               19

<210> SEQ ID NO 289
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
augucaugga aaauggggu                                               19

<210> SEQ ID NO 290
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
ccccauuuuc caugacaug                                               19

<210> SEQ ID NO 291
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
caugucaugg aaaauggg                                                19

<210> SEQ ID NO 292
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ccaugacaug auuauuaca                                                19

<210> SEQ ID NO 293
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
uguaauaauc augcaugg                                                 19

<210> SEQ ID NO 294
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
ugacaugauu auuacacau                                                19

<210> SEQ ID NO 295
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
auguguaaua aucauguca                                                19

<210> SEQ ID NO 296
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gauuauuaca cauugcaug                                                19

<210> SEQ ID NO 297
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
```

```
caugcaaugu guauaaauc                                                    19

<210> SEQ ID NO 298
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
uacacauugc augccugua                                                    19

<210> SEQ ID NO 299
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
uacaggcaug caaugugua                                                    19

<210> SEQ ID NO 300
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
auugcaugcc uguaucaaa                                                    19

<210> SEQ ID NO 301
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
uuugauacag gcaugcaau                                                    19

<210> SEQ ID NO 302
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
uugcaugccu guaucaaaa                                                    19

<210> SEQ ID NO 303
<211> LENGTH: 19
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 303
uuuugauaca ggcaugcaa                                                19

<210> SEQ ID NO 304
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
uaucaaaaca ucucacgua                                                19

<210> SEQ ID NO 305
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
uacgugagau guuuugaua                                                19

<210> SEQ ID NO 306
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
caucucacgu accucauaa                                                19

<210> SEQ ID NO 307
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
uuaugaggua cgugagaug                                                19

<210> SEQ ID NO 308
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
cacguaccuc auaaacaua                                                19

```
<210> SEQ ID NO 309
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
uauguuuaug agguacgug                                            19

<210> SEQ ID NO 310
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
cguaccucau aaacauaua                                            19

<210> SEQ ID NO 311
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
uauauguuua ugagguacg                                            19

<210> SEQ ID NO 312
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
aaacauauac accuaugua                                            19

<210> SEQ ID NO 313
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
uacauaggug uauauguuu                                            19

<210> SEQ ID NO 314
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 314
acaccuaugu acccacaaa                                                    19

<210> SEQ ID NO 315
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
uuugugggua cauaggugu                                                    19

<210> SEQ ID NO 316
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
caccuaugua cccacaaaa                                                    19

<210> SEQ ID NO 317
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317 uuuguggu acauaggug                                                      19

<210> SEQ ID NO 318
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
acccacaaaa auuuuuuaa                                                    19

<210> SEQ ID NO 319
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
uuaaaaaauu uuuguggu                                                     19

<210> SEQ ID NO 320
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 320
caaaaauuuu uuaauuaaa                                                      19

<210> SEQ ID NO 321
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
uuuaauuaaa aaauuuuug                                                      19

<210> SEQ ID NO 322
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
uuuaauuaaa aaaaggaaa                                                      19

<210> SEQ ID NO 323
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
uuuccuuuuu uuaauuaaa                                                      19

<210> SEQ ID NO 324
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324 uuaaaaaag gaaauuuga                                                       19

<210> SEQ ID NO 325
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
ucaaauuccc uuuuuuaa                                                       19
```

```
<210> SEQ ID NO 326
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
aaaggaaauu ugaguuuaa                                                  19

<210> SEQ ID NO 327
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
uuaaacucaa auuccuuu                                                   19

<210> SEQ ID NO 328
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
ggaaauuuga guuuaaaua                                                  19

<210> SEQ ID NO 329
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
uauuuaaacu caaauuucc                                                  19

<210> SEQ ID NO 330
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
aauuugaguu uaaauagaa                                                  19

<210> SEQ ID NO 331
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 331
uucuauuuaa acucaaauu                                              19

<210> SEQ ID NO 332
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
aguuuaaaua gaaacauga                                              19

<210> SEQ ID NO 333
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
ucauguuucu auuuaaacu                                              19

<210> SEQ ID NO 334
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
uaaauagaaa caugauaaa                                              19

<210> SEQ ID NO 335
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
uuuaucaugu uucuauuua                                              19

<210> SEQ ID NO 336
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
gaaacaugau aaaugcaag                                              19

<210> SEQ ID NO 337
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
cuugcauuua ucauguuuc                                                     19

<210> SEQ ID NO 338
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
gauaaaugca agaaagaaa                                                     19

<210> SEQ ID NO 339
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
uuucuuucuu gcauuuauc                                                     19

<210> SEQ ID NO 340
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
aaaugcaaga agaaaaca                                                      19

<210> SEQ ID NO 341
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
uguuuucuuu cuugcauuu                                                     19

<210> SEQ ID NO 342
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
caagaaagaa aacauuuug                                                     19
```

<210> SEQ ID NO 343
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
caaaauguuu ucuuucuug                                                19

<210> SEQ ID NO 344
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
agaaaacauu uugauuuua                                                19

<210> SEQ ID NO 345
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
uaaaaucaaa auguuuucu                                                19

<210> SEQ ID NO 346
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
cauuuugauu uuaacucau                                                19

<210> SEQ ID NO 347
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
augaguuaaa aucaaaaug                                                19

<210> SEQ ID NO 348
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 348
gauuuuaacu cauugucac                                                19

<210> SEQ ID NO 349
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
gugacaauga guuaaaauc                                                19

<210> SEQ ID NO 350
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
auuuuaacuc auugucacu                                                19

<210> SEQ ID NO 351
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
agugacaaug aguuaaaau                                                19

<210> SEQ ID NO 352
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
cauugucacu cugauguuc                                                19

<210> SEQ ID NO 353
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
gaacaucaga gugacaaug                                                19

<210> SEQ ID NO 354
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
uugucacucu gauguucau                                               19

<210> SEQ ID NO 355
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
augaacauca gagugacaa                                               19

<210> SEQ ID NO 356
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
cucugauguu caugugaac                                               19

<210> SEQ ID NO 357
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
guucacauga acaucagag                                               19

<210> SEQ ID NO 358
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gauguucaug ugaacuggu                                               19

<210> SEQ ID NO 359
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
```
accaguucac augaacauc                                                19

<210> SEQ ID NO 360
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
caugugaacu gguugcuuc                                                19

<210> SEQ ID NO 361
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
gaagcaacca guucacaug                                                19

<210> SEQ ID NO 362
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
acugguugcu ucgggcucu                                                19

<210> SEQ ID NO 363
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
agagcccgaa gcaaccagu                                                19

<210> SEQ ID NO 364
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
guugcuucgg gcucuuuga                                                19

<210> SEQ ID NO 365
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 365
ucaaagagcc cgaagcaac                                                19

<210> SEQ ID NO 366
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
gcuucgggcu cuuugaucu                                                19

<210> SEQ ID NO 367
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
agaucaaaga gcccgaagc                                                19

<210> SEQ ID NO 368
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
cgggcucuuu gaucuguca                                                19

<210> SEQ ID NO 369
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
ugacagauca aagagcccg                                                19

<210> SEQ ID NO 370
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
ucuuugaucu gucaccuau                                                19

<210> SEQ ID NO 371
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
auaggugaca gaucaaaga                                                    19

<210> SEQ ID NO 372
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
gaucugucac cuauggaau                                                    19

<210> SEQ ID NO 373
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
auuccauagg ugacagauc                                                    19

<210> SEQ ID NO 374
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
caccuaugga aucugagug                                                    19

<210> SEQ ID NO 375
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
cacucagauu ccauaggug                                                    19

<210> SEQ ID NO 376
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
```
ggaaucugag ugguuuuau                                              19

<210> SEQ ID NO 377
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
auaaaaccac ucagauucc                                              19

<210> SEQ ID NO 378
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
cugagugguu uuauuuuuu                                              19

<210> SEQ ID NO 379
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
aaaaaauaaa accacucag                                              19

<210> SEQ ID NO 380
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
gagugguuuu auuuuuuag                                              19

<210> SEQ ID NO 381
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
cuaaaaaaua aaaccacuc                                              19

<210> SEQ ID NO 382
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 382
gguuuuauuu uuuagauuu                                                       19

<210> SEQ ID NO 383
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
aaaucuaaaa aauaaaacc                                                       19

<210> SEQ ID NO 384
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
auuuuuuaga uuucucagu                                                       19

<210> SEQ ID NO 385
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
acugagaaau cuaaaaaau                                                       19

<210> SEQ ID NO 386
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
uagauuucuc agucccaaa                                                       19

<210> SEQ ID NO 387
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
uuugggacug agaaaucua                                                       19
```

```
<210> SEQ ID NO 388
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
cucaguccca aagaucuaa                                                  19

<210> SEQ ID NO 389
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
uuagaucuuu gggacugag                                                  19

<210> SEQ ID NO 390
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
ucccaaagau cuaagauaa                                                  19

<210> SEQ ID NO 391
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
uuaucuuaga ucuuuggga                                                  19

<210> SEQ ID NO 392
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
caaagaucua agauaaaua                                                  19

<210> SEQ ID NO 393
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 393
uauuuaucuu agaucuuug                                               19

<210> SEQ ID NO 394
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
cuaagauaaa uaaacaaga                                               19

<210> SEQ ID NO 395
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
ucuuguuuau uuaucuuag                                               19

<210> SEQ ID NO 396
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
aagauaaaua aacaagaga                                               19

<210> SEQ ID NO 397
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
ucucuuguuu auuuaucuu                                               19

<210> SEQ ID NO 398
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
auuaagccaa uuaaguauaa a                                            21

<210> SEQ ID NO 399
<211> LENGTH: 23
<212> TYPE: RNA
<213> ORGANISM: Artificial Sequence
```

-continued

<220> FEATURE:
<221> NAME/KEY: source
<223> OTHER INFORMATION: /note="Description of Artificial Sequence:
      Synthetic oligonucleotide"

<400> SEQUENCE: 399
uuuauacuua auuggcuuaa ugu                                            23

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
cauuaagcca auuaaguaua a                                              21

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
uuauacuuaa uuggcuuaau gua                                            23

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
cuacauuaag ccaauuaagu a                                              21

<210> SEQ ID NO 403
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
uacuuaauug gcuuaaugua gaa                                            23

<210> SEQ ID NO 404
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
uacauuaagc caauuaagua u                                              21

```
<210> SEQ ID NO 405
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
auacuuaauu ggcuuaaugu aga                                           23

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
acauuaagcc aauuaaguau a                                             21

<210> SEQ ID NO 407
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
uauacuuaau uggcuuaaug uag                                           23

<210> SEQ ID NO 408
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
uguggacagu acucugcuca a                                             21

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
uugagcagag uacuguccac agc                                           23

<210> SEQ ID NO 410
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 410
aagccaauua aguauaaagg u                                              21

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
accuuuauac uuaauuggcu uaa                                            23

<210> SEQ ID NO 412
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
uuaagccaau uaaguauaaa g                                              21

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
cuuuauacuu aauuggcuua aug                                            23

<210> SEQ ID NO 414
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
ggcuguggac aguacucugc u                                              21

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
agcagaguac uguccacagc cau                                            23

<210> SEQ ID NO 416
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
cuguggacag uacucugcuc a                                              21

<210> SEQ ID NO 417
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
ugagcagagu acguccaca gcc                                             23

<210> SEQ ID NO 418
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
guggacagua cucugcucaa a                                              21

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
uuugagcaga guacugucca cag                                            23

<210> SEQ ID NO 420
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
gcuguggaca guacucugcu c                                              21

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
gagcagagua cuguccacag cca                                            23
```

<210> SEQ ID NO 422
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
uaagccaauu aaguauaaag g                                               21

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
ccuuuauacu uaauuggcuu aau                                             23

<210> SEQ ID NO 424
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
gacaguacuc ugcucaaaga a                                               21

<210> SEQ ID NO 425
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
uucuuugagc agaguacugu cca                                             23

<210> SEQ ID NO 426
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
ggacaguacu cugcucaaag a                                               21

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 427
ucuuugagca gaguacuguc cac                                           23

<210> SEQ ID NO 428
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
uggacaguac ucugcucaaa g                                             21

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
cuuugagcag aguacugucc aca                                           23

<210> SEQ ID NO 430
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
uuaagccaau uaaguauaaa u                                             21

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
auuuauacuu aauuggcuua aug                                           23

<210> SEQ ID NO 432
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
gcuguggaca guacucugcu a                                             21

<210> SEQ ID NO 433
<211> LENGTH: 23

```
-continued

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
uagcagagua cguccacag cca                                              23

<210> SEQ ID NO 434
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
uaagccaauu aaguauaaag a                                               21

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
ucuuuauacu uaauuggcuu aau                                             23

<210> SEQ ID NO 436
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
uggacaguac ucugcucaaa u                                               21

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
auuugagcag aguacugucc aca                                             23

<210> SEQ ID NO 438
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
```
agccaauuaa guauaaaggu a                                              21

<210> SEQ ID NO 439
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
uaccuuuaua cuuaauuggc uua                                            23

<210> SEQ ID NO 440
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
agccaauuaa guauaaaggu c                                              21

<210> SEQ ID NO 441
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
gaccuuuaua cuuaauuggc uua                                            23

<210> SEQ ID NO 442
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
ucuacauuaa gccaauuaag u                                              21

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
acuuaauugg cuuaauguag aac                                            23

<210> SEQ ID NO 444
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 444
uucuacauua agccaauuaa g                                              21

<210> SEQ ID NO 445
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
cuuaauuggc uuaauguaga aca                                            23

<210> SEQ ID NO 446
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
guucuacauu aagccaauua a                                              21

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
uuaauuggcu uaauguagaa cau                                            23

<210> SEQ ID NO 448
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
uguucuacau uaagccaauu a                                              21

<210> SEQ ID NO 449
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
uaauuggcuu aauguagaac auu                                            23

<210> SEQ ID NO 450
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
cauggcugug gacaguacuc u                                              21

<210> SEQ ID NO 451
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
agaguacugu ccacagccau ggc                                            23

<210> SEQ ID NO 452
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
uggcugugga caguacucug c                                              21

<210> SEQ ID NO 453
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
gcagaguacu guccacagcc aug                                            23

<210> SEQ ID NO 454
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
uucuacauua agccaauuaa a                                              21

<210> SEQ ID NO 455
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
```

```
uuuaauuggc uuaauguaga aca                                            23

<210> SEQ ID NO 456
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
uggcugugga caguacucug a                                              21

<210> SEQ ID NO 457
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
ucagaguacu guccacagcc aug                                            23

<210> SEQ ID NO 458
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
gcuaauauau gugcuggcaa a                                              21

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
uuugccagca cauauauuag ccc                                            23

<210> SEQ ID NO 460
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gcccuugcag aaaguuuauc a                                              21

<210> SEQ ID NO 461
<211> LENGTH: 23
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 461
ugauaaacuu ucugcaaggg caa                                            23

<210> SEQ ID NO 462
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
uugaauauuc uucaaagaga a                                              21

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
uucucuuuga agaauauuca agu                                            23

<210> SEQ ID NO 464
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
gcuaauauau gugcuggcaa g                                              21

<210> SEQ ID NO 465
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
cuugccagca cauauauuag ccc                                            23

<210> SEQ ID NO 466
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
auucauucaa acuugaauau u                                              21
```

```
<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
aauauucaag uuugaaugaa uac                                              23

<210> SEQ ID NO 468
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
agcuaggaag uauucauuca a                                                21

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
uugaaugaau acuuccuagc uau                                              23

<210> SEQ ID NO 470
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470 cauggucag aucuucaaaa u                                                 21

<210> SEQ ID NO 471
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
auuuugaaga ucugaccauu ggc                                              23

<210> SEQ ID NO 472
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 472
uggucagauc uucaaaauaa a                                              21

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
uuuauuuuga agaucugacc auu                                            23

<210> SEQ ID NO 474
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
ccaggagaaa ccuuaucaaa a                                              21

<210> SEQ ID NO 475
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
uuuugauaag guuucuccug gcc                                            23

<210> SEQ ID NO 476
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
cccuugcaga aaguuuaucc u                                              21

<210> SEQ ID NO 477
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
aggauaaacu uucugcaagg gca                                            23

<210> SEQ ID NO 478
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 478
uucaaacuug aauauucuuc a                                              21

<210> SEQ ID NO 479
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
ugaagaauau ucaaguuuga aug                                            23

<210> SEQ ID NO 480
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
uagcuaggaa guauucauuc a                                              21

<210> SEQ ID NO 481
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
ugaaugaaua cuuccuagcu auu                                            23

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gcccuugcag aaaguuuauc c                                              21

<210> SEQ ID NO 483
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
ggauaaacuu ucugcaaggg caa                                            23
```

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 484
uugaauauuc uucaaagaga g                                            21

<210> SEQ ID NO 485
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
cucucuuuga agaauauuca agu                                          23

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486
ccaaugguca gaucuucaaa a                                            21

<210> SEQ ID NO 487
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 487
uuuugaagau cugaccauug gcc                                          23

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 488
aauggucaga ucuucaaaau a                                            21

<210> SEQ ID NO 489
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 489
uauuuugaag aucugaccau ugg                                         23

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490 uguggccag gagaaaccuu a                                            21

<210> SEQ ID NO 491
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
uaagguuucu ccuggcccac aau                                         23

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
gacaucuugu gcucugcugg a                                           21

<210> SEQ ID NO 493
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
uccagcagag cacaagaugu cca                                         23

<210> SEQ ID NO 494
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 494
gcatcctggg ctacactga                                              19

<210> SEQ ID NO 495
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 495
tgggtgtcgc tgttgaagtc                                              20

<210> SEQ ID NO 496
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 496
ccaggtggtc tcctcc                                                  16

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
uagcuaggaa guauucauuc a                                            21

<210> SEQ ID NO 498
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
ugaaugaaua cuuccuagcu auu                                          23

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
agcuaggaag uauucauuca a                                            21

<210> SEQ ID NO 500
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
uugaaugaau acuuccuagc uau                                          23
```

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
auucauucaa acuugaauau u                                              21

<210> SEQ ID NO 502
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
aauauucaag uuugaaugaa uac                                            23

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
uucaaacuug aauauucuuc a                                              21

<210> SEQ ID NO 504
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
ugaagaauau ucaaguuuga aug                                            23

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
uugaauauuc uucaaagaga g                                              21

<210> SEQ ID NO 506
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
          Synthetic oligonucleotide"

<400> SEQUENCE: 506
cucucuuuga agaauauuca agu                                              23

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
uugaauauuc uucaaagaga a                                                21

<210> SEQ ID NO 508
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
uucucuuuga agaauauuca agu                                              23

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
gcuaauauau gugcuggcaa g                                                21

<210> SEQ ID NO 510
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
cuugccagca cauauauuag ccc                                              23

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
gcuaauauau gugcuggcaa a                                                21

<210> SEQ ID NO 512
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
uuugccagca cauauauuag ccc                                           23

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
cauggcugug gacaguacuc u                                             21

<210> SEQ ID NO 514
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
agaguacugu ccacagccau ggc                                           23

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
uggcugugga caguacucug c                                             21

<210> SEQ ID NO 516
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
gcagaguacu guccacagcc aug                                           23

<210> SEQ ID NO 517
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
```
uggcugugga caguacucug a                                        21

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
ucagaguacu guccacagcc aug                                      23

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
ggcuguggac aguacucugc u                                        21

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
agcagaguac uguccacagc cau                                      23

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
gcuguggaca guacucugcu c                                        21

<210> SEQ ID NO 522
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
gagcagagua cuguccacag cca                                      23

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 523
gcuguggaca guacucugcu a                                              21

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 524
uagcagagua cuguccacag cca                                            23

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 525
cuguggacag uacucugcuc a                                              21

<210> SEQ ID NO 526
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 526
ugagcagagu acuguccaca gcc                                            23

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 527
uguggacagu acucugcuca a                                              21

<210> SEQ ID NO 528
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 528
uugagcagag uacuguccac agc                                            23

<210> SEQ ID NO 529

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
guggacagua cucugcucaa a                                           21

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
uuugagcaga guacugucca cag                                         23

<210> SEQ ID NO 531
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
uggacaguac ucugcucaaa g                                           21

<210> SEQ ID NO 532
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
cuuugagcag aguacugucc aca                                         23

<210> SEQ ID NO 533
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
uggacaguac ucugcucaaa u                                           21

<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
```
auuugagcag aguacugucc aca         23

<210> SEQ ID NO 535
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
ggacaguacu cugcucaaag a         21

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
ucuuugagca gaguacuguc cac         23

<210> SEQ ID NO 537
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
gacaguacuc ugcucaaaga a         21

<210> SEQ ID NO 538
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
uucuuugagc agaguacugu cca         23

<210> SEQ ID NO 539
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
ugugggccag gagaaaccuu a         21

<210> SEQ ID NO 540
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 540
uaagguuucu ccuggcccac aau                                              23

<210> SEQ ID NO 541
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
ccaggagaaa ccuuaucaaa a                                                21

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
uuuugauaag guuucccug gcc                                               23

<210> SEQ ID NO 543
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
uguucuacau uaagccaauu a                                                21

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
uaauuggcuu aauguagaac auu                                              23

<210> SEQ ID NO 545
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
guucuacauu aagccaauua a                                                21

```
<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
uuaauuggcu uaauguagaa cau                                            23

<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
uucuacauua agccaauuaa g                                              21

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
cuuaauuggc uuaauguaga aca                                            23

<210> SEQ ID NO 549
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
uucuacauua agccaauuaa a                                              21

<210> SEQ ID NO 550
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
uuuaauuggc uuaauguaga aca                                            23

<210> SEQ ID NO 551
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 551
ucuacauuaa gccaauuaag u                                              21

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
acuuaauugg cuuaauguag aac                                            23

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
cuacauuaag ccaauuaagu a                                              21

<210> SEQ ID NO 554
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
uacuuaauug gcuuaaugua gaa                                            23

<210> SEQ ID NO 555
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
uacauuaagc caauuaagua u                                              21

<210> SEQ ID NO 556
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
auacuuaauu ggcuuaaugu aga                                            23

<210> SEQ ID NO 557
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 557
acauuaagcc aauuaaguau a                                              21

<210> SEQ ID NO 558
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uauacuuaau uggcuuaaug uag                                            23

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
cauuaagcca auuaaguaua a                                              21

<210> SEQ ID NO 560
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
uuauacuuaa uuggcuuaau gua                                            23

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
auuaagccaa uuaaguauaa a                                              21

<210> SEQ ID NO 562
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
uuuauacuua auuggcuuaa ugu                                            23
```

<210> SEQ ID NO 563
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
uuaagccaau uaaguauaaa g                                              21

<210> SEQ ID NO 564
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
cuuuauacuu aauuggcuua aug                                            23

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
uuaagccaau uaaguauaaa u                                              21

<210> SEQ ID NO 566
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
auuuauacuu aauuggcuua aug                                            23

<210> SEQ ID NO 567
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
uaagccaauu aaguauaaag g                                              21

<210> SEQ ID NO 568
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 568
ccuuuauacu uaauuggcuu aau                                          23

<210> SEQ ID NO 569
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
uaagccaauu aaguauaaag a                                            21

<210> SEQ ID NO 570
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
ucuuuauacu uaauuggcuu aau                                          23

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
aagccaauua aguauaaagg u                                            21

<210> SEQ ID NO 572
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
accuuuauac uuaauuggcu uaa                                          23

<210> SEQ ID NO 573
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
agccaauuaa guauaaaggu c                                            21

<210> SEQ ID NO 574
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
gaccuuuaua cuuaauuggc uua                                              23

<210> SEQ ID NO 575
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
agccaauuaa guauaaaggu a                                                21

<210> SEQ ID NO 576
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
uaccuuuaua cuuaauuggc uua                                              23

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
gcccuugcag aaaguuuauc c                                                21

<210> SEQ ID NO 578
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
ggauaaacuu ucugcaaggg caa                                              23

<210> SEQ ID NO 579
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
gcccuugcag aaaguuuauc a                                                21
```

<210> SEQ ID NO 580
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
ugauaaacuu ucugcaaggg caa                                          23

<210> SEQ ID NO 581
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
cccuugcaga aaguuuaucc u                                            21

<210> SEQ ID NO 582
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
aggauaaacu uucugcaagg gca                                          23

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
ccaaugguca gaucuucaaa a                                            21

<210> SEQ ID NO 584
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
uuuugaagau cugaccauug gcc                                          23

<210> SEQ ID NO 585
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 585
caauggucag aucuucaaaa u                                              21

<210> SEQ ID NO 586
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
auuuugaaga ucugaccauu ggc                                            23

<210> SEQ ID NO 587
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
aauggucaga ucuucaaaau a                                              21

<210> SEQ ID NO 588
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
uauuuugaag aucugaccau ugg                                            23

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
uggucagauc uucaaaauaa a                                              21

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
uuuauuuuga agaucugacc auu                                            23

<210> SEQ ID NO 591
<211> LENGTH: 21

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
uagcuaggaa guauucauuc a                                              21

<210> SEQ ID NO 592
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
ugaaugaaua cuuccuagcu auu                                            23

<210> SEQ ID NO 593
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
agcuaggaag uauucauuca a                                              21

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uugaaugaau acuuccuagc uau                                            23

<210> SEQ ID NO 595
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
auucauucaa acuugaauau u                                              21

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
```
aauauucaag uuugaaugaa uac   23

<210> SEQ ID NO 597
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
uucaaacuug aauauucuuc a   21

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
ugaagaauau ucaaguuuga aug   23

<210> SEQ ID NO 599
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uugaauauuc uucaaagaga g   21

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
cucucuuuga agaauauuca agu   23

<210> SEQ ID NO 601
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
uugaauauuc uucaaagaga a   21

<210> SEQ ID NO 602
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 602
uucucuuuga agaauauuca agu                                              23

<210> SEQ ID NO 603
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
gcuaauauau gugcuggcaa g                                                21

<210> SEQ ID NO 604
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
cuugccagca cauauauuag ccc                                              23

<210> SEQ ID NO 605
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
gcuaauauau gugcuggcaa a                                                21

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
uuugccagca cauauauuag ccc                                              23

<210> SEQ ID NO 607
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
cauggcugug gacaguacuc u                                                21

<210> SEQ ID NO 608
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
agaguacugu ccacagccau ggc                                             23

<210> SEQ ID NO 609
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uggcugugga caguacucug c                                               21

<210> SEQ ID NO 610
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
gcagaguacu guccacagcc aug                                             23

<210> SEQ ID NO 611
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
uggcugugga caguacucug a                                               21

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
ucagaguacu guccacagcc aug                                             23

<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
```

```
ggcuguggac aguacucugc u                                    21

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
agcagaguac uguccacagc cau                                  23

<210> SEQ ID NO 615
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
gcuguggaca guacucugcu c                                    21

<210> SEQ ID NO 616
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
gagcagagua cuguccacag cca                                  23

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
gcuguggaca guacucugcu a                                    21

<210> SEQ ID NO 618
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
uagcagagua cuguccacag cca                                  23

<210> SEQ ID NO 619
<211> LENGTH: 21
<212> TYPE: RNA
<213> ORGANISM: Artificial Sequence
<220> FEATURE:
```

-continued

<221> NAME/KEY: source
<223> OTHER INFORMATION: /note="Description of Artificial Sequence: Synthetic oligonucleotide"

<400> SEQUENCE: 619
cuguggacag uacucugcuc a                 21

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 620
ugagcagagu acuguccaca gcc               23

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 621
uguggacagu acucugcuca a                 21

<210> SEQ ID NO 622
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 622
uugagcagag uacuguccac agc               23

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 623
guggacagua cucugcucaa a                 21

<210> SEQ ID NO 624
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 624
uuugagcaga guacugucca cag               23

```
<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
uggacaguac ucugcucaaa g                                          21

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
cuuugagcag aguacugucc aca                                        23

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uggacaguac ucugcucaaa u                                          21

<210> SEQ ID NO 628
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
auuugagcag aguacugucc aca                                        23

<210> SEQ ID NO 629
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
ggacaguacu cugcucaaag a                                          21

<210> SEQ ID NO 630
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 630
ucuuugagca gaguacuguc cac                                          23

<210> SEQ ID NO 631
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
gacaguacuc ugcucaaaga a                                            21

<210> SEQ ID NO 632
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
uucuuugagc agaguacugu cca                                          23

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
ugugggccag gagaaaccuu a                                            21

<210> SEQ ID NO 634
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
uaagguuucu ccuggcccac aau                                          23

<210> SEQ ID NO 635
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
ccaggagaaa ccuuaucaaa a                                            21

<210> SEQ ID NO 636
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 636
uuuugauaag guuucuccug gcc                                            23

<210> SEQ ID NO 637
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
uguucuacau uaagccaauu a                                              21

<210> SEQ ID NO 638
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
uaauuggcuu aauguagaac auu                                            23

<210> SEQ ID NO 639
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
guucuacauu aagccaauua a                                              21

<210> SEQ ID NO 640
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
uuaauuggcu aauguagaa cau                                             23

<210> SEQ ID NO 641
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
uucuacauua agccaauuaa g                                              21
```

<210> SEQ ID NO 642
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
cuuaauuggc uuaauguaga aca                                              23

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
uucuacauua agccaauuaa a                                                21

<210> SEQ ID NO 644
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
uuuaauuggc uuaauguaga aca                                              23

<210> SEQ ID NO 645
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
ucuacauuaa gccaauuaag u                                                21

<210> SEQ ID NO 646
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
acuuaauugg cuuaauguag aac                                              23

<210> SEQ ID NO 647
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 647
cuacauuaag ccaauuaagu a					21

<210> SEQ ID NO 648
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
uacuuaauug gcuuaaugua gaa				23

<210> SEQ ID NO 649
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
uacauuaagc caauuaagua u					21

<210> SEQ ID NO 650
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
auacuuaauu ggcuuaaugu aga				23

<210> SEQ ID NO 651
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
acauuaagcc aauuaaguau a					21

<210> SEQ ID NO 652
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
uauacuuaau uggcuuaaug uag				23

<210> SEQ ID NO 653
<211> LENGTH: 21
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
cauuaagcca auuaaguaua a                                              21

<210> SEQ ID NO 654
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
uuauacuuaa uuggcuuaau gua                                            23

<210> SEQ ID NO 655
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
auuaagccaa uuaaguauaa a                                              21

<210> SEQ ID NO 656
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
uuuauacuua auuggcuuaa ugu                                            23

<210> SEQ ID NO 657
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
uuaagccaau uaaguauaaa g                                              21

<210> SEQ ID NO 658
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
cuuuauacuu aauuggcuua aug                                            23
```

<210> SEQ ID NO 659
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
uuaagccaau uaaguauaaa u                                              21

<210> SEQ ID NO 660
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
auuuauacuu aauuggcuua aug                                            23

<210> SEQ ID NO 661
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
uaagccaauu aaguauaaag g                                              21

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
ccuuuauacu uaauuggcuu aau                                            23

<210> SEQ ID NO 663
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
uaagccaauu aaguauaaag a                                              21

<210> SEQ ID NO 664
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 664
ucuuuauacu uaauuggcuu aau                                           23

<210> SEQ ID NO 665
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
aagccaauua aguauaaagg u                                             21

<210> SEQ ID NO 666
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
accuuuauac uuaauuggcu uaa                                           23

<210> SEQ ID NO 667
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
agccaauuaa guauaaaggu c                                             21

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
gaccuuuaua cuuaauuggc uua                                           23

<210> SEQ ID NO 669
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
agccaauuaa guauaaaggu a                                             21

<210> SEQ ID NO 670
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
uaccuuuaua cuuaauuggc uua                                            23

<210> SEQ ID NO 671
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
gcccuugcag aaaguuuauc c                                              21

<210> SEQ ID NO 672
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
ggauaaacuu ucugcaaggg caa                                            23

<210> SEQ ID NO 673
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
gcccuugcag aaaguuuauc a                                              21

<210> SEQ ID NO 674
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
ugauaaacuu ucugcaaggg caa                                            23

<210> SEQ ID NO 675
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
```

-continued cccuugcaga aaguuuaucc u                                              21

<210> SEQ ID NO 676
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
aggauaaacu uucugcaagg gca                                            23

<210> SEQ ID NO 677
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
ccaaugguca gaucuucaaa a                                              21

<210> SEQ ID NO 678
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
uuuugaagau cugaccauug gcc                                            23

<210> SEQ ID NO 679
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
caauggucag aucuucaaaa u                                              21

<210> SEQ ID NO 680
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
auuuugaaga ucugaccauu ggc                                            23

<210> SEQ ID NO 681
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 681
aauggucaga ucuucaaaau a                                                 21

<210> SEQ ID NO 682
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
uauuuugaag aucugaccau ugg                                               23

<210> SEQ ID NO 683
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
uggucagauc uucaaaauaa a                                                 21

<210> SEQ ID NO 684
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
uuuauuuuga agaucugacc auu                                               23

<210> SEQ ID NO 685
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 685

Ala Ala Val Ala Leu Leu Pro Ala Val Leu Leu Ala Leu Leu Ala Pro
1               5                   10                  15

<210> SEQ ID NO 686
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 686

Ala Ala Leu Leu Pro Val Leu Leu Ala Ala Pro
1               5                   10
```

<210> SEQ ID NO 687
<211> LENGTH: 13
<212> TYPE: PRT
<213> ORGANISM: Human immunodeficiency virus

<400> SEQUENCE: 687

Gly Arg Lys Lys Arg Arg Gln Arg Arg Pro Pro Gln
1               5                   10

<210> SEQ ID NO 688
<211> LENGTH: 16
<212> TYPE: PRT
<213> ORGANISM: Drosophila sp.

<400> SEQUENCE: 688

Arg Gln Ile Lys Ile Trp Phe Gln Asn Arg Arg Met Lys Trp Lys Lys
1               5                   10                  15

<210> SEQ ID NO 689

<400> SEQUENCE: 689

000

<210> SEQ ID NO 690
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 690
gaauauuaga acugacuuu t                                              21

<210> SEQ ID NO 691
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 691
aagucaaguu cuaauauuct t                                             21

<210> SEQ ID NO 692
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 692
aacuugacuu gcuccaucct t                                          21

<210> SEQ ID NO 693
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 693
ggauggagca agucaaguut t                                          21

<210> SEQ ID NO 694
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 694
ccauccucuu aaacuuuuut t                                          21

<210> SEQ ID NO 695
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 695
aaaaaguuua agaggauggt t                                          21

<210> SEQ ID NO 696
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 696
uaaacuuuuu gugucucact t                                          21

<210> SEQ ID NO 697
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 697
gugagacaca aaaguuuat t                                              21

<210> SEQ ID NO 698
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 698
gucucacacu aaagaaaugt t                                             21

<210> SEQ ID NO 699
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 699
cauuucuuua gugugagact t                                             21

<210> SEQ ID NO 700
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 700
aaagaaauga gagaugcagt t                                             21

<210> SEQ ID NO 701
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 701
cugcaucucu cauuucuuut t                                              21

<210> SEQ ID NO 702
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 702
augcagaauu cuaaggcuat t                                              21

<210> SEQ ID NO 703
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 703
uagccuuaga auucugcaut t                                              21

<210> SEQ ID NO 704
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 704
ucuaaggcua aauagcuagt t                                              21

<210> SEQ ID NO 705
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 705
cuagcuauuu agccuuagat t                                              21

```
<210> SEQ ID NO 706
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 706
auagcuagga aguauucaut t                                              21

<210> SEQ ID NO 707
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 707
augaauacuu ccuagcuaut t                                              21

<210> SEQ ID NO 708
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 708
auucauucaa acuugaauat t                                              21

<210> SEQ ID NO 709
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 709
uauucaaguu ugaaugaaut t                                              21

<210> SEQ ID NO 710
<211> LENGTH: 21
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 710
cuugaauauu cuucaaagat t                                              21

<210> SEQ ID NO 711
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 711
ucuuugaaga auauucaagt t                                              21

<210> SEQ ID NO 712
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 712
cuucaaagag agugugggt t                                               21

<210> SEQ ID NO 713
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonuclotide"

<400> SEQUENCE: 713
ccccacacuc ucuuugaagt t                                              21

<210> SEQ ID NO 714
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 714 guguggggc aacucuaaut t    21

<210> SEQ ID NO 715
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 715
auuagaguug cccccacact t    21

<210> SEQ ID NO 716
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 716
aacucuaauc agaggaagat t    21

<210> SEQ ID NO 717
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 717
ucuuccucug auuagaguut t    21

<210> SEQ ID NO 718
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 718
aggaagaaac uaaaggaagt t    21

<210> SEQ ID NO 719

-continued

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 719
cuuccuuuag uuucuuccut t                                            21

<210> SEQ ID NO 720
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 720
uaaaggaagu aaaaccagat t                                            21

<210> SEQ ID NO 721
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 721
ucugguuuua cuuccuuuat t                                            21

<210> SEQ ID NO 722
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 722
aaaccagaug uuuuccacct t                                            21

<210> SEQ ID NO 723
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 723
gguggaaaac aucugguuut t                                            21

<210> SEQ ID NO 724
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 724
uccaccaaag cccuccuuut t                                            21

<210> SEQ ID NO 725
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 725
aaaggagggc uuugguggat t                                            21

<210> SEQ ID NO 726
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 726
ccuccuuuug gcuggucugt t                                            21

<210> SEQ ID NO 727
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 727
```
cagaccagcc aaaaggaggt t                                              21

<210> SEQ ID NO 728
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 728
ggcuggucug auuucuacct t                                              21

<210> SEQ ID NO 729
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 729
gguagaaauc agaccagcct t                                              21

<210> SEQ ID NO 730
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 730
uuucuaccgc acuggcaggt t                                              21

<210> SEQ ID NO 731
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 731
ccugccagug cgguagaaat t                                              21

<210> SEQ ID NO 732
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 732
ggcagggcca ugggcuaaut t                                              21

<210> SEQ ID NO 733
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 733
auuagcccau ggcccugcct t                                              21

<210> SEQ ID NO 734
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 734
gggcuaauau augugcuggt t                                              21

<210> SEQ ID NO 735
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 735
ccagcacaua uauuagccct t                                              21

<210> SEQ ID NO 736
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 736
augugcuggc aagucuucct t                                    21

<210> SEQ ID NO 737
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 737
ggaagacuug ccagcacaut t                                    21

<210> SEQ ID NO 738
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 738
aagucuucca augagaucct t                                    21

<210> SEQ ID NO 739
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 739
ggaucucauu ggaagacuut t                                    21

<210> SEQ ID NO 740
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 740
agauccggac gugugaccgt t                                    21

```
<210> SEQ ID NO 741
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 741
cggucacacg uccggaucut t                                              21

<210> SEQ ID NO 742
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 742
gugugaccgc cauggcugut t                                              21

<210> SEQ ID NO 743
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 743
acagccaugg cggucacact t                                              21

<210> SEQ ID NO 744
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 744
auggcugugg acaguacuct t                                              21

<210> SEQ ID NO 745
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 745
gaguacuguc cacagccaut t                                              21

<210> SEQ ID NO 746
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 746
aguacucugc ucaaagaagt t                                              21

<210> SEQ ID NO 747
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 747
cuucuuugag cagaguacut t                                              21

<210> SEQ ID NO 748
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 748
caaagaaguc agaggccuct t                                              21

<210> SEQ ID NO 749
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 749
gaggccucug acuucuuugt t                                              21

<210> SEQ ID NO 750
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 750
cagaggccuc accagggugt t                                              21

<210> SEQ ID NO 751
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 751
cacccuggug aggccucugt t                                              21

<210> SEQ ID NO 752
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 752
ccagggugug gacaucuugt t                                              21

<210> SEQ ID NO 753
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 753
caagaugucc acacccuggt t                                              21

<210> SEQ ID NO 754
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 754
acaucuugug cucugcuggt t                                              21

<210> SEQ ID NO 755
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 755
ccagcagagc acaagaugut t                                              21

<210> SEQ ID NO 756
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 756
cugcuggauc uacuguguat t                                              21

<210> SEQ ID NO 757
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source
<223> OTHER INFORMATION: /note="Description of Combined DNA/RNA
     Molecule: Synthetic oligonucleotide"

<400> SEQUENCE: 757
uacacaguag auccagcagt t                                              21

<210> SEQ ID NO 758
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 758
cuguguacgc accauucact t                                             21

<210> SEQ ID NO 759
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 759
gugaauggug cguacacagt t                                             21

<210> SEQ ID NO 760
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 760
ccauucacug gaaugauugt t                                             21

<210> SEQ ID NO 761
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 761
caaucauucc agugaauggt t                                             21

<210> SEQ ID NO 762
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 762
aaugauugug ggccaggagt t                                             21
```

<210> SEQ ID NO 763
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 763
cuccuggccc acaaucauut t                                              21

<210> SEQ ID NO 764
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 764
gggccaggag aaaccuuaut t                                              21

<210> SEQ ID NO 765
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 765
auaagguuuc uccuggccct t                                              21

<210> SEQ ID NO 766
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 766
ccuuaucaaa acaagaaugt t                                              21

<210> SEQ ID NO 767
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 767
cauucuuguu uugauaaggt t                                              21

<210> SEQ ID NO 768
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 768
caagaaugcu aucaauaaut t                                              21

<210> SEQ ID NO 769
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 769
auuauugaua gcauucuugt t                                              21

<210> SEQ ID NO 770
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 770
aucaauaaug guguucgaat t                                              21

<210> SEQ ID NO 771
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 771
uucgaacacc auuauugaut t                                           21

<210> SEQ ID NO 772
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 772
guucgaauau cuggaagagt t                                           21

<210> SEQ ID NO 773
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 773
cucuuccaga uauucgaact t                                           21

<210> SEQ ID NO 774
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 774
ucuggaagag guuuuugugt t                                           21

<210> SEQ ID NO 775
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 775
cacaaaaacc ucuuccagat t                                           21

<210> SEQ ID NO 776
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 776
uuuuuguguc aaaauguuct t                                              21

<210> SEQ ID NO 777
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 777
gaacauuuug acacaaaaat t                                              21

<210> SEQ ID NO 778
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 778
auguucuaca uuaagccaat t                                              21

<210> SEQ ID NO 779
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 779
uuggcuuaau guagaacaut t                                              21

<210> SEQ ID NO 780
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 780
uaagccaauu aaguauaaat t                                              21

<210> SEQ ID NO 781
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 781
uuuauacuua auuggcuuat t                                              21

<210> SEQ ID NO 782
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 782
aaguauaaag guccuauuat t                                              21

<210> SEQ ID NO 783
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 783
uaauaggacc uuuauacuut t                                              21

<210> SEQ ID NO 784
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 784
ccuauuaaga agggagaaat t                                              21
```

<210> SEQ ID NO 785
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 785
uuucucccuu cuuaauaggt t                                              21

<210> SEQ ID NO 786
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 786
agggagaaaa acuuggaact t                                              21

<210> SEQ ID NO 787
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 787
guuccaaguu uuucucccut t                                              21

<210> SEQ ID NO 788
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 788
cuuggaacuc uauugcccut t                                              21

<210> SEQ ID NO 789
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 789
agggcaauag aguuccaagt t                                              21

<210> SEQ ID NO 790
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 790
uugcccuugc agaaguuut t                                               21

<210> SEQ ID NO 791
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 791
aaacuuucug caagggcaat t                                              21

<210> SEQ ID NO 792
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 792
agaaaguuua uccuggcaut t                                              21

<210> SEQ ID NO 793
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 793
augccaggau aaacuuucut t                                            21

<210> SEQ ID NO 794
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 794
ccuggcauac aaucgcaugt t                                            21

<210> SEQ ID NO 795
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 795
caugcgauug uaugccaggt t                                            21

<210> SEQ ID NO 796
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 796
aucgcaugug cacauugaat t                                            21

<210> SEQ ID NO 797
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 797
uucaaugugc acaugcgaut t                                            21

<210> SEQ ID NO 798

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 798
cauugaaaac ugugacucgt t                                              21

<210> SEQ ID NO 799
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 799
cgagucacag uuuucaaugt t                                              21

<210> SEQ ID NO 800
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 800
gugacucgag ugacccuact t                                              21

<210> SEQ ID NO 801
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 801
guagggucac ucgagucact t                                              21

<210> SEQ ID NO 802
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 802
ugacccuacu gcauaccugt t                                            21

<210> SEQ ID NO 803
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 803
cagguaugca guagggucat t                                            21

<210> SEQ ID NO 804
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 804
cauaccugua aaucgaaggt t                                            21

<210> SEQ ID NO 805
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 805
ccuucgauuu acagguaugt t                                            21

<210> SEQ ID NO 806
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 806
```
uggucagauc uucaaaauat t            21

<210> SEQ ID NO 807
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 807
uauuuugaag aucugaccat t            21

<210> SEQ ID NO 808
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 808
cuucaaaaua aaaagucaut t            21

<210> SEQ ID NO 809
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 809
augacuuuuu auuugaagt t            21

<210> SEQ ID NO 810
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 810
aagucaucuu aaaaaccugt t            21

<210> SEQ ID NO 811
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 811
cagguuuuua agaugacuut t                                              21

<210> SEQ ID NO 812
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 812
aaaaccugga ugcauaccct t                                              21

<210> SEQ ID NO 813
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 813
ggguaugcau ccagguuuut t                                              21

<210> SEQ ID NO 814
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 814
gcauacccuu cucuucaagt t                                              21

<210> SEQ ID NO 815
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 815
cuugaagaga agggauugct t                                          21

<210> SEQ ID NO 816
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 816
cuucaagaaa uuuguguuct t                                          21

<210> SEQ ID NO 817
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 817
gaacacaaau uucuugaagt t                                          21

<210> SEQ ID NO 818
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 818 uuuguucac aaaggaaaat t                                           21

<210> SEQ ID NO 819
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 819
uuuuccuuug ugaacacaat t                                          21

```
<210> SEQ ID NO 820
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 820
aaggaaaaau gcaugaaggt t                                              21

<210> SEQ ID NO 821
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 821
ccuucaugca uuuuuccuut t                                              21

<210> SEQ ID NO 822
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 822
ugcaugaagg gauggauact t                                              21

<210> SEQ ID NO 823
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 823
guauccaucc cuucaugcat t                                              21

<210> SEQ ID NO 824
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 824
uggauacccc auuuuccaut t                                              21

<210> SEQ ID NO 825
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 825
auggaaaaug ggguauccat t                                              21

<210> SEQ ID NO 826
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 826
uuuccaugac augauuauut t                                              21

<210> SEQ ID NO 827
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 827
aauaaucaug ucauggaaat t                                              21

<210> SEQ ID NO 828
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 828

```
caugauuauu acacauugct t                                    21
```

<210> SEQ ID NO 829
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 829

```
gcaaugugua auaaucaugt t                                    21
```

<210> SEQ ID NO 830
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 830

```
cacauugcau gccuguauct t                                    21
```

<210> SEQ ID NO 831
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 831

```
gauacaggca ugcaaugugt t                                    21
```

<210> SEQ ID NO 832
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 832

```
ccuguaucaa aacaucucat t                                    21
```

<210> SEQ ID NO 833
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 833
ugagauguuu ugauacaggt t                                              21

<210> SEQ ID NO 834
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 834
caucucacgu accucauaat t                                              21

<210> SEQ ID NO 835
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 835
uuaugaggua cgugagaugt t                                              21

<210> SEQ ID NO 836
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 836
ccucauaaac auauacacct t                                              21

<210> SEQ ID NO 837
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 837
gguguauaug uuuaugaggt t                                              21

<210> SEQ ID NO 838
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 838
auacaccuau guacccacat t                                              21

<210> SEQ ID NO 839
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 839
uguggguaca uagguguaut t                                              21

<210> SEQ ID NO 840
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 840
guacccacaa aaauuuuuut t                                              21

<210> SEQ ID NO 841
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 841
aaaaaauuuu uguggguact t                                              21
```

```
<210> SEQ ID NO 842
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 842
uaaaaaaagg aaauuugagt t                                              21

<210> SEQ ID NO 843
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 843
cucaaauuuc cuuuuuuat t                                               21

<210> SEQ ID NO 844
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 844
aauuugaguu uaaauagaat t                                              21

<210> SEQ ID NO 845
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 845
uucuauuuaa acucaaauut t                                              21

<210> SEQ ID NO 846
<211> LENGTH: 21
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 846
auagaaacau gauaaaugct t                                              21

<210> SEQ ID NO 847
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 847
gcauuuauca uguuucuaut t                                              21

<210> SEQ ID NO 848
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 848
gauaaaugca agaaagaaat t                                              21

<210> SEQ ID NO 849
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 849
uuucuuucuu gcauuuauct t                                              21

<210> SEQ ID NO 850
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 850
gaaagaaaac auuugauut t                                              21

<210> SEQ ID NO 851
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 851
aaucaaaaug uuucuuuct t                                              21

<210> SEQ ID NO 852
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 852
acucauuguc acucgaugt t                                              21

<210> SEQ ID NO 853
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 853
caucagagug acaaugagut t                                             21

<210> SEQ ID NO 854
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 854
cucugauguu caugugaact t                                             21

<210> SEQ ID NO 855
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 855
guucacauga acaucagagt t                                              21

<210> SEQ ID NO 856
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 856
caugugaacu gguugcuuct t                                              21

<210> SEQ ID NO 857
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 857
gaagcaacca guucacaugt t                                              21

<210> SEQ ID NO 858
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 858
guugcuucgg gcucuuugat t                                              21

<210> SEQ ID NO 859
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 859
ucaaagagcc cgaagcaact t    21

<210> SEQ ID NO 860
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 860
ucuuugaucu gucaccuaut t    21

<210> SEQ ID NO 861
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 861
auaggugaca gaucaaagat t    21

<210> SEQ ID NO 862
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 862
caccuaugga aucugagugt t    21

<210> SEQ ID NO 863
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 863
cacucagauu ccauaggugt t    21

<210> SEQ ID NO 864
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 864 aaucgagug guuuuauuut t                                              21

<210> SEQ ID NO 865
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 865
aaauaaaacc acucagauut t                                             21

<210> SEQ ID NO 866
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 866
uuuuuuagau uucucaguct t                                             21

<210> SEQ ID NO 867
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 867
gacugagaaa ucuaaaaaat t                                             21

<210> SEQ ID NO 868
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 868
cucaguccca aagaucuaat t                                              21

<210> SEQ ID NO 869
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 869
uuagaucuuu gggacugagt t                                              21

<210> SEQ ID NO 870
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 870
gaucuaagau aaauaaacat t                                              21

<210> SEQ ID NO 871
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 871
uguuuauuua ucuuagauct t                                              21

<210> SEQ ID NO 872
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
gaauauuaga acuugacuu                                                 19
```

<210> SEQ ID NO 873
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
aagucaaguu cuaauauuc                                                19

<210> SEQ ID NO 874
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
aacuugacuu gcuccaucc                                                19

<210> SEQ ID NO 875
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
ggauggagca agucaaguu                                                19

<210> SEQ ID NO 876
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
ccauccucuu aaacuuuuu                                                19

<210> SEQ ID NO 877
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
aaaaaguuua agaggaugg                                                19

<210> SEQ ID NO 878
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 878
uaaacuuuuu gugucucac                                                    19

<210> SEQ ID NO 879
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
gugagacaca aaaaguuua                                                    19

<210> SEQ ID NO 880
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
gucucacacu aaagaaaug                                                    19

<210> SEQ ID NO 881
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
cauuucuuua gugugagac                                                    19

<210> SEQ ID NO 882
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
aaagaaauga gagaugcag                                                    19

<210> SEQ ID NO 883
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
cugcaucucu cauuucuuu                                                    19

<210> SEQ ID NO 884
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
augcagaauu cuaaggcua                                                19

<210> SEQ ID NO 885
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
uagccuuaga auucugcau                                                19

<210> SEQ ID NO 886
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
ucuaaggcua aauagcuag                                                19

<210> SEQ ID NO 887
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
cuagcuauuu agccuuaga                                                19

<210> SEQ ID NO 888
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
auagcuagga aguauucau                                                19

<210> SEQ ID NO 889
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
```

```
augaauacuu ccuagcuau                                              19

<210> SEQ ID NO 890
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
auucauucaa acuugaaua                                              19

<210> SEQ ID NO 891
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
uauucaaguu ugaaugaau                                              19

<210> SEQ ID NO 892
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
cuugaauauu cuucaaaga                                              19

<210> SEQ ID NO 893
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
ucuuugaaga auauucaag                                              19

<210> SEQ ID NO 894
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
cuucaaagag agugugggg                                              19

<210> SEQ ID NO 895
<211> LENGTH: 19
<212> TYPE: RNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"

<400> SEQUENCE: 895
ccccacacuc ucuuugaag                                                   19

<210> SEQ ID NO 896
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896 guguggggc aacucuaau                                                    19

<210> SEQ ID NO 897
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
auuagaguug cccccacac                                                   19

<210> SEQ ID NO 898
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
aacucuaauc agaggaaga                                                   19

<210> SEQ ID NO 899
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
ucuuccucug auuagaguu                                                   19

<210> SEQ ID NO 900
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
aggaagaaac uaaaggaag                                                   19

<210> SEQ ID NO 901
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
cuuccuuuag uuucuuccu                                                  19

<210> SEQ ID NO 902
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
uaaaggaagu aaaaccaga                                                  19

<210> SEQ ID NO 903
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
ucugguuuua cuuccuuua                                                  19

<210> SEQ ID NO 904
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
aaaccagaug uuuuccacc                                                  19

<210> SEQ ID NO 905
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
gguggaaaac aucugguuu                                                  19

<210> SEQ ID NO 906
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
```

```
uccaccaaag cccuccuuu                                              19
```

<210> SEQ ID NO 907
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907

```
aaaggagggc uuuggugga                                              19
```

<210> SEQ ID NO 908
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908

```
ccuccuuuug gcuggucug                                              19
```

<210> SEQ ID NO 909
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909

```
cagaccagcc aaaaggagg                                              19
```

<210> SEQ ID NO 910
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910

```
ggcuggucug auuucuacc                                              19
```

<210> SEQ ID NO 911
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911

```
gguagaaauc agaccagcc                                              19
```

<210> SEQ ID NO 912
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 912
uuucuaccgc acuggcagg                                                    19

<210> SEQ ID NO 913
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
ccugccagug cgguagaaa                                                    19

<210> SEQ ID NO 914
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
ggcagggcca ugggcuaau                                                    19

<210> SEQ ID NO 915
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
auuagcccau ggcccugcc                                                    19

<210> SEQ ID NO 916
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
gggcuaauau augugcugg                                                    19

<210> SEQ ID NO 917
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
ccagcacaua uauuagccc                                                    19
```

```
<210> SEQ ID NO 918
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
augugcuggc aagucuucc                                                   19

<210> SEQ ID NO 919
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
ggaagacuug ccagcacau                                                   19

<210> SEQ ID NO 920
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
aagucuucca augagaucc                                                   19

<210> SEQ ID NO 921
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
ggaucucauu ggaagacuu                                                   19

<210> SEQ ID NO 922
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
agauccggac gugugaccg                                                   19

<210> SEQ ID NO 923
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 923
cggucacacg uccggaucu                                              19

<210> SEQ ID NO 924
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
gugugaccgc cauggcugu                                              19

<210> SEQ ID NO 925
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
acagccaugg cggucacac                                              19

<210> SEQ ID NO 926
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
auggcugugg acaguacuc                                              19

<210> SEQ ID NO 927
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
gaguacuguc cacagccau                                              19

<210> SEQ ID NO 928
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
aguacucugc ucaaagaag                                              19

<210> SEQ ID NO 929
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 929
cuucuuugag cagaguacu                                                  19

<210> SEQ ID NO 930
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
caaagaaguc agaggccuc                                                  19

<210> SEQ ID NO 931
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
gaggccucug acuucuuug                                                  19

<210> SEQ ID NO 932
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
cagaggccuc accagggug                                                  19

<210> SEQ ID NO 933
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
cacccuggug aggccucug                                                  19

<210> SEQ ID NO 934
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
ccagggugug gacaucuug                                                  19
```

```
<210> SEQ ID NO 935
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
caagaugucc acacccugg                                                  19

<210> SEQ ID NO 936
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
acaucuugug cucugcugg                                                  19

<210> SEQ ID NO 937
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
ccagcagagc acaagaugu                                                  19

<210> SEQ ID NO 938
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
cugcuggauc uacugugua                                                  19

<210> SEQ ID NO 939
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
uacacaguag auccagcag                                                  19

<210> SEQ ID NO 940
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 940
cuguguacgc accauucac                                               19

<210> SEQ ID NO 941
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
gugaauggug cguacacag                                               19

<210> SEQ ID NO 942
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
ccauucacug gaaugauug                                               19

<210> SEQ ID NO 943
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
caaucauucc agugaaugg                                               19

<210> SEQ ID NO 944
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
aaugauugug ggccaggag                                               19

<210> SEQ ID NO 945
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
cuccuggccc acaaucauu                                               19

<210> SEQ ID NO 946
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
gggccaggag aaaccuuau                                             19

<210> SEQ ID NO 947
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
auaagguuuc uccuggccc                                             19

<210> SEQ ID NO 948
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
ccuuaucaaa acaagaaug                                             19

<210> SEQ ID NO 949
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949
cauucuuguu uugauaagg                                             19

<210> SEQ ID NO 950
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
caagaaugcu aucaauaau                                             19

<210> SEQ ID NO 951
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 951
auuauugaua gcauucuug                                             19
```

<210> SEQ ID NO 952
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
aucaauaaug guguucgaa                                                    19

<210> SEQ ID NO 953
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
uucgaacacc auuauugau                                                    19

<210> SEQ ID NO 954
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
guucgaauau cuggaagag                                                    19

<210> SEQ ID NO 955
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
cucuuccaga uauucgaac                                                    19

<210> SEQ ID NO 956
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
ucuggaagag guuuuugug                                                    19

<210> SEQ ID NO 957
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 957
cacaaaaacc ucuuccaga                                            19

<210> SEQ ID NO 958
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
uuuuuguguc aaaauguuc                                            19

<210> SEQ ID NO 959
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
gaacauuuug acacaaaaa                                            19

<210> SEQ ID NO 960
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
auguucuaca uuaagccaa                                            19

<210> SEQ ID NO 961
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
uuggcuuaau guagaacau                                            19

<210> SEQ ID NO 962
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
uaagccaauu aaguauaaa                                            19

<210> SEQ ID NO 963
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
uuuauacuua auuggcuua                                               19

<210> SEQ ID NO 964
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
aaguauaaag guccauuua                                               19

<210> SEQ ID NO 965
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
uaauaggacc uuuauacuu                                               19

<210> SEQ ID NO 966
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
ccuauuaaga agggagaaa                                               19

<210> SEQ ID NO 967
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
uuucucccuu cuuaauagg                                               19

<210> SEQ ID NO 968
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
```
agggagaaaa acuuggaac                                                    19

<210> SEQ ID NO 969
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
guuccaaguu uuucucccu                                                    19

<210> SEQ ID NO 970
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
cuuggaacuc uauugcccu                                                    19

<210> SEQ ID NO 971
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
agggcaauag aguuccaag                                                    19

<210> SEQ ID NO 972
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
uugcccuugc agaaaguuu                                                    19

<210> SEQ ID NO 973
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
aaacuuucug caagggcaa                                                    19

<210> SEQ ID NO 974
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 974
agaaaguuua uccuggcau                                            19

<210> SEQ ID NO 975
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
augccaggau aaacuuucu                                            19

<210> SEQ ID NO 976
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
ccuggcauac aaucgcaug                                            19

<210> SEQ ID NO 977
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
caugcgauug uaugccagg                                            19

<210> SEQ ID NO 978
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
aucgcaugug cacauugaa                                            19

<210> SEQ ID NO 979
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
uucaaugugc acaugcgau                                            19

<210> SEQ ID NO 980
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
cauugaaaac ugugacucg                                                       19

<210> SEQ ID NO 981
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
cgagucacag uuucaaug                                                        19

<210> SEQ ID NO 982
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
gugacucgag ugacccuac                                                       19

<210> SEQ ID NO 983
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
guagggucac ucgagucac                                                       19

<210> SEQ ID NO 984
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
ugacccuacu gcauaccug                                                       19

<210> SEQ ID NO 985
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
```

```
cagguaugca guaggguca                                          19

<210> SEQ ID NO 986
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
cauaccugua aaucgaagg                                          19

<210> SEQ ID NO 987
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
ccuucgauuu acagguaug                                          19

<210> SEQ ID NO 988
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
uggucagauc uucaaaaua                                          19

<210> SEQ ID NO 989
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
uauuuugaag aucugacca                                          19

<210> SEQ ID NO 990
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
cuucaaaaua aaaagucau                                          19

<210> SEQ ID NO 991
<211> LENGTH: 19
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 991
augacuuuuu auuuugaag                                                     19

<210> SEQ ID NO 992
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 992
aagucaucuu aaaaaccug                                                     19

<210> SEQ ID NO 993
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
cagguuuuua agaugacuu                                                     19

<210> SEQ ID NO 994
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
aaaaccugga ugcauaccc                                                     19

<210> SEQ ID NO 995
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
ggguaugcau ccagguuuu                                                     19

<210> SEQ ID NO 996
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
gcauacccuu cucuucaag                                                     19
```

```
<210> SEQ ID NO 997
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
cuugaagaga aggguaugc                                                    19

<210> SEQ ID NO 998
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
cuucaagaaa uuuguguuc                                                    19

<210> SEQ ID NO 999
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
gaacacaaau uucuugaag                                                    19

<210> SEQ ID NO 1000
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
uuguguucac aaaggaaaa                                                    19

<210> SEQ ID NO 1001
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
uuuuccuuug ugaacacaa                                                    19

<210> SEQ ID NO 1002
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1002
aaggaaaaau gcaugaagg                                                         19

<210> SEQ ID NO 1003
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
ccuucaugca uuuuccuu                                                          19

<210> SEQ ID NO 1004
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
ugcaugaagg gauggauac                                                         19

<210> SEQ ID NO 1005
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
guauccaucc cuucaugca                                                         19

<210> SEQ ID NO 1006
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
uggauacccc auuuuccau                                                         19

<210> SEQ ID NO 1007
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
auggaaaaug ggguaucca                                                         19

<210> SEQ ID NO 1008
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 1008
uuuccaugac augauuauu                                                       19

<210> SEQ ID NO 1009
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
aauaaucaug ucauggaaa                                                       19

<210> SEQ ID NO 1010
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
caugauuauu acacauugc                                                       19

<210> SEQ ID NO 1011
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
gcaaugugua auaaucaug                                                       19

<210> SEQ ID NO 1012
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
cacauugcau gccuguauc                                                       19

<210> SEQ ID NO 1013
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1013
gauacaggca ugcaaugug                                                       19
```

```
<210> SEQ ID NO 1014
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
ccuguaucaa aacaucuca                                                    19

<210> SEQ ID NO 1015
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
ugagauguuu ugauacagg                                                    19

<210> SEQ ID NO 1016
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
caucucacgu accucauaa                                                    19

<210> SEQ ID NO 1017
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
uuaugaggua cgugagaug                                                    19

<210> SEQ ID NO 1018
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
ccucauaaac auauacacc                                                    19

<210> SEQ ID NO 1019
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1019
gguguauaug uuuaugagg                                                    19

<210> SEQ ID NO 1020
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
auacaccuau guacccaca                                                    19

<210> SEQ ID NO 1021
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1021
uguggguaca uagguguau                                                    19

<210> SEQ ID NO 1022
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
guacccacaa aaauuuuuu                                                    19

<210> SEQ ID NO 1023
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
aaaaaauuuu ugugggguac                                                   19

<210> SEQ ID NO 1024
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
uaaaaaaagg aaauuugag                                                    19

<210> SEQ ID NO 1025
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
cucaaauuuc cuuuuuua                                                 19

<210> SEQ ID NO 1026
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
aauuugaguu uaaauagaa                                                19

<210> SEQ ID NO 1027
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
uucuauuuaa acucaaauu                                                19

<210> SEQ ID NO 1028
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
auagaaacau gauaaaugc                                                19

<210> SEQ ID NO 1029
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
gcauuuauca uguuucuau                                                19

<210> SEQ ID NO 1030
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1030
gauaaaugca agaaagaaa                                                19
```

<210> SEQ ID NO 1031
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1031
uuucuuucuu gcauuuauc                                                19

<210> SEQ ID NO 1032
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1032
gaaagaaaac auuuugauu                                                19

<210> SEQ ID NO 1033
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1033
aaucaaaaug uuucuuuc                                                 19

<210> SEQ ID NO 1034
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1034
acucauuguc acucugaug                                                19

<210> SEQ ID NO 1035
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 1035
caucagagug acaaugagu                                                19

<210> SEQ ID NO 1036
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

```
Synthetic oligonucleotide"

<400> SEQUENCE: 1036
cucugauguu caugugaac                                                19

<210> SEQ ID NO 1037
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
guucacauga acaucagag                                                19

<210> SEQ ID NO 1038
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
caugugaacu gguugcuuc                                                19

<210> SEQ ID NO 1039
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
gaagcaacca guucacaug                                                19

<210> SEQ ID NO 1040
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
guugcuucgg gcucuuuga                                                19

<210> SEQ ID NO 1041
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
ucaaagagcc cgaagcaac                                                19

<210> SEQ ID NO 1042
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
ucuuugaucu gucaccuau                                                  19

<210> SEQ ID NO 1043
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
auaggugaca gaucaaaga                                                  19

<210> SEQ ID NO 1044
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
caccuaugga aucugagug                                                  19

<210> SEQ ID NO 1045
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
cacucagauu ccauaggug                                                  19

<210> SEQ ID NO 1046
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046 aaucgagug guuuuauuu                                                   19

<210> SEQ ID NO 1047
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1047
aaauaaaacc acucagauu                                                    19

<210> SEQ ID NO 1048
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
uuuuuuagau uucucaguc                                                    19

<210> SEQ ID NO 1049
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1049
gacugagaaa ucuaaaaaa                                                    19

<210> SEQ ID NO 1050
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050
cucaguccca aagaucuaa                                                    19

<210> SEQ ID NO 1051
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1051
uuagaucuuu gggacugag                                                    19

<210> SEQ ID NO 1052
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1052
gaucuaagau aaauaaaca                                                    19

<210> SEQ ID NO 1053
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1053
uguuuauuua ucuuagauc                                                    19
```

COMPOSITIONS AND METHODS FOR INHIBITING EXPRESSION OF THE LECT2 GENE

CROSS-REFERENCE TO RELATED APPLICATIONS

This application is the U.S. National Phase Application under 35 U.S.C. § 371 of International Application No. PCT/US2014/058624, filed Oct. 1, 2014, which claims the benefit of U.S. Provisional Application No. 61/885,693, filed Oct. 2, 2013 and U.S. Provisional Application No. 62/035,819, filed Aug. 11, 2014. The contents of the aforesaid applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 29, 2014, is named A2038-7200WO_SL.txt and is 294,414 bytes in size.

FIELD OF THE INVENTION

The invention relates to the specific inhibition of the expression of the LECT2 gene.

BACKGROUND OF THE INVENTION

Amyloidosis is a group of diseases characterized by deposition of insoluble fibrous protein aggregates, called amyloids, in organs or tissues. Amyloids can form from mutant or wild type proteins. One system of nomenclature for amyloid diseases uses an abbreviation for the protein that forms amyloid deposits, preceded by the letter "A." Thus, for example, ALECT2 is the abbreviation for an amyloidosis involving deposit of amyloids formed from leukocyte cell derived chemotactic factor-2 (ALECT2).

LECT2 amyloidosis (ALECT2) is one of the most recently discovered types of amyloidosis. LECT2 amyloidosis has been observed in individuals with renal or hepatic amyloidosis. This form of amyloidosis can present with nephrotic syndrome or with liver involvement (e.g., hepatitis, e.g., chronic hepatitis). It may be particularly prevalent in Mexican Americans and/or individuals who are homozygous for the G allele encoding valine at position 40 in the mature LECT2 protein (or at position 58 in the unprocessed protein). Treatments for LECT2 amyloidosis are limited, and new treatments are needed.

SUMMARY OF THE INVENTION

The present invention describes methods and iRNA compositions for modulating the expression of a LECT2 gene. In certain embodiments, expression of a LECT2 gene is reduced or inhibited using a LECT2-specific iRNA. Such inhibition can be useful in treating disorders related to LECT2 expression, such as amyloidosis, e.g. a LECT2 amyloidosis (ALECT2).

Accordingly, described herein are compositions and methods that effect the RNA-induced silencing complex (RISC)-mediated cleavage of RNA transcripts of the LECT2 gene, such as in a cell or in a subject (e.g., in a mammal, such as a human subject). Also described are compositions and methods for treating a disorder related to expression of a LECT2 gene, such as a LECT2 amyloidosis.

In some embodiments, the LECT2 amyloidosis is a renal amyloidosis.

In some embodiments, the LECT2 amyloidosis involves amyloid deposition in the kidney.

In some embodiments, LECT2 amyloidosis is associated with renal disease (e.g., nephrotic syndrome). In some embodiments, the amyloidosis is associated with proteinuria. In some embodiments, proteinuria is absent.

In some embodiments, the LECT2 amyloidosis is a hepatic amyloidosis. In some embodiments, the the LECT2 amyloidosis involves amyloid deposition in the liver.

In some embodiments, the LECT2 amyloidosis is associated with inflammation in the liver (e.g., hepatitis, e.g., chronic hepatitis).

In some embodiments, the subject is of Mexican descent (e.g., a Mexican American).

In embodiments, the subject carries the G allele of the LECT2 gene that encodes valine at position 40 in the mature protein (or amino acid 58 in the unprocessed protein). In embodiments, the subject is homozygous for the G allele (G/G genotype). In embodiments, a LECT2 protein expressed in the subject has valine at position 40 in the mature protein (or at amino acid 58 in the unprocessed protein).

In some embodiments, the methods described herein are effective to inhibit amyloid deposition (e.g., by preventing amyloid deposition or reducing amyloid deposition, e.g., by reducing size, number, or extent of amyloid deposits) or symptoms associated with amyloid deposition.

As used herein, the term "iRNA," "RNAi", "iRNA agent," "RNAi agent," or "iRNA molecule," refers to an agent that contains RNA as that term is defined herein, and which mediates the targeted cleavage of an RNA transcript, e.g., via an RNA-induced silencing complex (RISC) pathway. In one embodiment, an iRNA as described herein inhibits LECT2 expression in a cell or mammal.

The iRNAs (e.g., dsRNAs) included in the compositions featured herein include an RNA strand (the antisense strand) having a region, e.g., a region that is 30 nucleotides or less, generally 19-24 nucleotides in length, that is substantially complementary to at least part of an mRNA transcript of a LECT2 gene (e.g., a mouse or human LECT2 gene) (also referred to herein as a "LECT2-specific iRNA"). In embodiments, the LECT2 mRNA transcript is a human LECT2 mRNA transcript, e.g., SEQ ID NO: 1. In embodiments, the LECT2 mRNA transcript has a A to G substitution at nucleotide position 373 of SEQ ID NO: 1. In embodiments, the mRNA transcript encodes valine at position 40 in the mature LECT2 protein (or amino acid 58 in the unprocessed protein). In embodiments, the mRNA transcript encodes isoleucine at position 40 in the mature LECT2 protein (or amino acid 58 in the unprocessed protein).

In embodiments, the iRNA (e.g, dsRNA) described herein comprises an antisense strand having a region that is substantially complementary to a region of a human LECT2 mRNA. In embodiments, the human LECT2 mRNA has the sequence of NM_002302.2 (SEQ ID NO: 1). In embodiments, the human LECT2 mRNA has a A to G substitution at nucleotide position 373 of SEQ ID NO: 1.

In other embodiments, an iRNA encompasses a dsRNA having an RNA strand (the antisense strand) having a region that is substantially complementary to a portion of a LECT2 mRNA. In one embodiment, the iRNA encompasses a dsRNA having an RNA strand (the antisense strand) having a region that is substantially complementary to a portion of a LECT2 mRNA, e.g., a human LECT2 mRNA (e.g., a human LECT2 mRNA as provided in NM_002302.2 (SEQ ID NO: 1) or having a A to G substitution at nucleotide position 373 of SEQ ID NO: 1).

In one embodiment, an iRNA for inhibiting expression of a LECT2 gene includes at least two sequences that are complementary to each other. The iRNA includes a sense strand having a first sequence and an antisense strand having a second sequence. The antisense strand includes a nucleotide sequence that is substantially complementary to at least part of an mRNA encoding a LECT2 transcript, and the region of complementarity is 30 nucleotides or less, and at least 15 nucleotides in length. Generally, the iRNA is 19 to 24 nucleotides in length.

In some embodiments, the iRNA is 19-21 nucleotides in length. In some embodiments, the iRNA is 19-21 nucleotides in length and is in a lipid formulation, e.g. a lipid nanoparticle (LNP) formulation (e.g., an LNP11 formulation). In one embodiment, the iRNA targeting LECT2 is formulated in a stable nucleic acid lipid particle (SNALP).

In some embodiments, the iRNA is 21-23 nucleotides in length. In some embodiments, the iRNA is 21-23 nucleotides in length and is in the form of a conjugate, e.g., conjugated to one or more GalNAc derivatives as described herein.

In some embodiments the iRNA is from about 15 to about 25 nucleotides in length, and in other embodiments the iRNA is from about 25 to about 30 nucleotides in length. An iRNA targeting LECT2, upon contact with a cell expressing LECT2, inhibits the expression of a LECT2 gene (e.g., by at least 10%, at least 20%, at least 25%, at least 30%, at least 35% or at least 40%, at least 50%, at least 60%, at least 70%, or at least 80%) when assayed by a method known in the art or as described herein.

In one embodiment, an iRNA (e.g., a dsRNA) featured herein comprises or consists of a first sequence of a dsRNA that is selected from the group consisting of the sense sequences of Tables 2-3, 5-6 and 9-10 and a second sequence that is selected from the group consisting of the corresponding antisense sequences of Tables 2-3, 5-6 and 9-10.

In embodiments, an iRNA (e.g., dsRNA) featured herein comprises or consists of a sense and/or antisense sequence selected from those provided in Table 2-3, 5-6 and 9-10.

The iRNA molecules featured herein can include naturally occurring nucleotides or can include at least one modified nucleotide, including, but not limited to a 2'-O-methyl modified nucleotide, a nucleotide having a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an acyclic nucleotide, an abasic nucleotide, 2'-amino-modified nucleotide, 2'-alkyl-modified nucleotide, morpholino nucleotide, a phosphoramidate, and a non-natural base comprising nucleotide. Such a modified sequence can be based, e.g., on a first sequence of said iRNA selected from the group consisting of the sense sequences of Tables 2-3, 5-6 and 9-10, and a second sequence selected from the group consisting of the corresponding antisense sequences of Tables 2-3, 5-6 and 9-10.

In one embodiment, an iRNA as described herein targets a wildtype LECT2 RNA transcript variant, and in another embodiment, the iRNA targets a mutant transcript (e.g., a LECT2 RNA carrying an allelic variant). For example, an iRNA featured in the invention can target a polymorphic variant, such as a single nucleotide polymorphism (SNP), of LECT2.

In some embodiments, the iRNA (e.g., dsRNA) targets (e.g., reduces) mRNA that encodes valine at position 40 in the mature LECT2 protein (or amino acid 58 in the unprocessed protein). In some embodiments, the iRNA (e.g., dsRNA) targets (e.g., reduces) mRNA that encodes isoleucine at position 40 in the mature LECT2 protein (or amino acid 58 in the unprocessed protein). In another embodiment, the iRNA (e.g., dsRNA) targets (e.g., reduces) both mRNA that encodes valine and mRNA that encodes isoleucine at position 40 in the mature LECT2 protein (or amino acid 58 in the unprocessed protein).

In another embodiment, the iRNA targets both a wildtype and a mutant LECT2 transcript. In yet another embodiment, the iRNA targets a particular transcript variant of LECT2. In yet another embodiment, the iRNA agent targets multiple transcript variants.

In one embodiment, an iRNA featured in the invention targets a non-coding region of a LECT2 RNA transcript, such as the 5' or 3' untranslated region of a transcript.

In some embodiments, an iRNA as described herein is in the form of a conjugate, e.g., a carbohydrate conjugate, which may serve as a targeting moiety and/or ligand, as described herein. In one embodiment, the conjugate is attached to the 3' end of the sense strand of the dsRNA. In some embodiments, the conjugate is attached via a linker, e.g., via a bivalent or trivalent branched linker.

In some embodiments, the conjugate comprises one or more N-acetylgalactosamine (GalNAc) derivatives. Such a conjugate is also referred to herein as a GalNAc conjugate. In some embodiments, the conjugate targets the RNAi agent (e.g., dsRNA) to a particular cell, e.g., a liver cell, e.g., a hepatocyte. The GalNAc derivatives can be attached via a linker, e.g., a bivalent or trivalent branched linker. In particular embodiments, the conjugate is

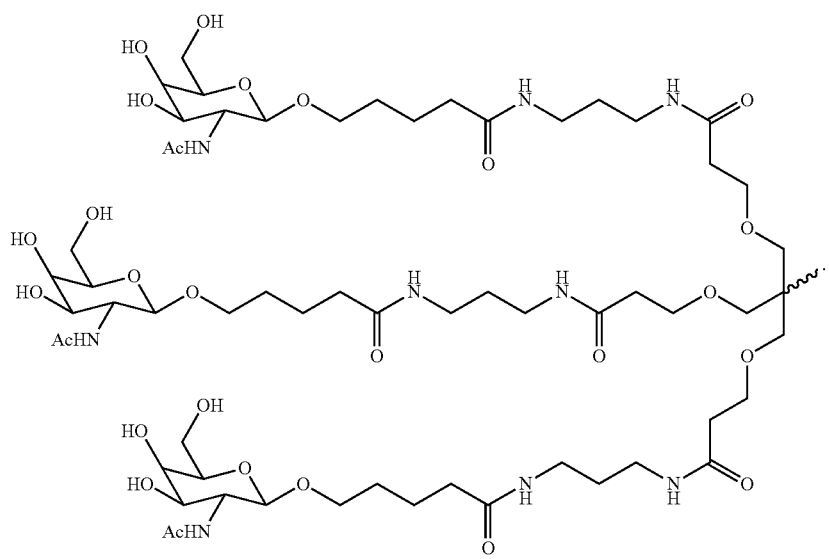 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
In some embodiments, the RNAi agent is attached to the carbohydrate conjugate via a linker, e.g., a linker as shown in the following schematic, wherein X is O or S
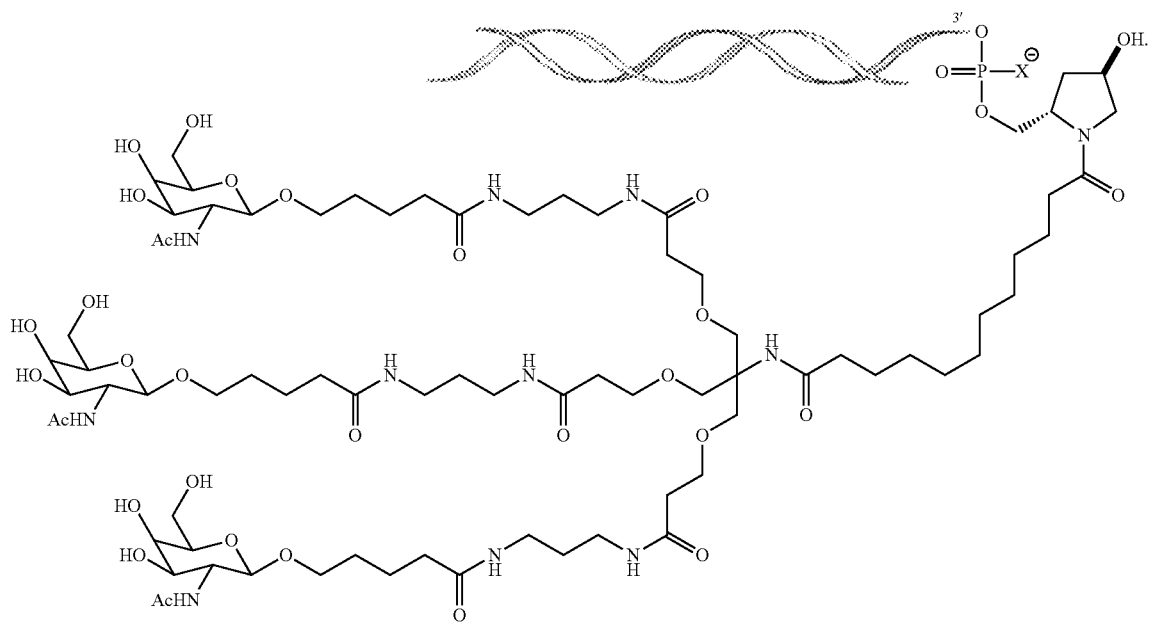
In some embodiments, X is O. In some embodiments, X is S.
In some embodiments, the RNAi agent is conjugated to L96 as defined in Table 1 and shown below

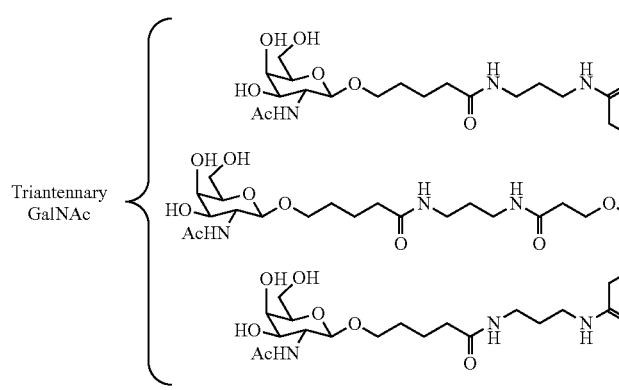
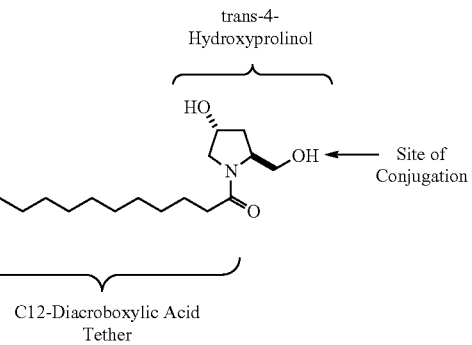

In some embodiments, the RNAi agent is conjugated to a ligand that targets the RNAi (e.g., dsRNA) to a desired organ (e.g., the liver) or to a particular cell type (e.g., hepatocytes). In embodiments, the RNAi agent is conjugated to a ligand (e.g., a GalNAc ligand, e.g., L96) that targets the RNAi agent (e.g., dsRNA) to the liver.

In an aspect provided herein is a pharmaceutical composition for inhibiting the expression of a LECT2 gene in an organism, generally a human subject. The composition typically includes one or more of the iRNAs described herein and a pharmaceutically acceptable carrier or delivery vehicle. In one embodiment, the composition is used for treating a disorder related to LECT2 expression, e.g., amyloidosis, e.g., LECT2 amyloidosis.

In one aspect, an iRNA provided herein is a double-stranded ribonucleic acid (dsRNA) for inhibiting expression of LECT2, wherein said dsRNA comprises a sense strand and an antisense strand 15-30 base pairs in length and the antisense strand is complementary to at least 15 contiguous nucleotides of SEQ ID NO: 1.

In a further aspect, an iRNA provided herein is a double stranded RNAi (dsRNA) comprising a sense strand complementary to an antisense strand, wherein said antisense strand comprises a region of complementarity to a LECT2 RNA transcript, wherein each strand has about 14 to about 30 nucleotides, wherein said double stranded RNAi agent is represented by formula (III):

sense: 5' $n_p$-$N_a$—$(XXX)_i$—$N_b$—YYY—$N_b$—$(ZZZ)_j$—$N_a$-$n_q$ 3' antisense: 3' $n_p'$-$N_a'$—$(X'X'X')_k$—$N_b'$—Y'Y'Y'—$N_b'$—$(Z'Z'Z')_l$—$N_a'$-$n_q'$ 5'   (III)

wherein:

j, k, and l are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$ independently represents an overhang nucleotide; XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b'$ differ from the modification on Y'.

In embodiments, the sense strand is conjugated to at least one ligand.

In embodiments, i is 1; j is 1; or both i and j are 1.

In embodiments, k is 1; l is 1; or both k and l are 1.

In embodiments, XXX is complementary to X'X'X', YYY is complementary to Y'Y'Y', and ZZZ is complementary to Z'Z'Z'.

In embodiments, the Y'Y'Y' motif occurs at the 11, 12 and 13 positions of the antisense strand from the 5'-end.

In embodiments, the Y' is 2'-O-methyl.

In embodiments, the duplex region is 15-30 nucleotide pairs in length.

In embodiments, the duplex region is 17-23 nucleotide pairs in length.

In embodiments, the duplex region is 19-21 nucleotide pairs in length.

In embodiments, the duplex region is 21-23 nucleotide pairs in length.

In embodiments, the modifications on the nucleotides are selected from the group consisting of a locked nucleic acid (LNA), an acyclic nucleotide, a hexitol or hexose nucleic acid (HNA), a cyclohexene nucleic acid (CeNA), 2'-methoxyethyl, 2'-O-alkyl, 2'-O-allyl, 2'-C-allyl, 2'-fluoro, 2'-deoxy, 2'-hydroxyl, and any combination thereof.

In embodiments, the modifications on the nucleotides are 2'-O-methyl, 2'-fluoro or both.

In embodiments, the ligand comprises a carbohydrate.

In embodiments, the ligand is attached via a linker.

In embodiments, the linker is a bivalent or trivalent branched linker.

In embodiments, the ligand is

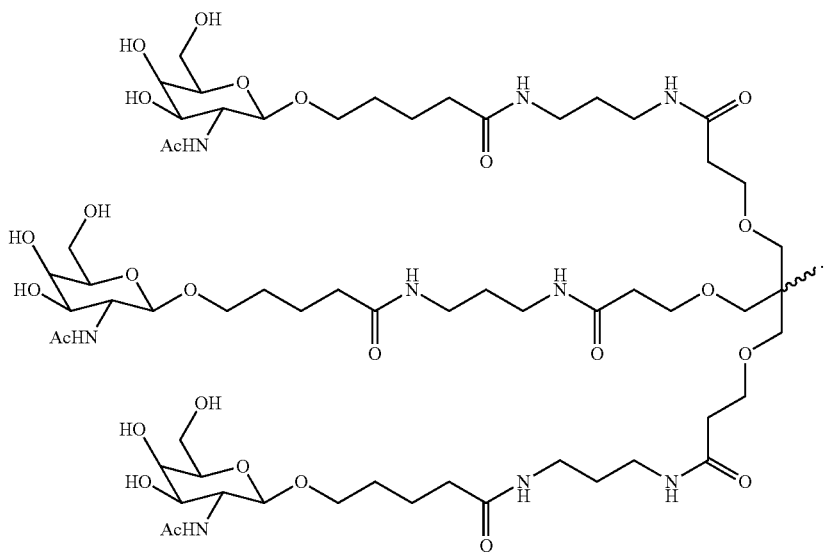 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In embodiments, the ligand and linker are as shown in Formula XXIV:

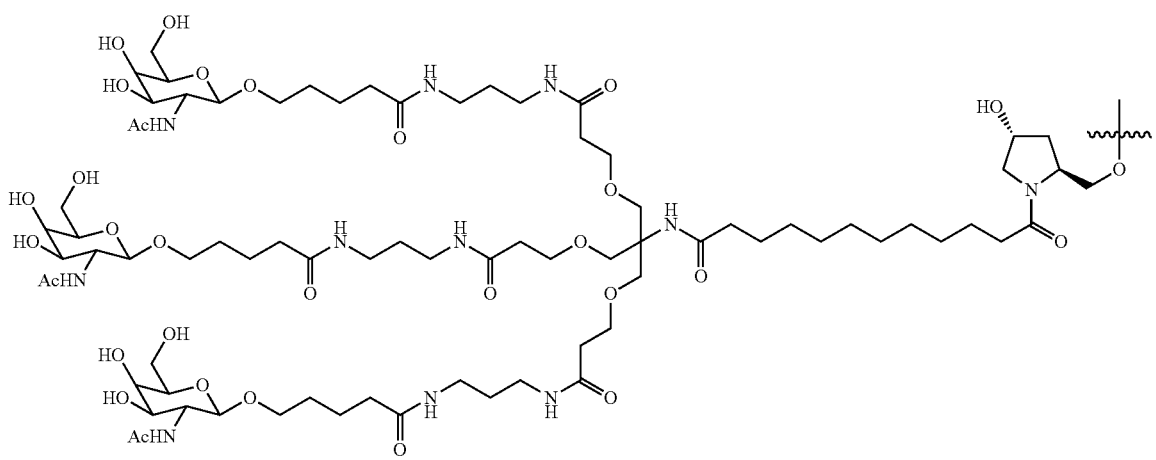 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In embodiments, the ligand is attached to the 3' end of the sense strand.

In embodiments, the dsRNA has (e.g., comprises) a nucleotide sequence (e.g., a sense and/or antisense sequence) selected from the group of sequences provided in Tables 2-3, 5-6 and 9-10.

In a further aspect, an iRNA provided herein is a double-stranded ribonucleic acid (dsRNA) for inhibiting expression of LECT2, wherein said dsRNA comprises a sense strand and an antisense strand, the antisense strand comprising a region of complementarity to a LECT2 RNA transcript, which antisense strand comprises at least 15 contiguous nucleotides differing by no more than 3 nucleotides from one of the antisense sequences listed in any one of Tables 2-3, 5-6 and 9-10.

In some embodiments, the dsRNA comprises at least one modified nucleotide.

In some embodiments, at least one of the modified nucleotides is chosen from the group consisting of: a 2'-O-methyl modified nucleotide, a nucleotide comprising a 5'-phosphorothioate group, and a terminal nucleotide linked to a cholesteryl derivative or dodecanoic acid bisdecylamide group.

In some embodiments, the modified nucleotide is chosen from the group consisting of: a 2'-deoxy-2'-fluoro modified nucleotide, a 2'-deoxy-modified nucleotide, a locked nucleotide, an acyclic nucleotide, an abasic nucleotide, 2'-amino-modified nucleotide, 2'-alkyl-modified nucleotide, morpholino nucleotide, a phosphoramidate, and a non-natural base comprising nucleotide.

In some embodiments, the region of complementarity is at least 17 nucleotides in length.

In some embodiments, the region of complementarity is between 19 and 21 nucleotides in length.

In some embodiments, the region of complementarity is 19 nucleotides in length.

In some embodiments, each strand is no more than 30 nucleotides in length.

In some embodiments, at least one strand comprises a 3' overhang of at least 1 nucleotide.

In some embodiments, at least one strand comprises a 3' overhang of at least 2 nucleotides.

In some embodiments, an iRNA (e.g., a dsRNA) described herein further comprises a ligand.

In some embodiments, the ligand is a GalNAc ligand.

In some embodiments, the ligand targets the iRNA (e.g., the dsRNA) to the liver (e.g., to hepatocytes).

In some embodiments, the ligand is conjugated to the 3' end of the sense strand of the dsRNA.

In some embodiments, the region of complementarity consists of an antisense sequence selected from the antisense sequences provided in Tables 2-3, 5-6 and 9-10.

In embodiments, the region of complementarity consists of an antisense sequence selected from a duplex disclosed herein, wherein the duplex suppresses LECT2 mRNA or protein expression by at least 20%, 30%, 40%, 50%, 60%, 70%, 80%, 85% or 90%.

In some embodiments, the dsRNA comprises a sense strand comprising or consisting of a sense strand sequence selected from Table 2, 3, 5, 6, 9 or 10, and an antisense strand comprising or consisting of an antisense sequence selected from Table 2, 3, 5, 6, 9 or 10. In embodiments, the dsRNA comprises or consists of a pair of corresponding sense and antisense sequences selected from those of the duplexes disclosed in Tables 2-3 and 5-11. In certain embodiments, the dsRNA comprises or consists of a pair of corresponding sense and antisense sequences selected from those of the duplexes disclosed in Table 8.

In one aspect, the invention provides a cell containing at least one iRNA (e.g., dsRNAs) disclosed herein. The cell is typically a mammalian cell, such as a human cell. In embodiments, the cell is a liver cell (e.g., a hepatocyte).

In an aspect provided herein is a pharmaceutical composition for inhibiting expression of a LECT2 gene, the composition comprising an iRNA (e.g., a dsRNA) described herein.

In embodiments of the pharmaceutical compositions described herein, the iRNA (e.g., dsRNA) is administered in an unbuffered solution. In embodiments, the unbuffered solution is saline or water.

In embodiments of the pharmaceutical compositions described herein, the iRNA (e.g., dsRNA is administered with a buffer solution. In embodiments, the buffer solution comprises acetate, citrate, prolamine, carbonate, or phosphate or any combination thereof. In embodiments, the buffer solution is phosphate buffered saline (PBS).

In embodiments of the pharmaceutical compositions described herein, the iRNA (e.g., dsRNA) is targeted to the liver (e.g., to hepatocytes).

In embodiments of the pharmaceutical compositions described herein, the composition is administered intravenously.

In embodiments of the pharmaceutical compositions described herein, the composition is administered subcutaneously.

In embodiments, a pharmaceutical composition comprises an iRNA (e.g., a dsRNA) described herein that comprises a ligand (e.g., a GalNAc ligand) that targets the iRNA (e.g., dsRNA) to a liver cell, e.g., a hepatocyte.

In embodiments, a pharmaceutical composition comprises an iRNA (e.g., a dsRNA) described herein that comprises a ligand (e.g., a GalNAc ligand), and the pharmaceutical composition is administered subcutaneously. In embodiments, the ligand targets the iRNA (e.g., dsRNA) to a liver cell, e.g., a hepatocyte.

In certain embodiments, a pharmaceutical composition, e.g., a composition described herein, includes a lipid formulation. In some embodiments, the RNAi agent is in a LNP formulation, e.g., a MC3 formulation. In some embodiments, the LNP formulation targets the RNAi agent to a particular cell, e.g., a liver cell (e.g., a hepatocyte). In embodiments, the lipid formulation is a LNP11 formulation. In embodiments, the composition is administered intravenously.

In another embodiment, the pharmaceutical composition is formulated for administration according to a dosage regimen described herein, e.g., not more than once every four weeks, not more than once every three weeks, not more than once every two weeks, or not more than once every week. In another embodiment, the administration of the pharmaceutical composition can be maintained for a month or longer, e.g., one, two, three, or six months, or one year or longer.

In another embodiment, a composition containing an iRNA featured in the invention, e.g., a dsRNA targeting LECT2, is administered in conjunction with a second therapy for a disorder related to LECT2 expression (e.g., a LECT2 amyloidosis). An iRNA or composition comprising an iRNA provided herein can be administered before, after, or concurrent with a second therapy. In embodiments, the iRNA is administered before the second therapy. In embodiments, the iRNA is administered after the second therapy. In embodiments, the iRNA is administered concurrent with the second therapy.

In some embodiments, the second therapy is a non-iRNA therapeutic agent that is effective to treat the disorder or symptoms of the disorder.

In some embodiments, the disorder to be treated by the compositions or methods disclosed herein is a LECT2 amyloidosis that affects kidney function, e.g., through amyloid deposition in the kidney. In some such embodiments, the iRNA is administered in conjunction with a therapy that supports kidney function (e.g., dialysis). In embodiments, the iRNA is administered in conjunction with a diuretic, an ACE (angiotensin converting enzyme) inhibitor, an angiotensin receptor blocker, and/or dialysis, e.g., to support or manage kidney function.

In some embodiments, the disorder to be treated by the compositions or methods disclosed herein is a LECT2 amyloidosis involving amyloid deposits in the liver. In some such embodiments, the iRNA is administered in conjunction with a therapy that supports liver function.

In some embodiments, the disorder to be treated by the compositions or methods disclosed herein is a LECT2 amyloidosis, and the iRNA is administered in conjunction with removal of all or part of the organ(s) affected by the amyloidosis (e.g., resection of all or part of kidney or liver tissue affected by the amyloidosis). The removal is optionally conducted in conjunction with a replacement of all or part of the organ removed (e.g., in conjunction with a kidney or liver organ transplant).

In an aspect provided herein is a method of inhibiting LECT2 expression in a cell, the method comprising: (a) introducing into the cell an iRNA (e.g., a dsRNA) described herein and (b) maintaining the cell of step (a) for a time sufficient to obtain degradation of the mRNA transcript of a LECT2 gene, thereby inhibiting expression of the LECT2 gene in the cell.

In an aspect provided herein is a method for reducing or inhibiting the expression of a LECT2 gene in a cell (e.g., a liver cell, e.g., a hepatocyte). The method includes contacting the cell with a dsRNA as described herein, thereby inhibiting expression of a LECT2 gene. "Contacting," as used herein, includes directly contacting a cell, as well as indirectly contacting a cell. For example, a cell within a subject (e.g., a liver cell) may be contacted when a composition comprising an RNAi is administered (e.g., intravenously or subcutaneously) to the subject.

In embodiments, the method includes
(a) introducing into the cell a double-stranded ribonucleic acid (dsRNA), wherein the dsRNA includes at least two sequences that are complementary to each other. The dsRNA has a sense strand having a first sequence and an antisense strand having a second sequence; the antisense strand has a region of complementarity that is substantially complementary to at least a part of an mRNA encoding LECT2, and where the region of complementarity is 30 nucleotides or less, e.g., 15-30 nucleotides in length, and generally 19-24 nucleotides in length, and where the dsRNA upon contact with a cell expressing LECT2, inhibits expression of a LECT2 gene by at least 10%, e.g., at least 20%, at least 30%, at least 40% or more; and
(b) maintaining the cell of step (a) for a time sufficient to obtain degradation of the mRNA transcript of the LECT2 gene, thereby reducing or inhibiting expression of a LECT2 gene in the cell.

In embodiments of the foregoing methods of inhibiting LECT2 expression in a cell, the cell is treated ex vivo, in vitro, or in vivo. In embodiments, the cell is a hepatocyte.

In embodiments, the cell is present in a subject in need of treatment, prevention and/or management of a disorder related to LECT2 expression.

In embodiments, the disorder is a LECT2 amyloidosis, as described herein.

In embodiments, the expression of LECT2 is inhibited by at least 30%.

In embodiments, the iRNA (e.g., dsRNA) has an $IC_{50}$ in the range of 0.0005-1 nM, e.g., between 0.001 and 0.2 nM, between 0.002 and 0.1 nM, between 0.005 and 0.075 nM, or between 0.01 and 0.05 nM. In embodiments, the iRNA (e.g., dsRNA) has an $IC_{50}$ equal to or less than 0.02 nM, e.g., between 0.0005 and 0.02 nM, between 0.001 and 0.02 nM, between 0.005 and 0.02 nM, or between 0.01 and 0.02 nM. In embodiments, the iRNA (e.g., dsRNA) has an $IC_{50}$ in the range of 0.01-1 nM.

In embodiments, the cell (e.g., the hepatocyte) is a mammalian cell (e.g., a human, non-human primate, or rodent cell).

In one embodiment, the subject is a mammal (e.g., a human) having a LECT2 amyloidosis.

In one embodiment, the dsRNA introduced reduces or inhibits expression of a LECT2 gene in the cell.

In one embodiment, the dsRNA inhibits expression of a LECT2 gene, or inhibits amyloid deposition (e.g., by preventing amyloid deposition or reducing amyloid deposition, e.g., by reducing size, number, or extent of amyloid deposits). The inhibition optionally involves an inhibition of at least 5%, 10%, 15%, 20%, 25%, 30%, 35%, 40%, 45%, 50% or more compared to a reference, (e.g., a control that is untreated or treated with a non-targeting dsRNA (e.g., a dsRNA that does not target LECT2)).

In other aspects, the disclosure provides methods for treating pathological processes related to LECT2 expression (e.g., amyloid deposition). In one embodiment, the method includes administering to a subject, e.g., a patient in need of such treatment, an effective (e.g., a therapeutically or prophylactically effective) amount of a dsRNA provided herein.

In an aspect provided herein is a method of treating and/or preventing a disorder related to LECT2 expression (e.g., a LECT2 amyloidosis) comprising administering to a subject in need of such treatment a therapeutically effective amount of an iRNA (e.g., a dsRNA) described herein, or a composition comprising an iRNA (e.g., a dsRNA) described herein.

In an aspect provided herein is a method of treating a disorder related to LECT2 expression (e.g., LECT2 amyloidosis) comprising administering to a subject in need of such treatment a double-stranded ribonucleic acid (dsRNA), wherein said dsRNA comprises a sense strand and an antisense strand 15-30 base pairs in length and the antisense strand is complementary to at least 15 contiguous nucleotides of a LECT2 mRNA transcript, e.g., a human LECT2 mRNA transcript, e.g., SEQ ID NO: 1 or a nucleotide sequence having a A to G substitution at nucleotide position 373 of SEQ ID NO: 1. In one embodiment, the iRNA (e.g., dsRNA) targets mRNA that encodes valine at position 40 in the mature LECT2 protein (or amino acid 58 in the unprocessed protein).

In one embodiment provided herein is a method of treating a subject having a LECT2 amyloidosis, the method comprising administering to the subject a double-stranded ribonucleic acid (dsRNA), wherein said dsRNA comprises a sense strand and an antisense strand 15-30 base pairs in length and the antisense strand is complementary to at least 15 contiguous nucleotides of a LECT2 mRNA transcript, e.g., a human LECT2 mRNA transcript, e.g., SEQ ID NO: 1 or a nucleotide sequence having a A to G substitution at nucleotide position 373 of SEQ ID NO: 1. In one embodiment, the iRNA (e.g., dsRNA) targets mRNA that encodes valine at position 40 in the mature LECT2 protein (or amino acid 58 in the unprocessed protein).

In some embodiments, administration of the iRNA targeting LECT2 alleviates or relieves the severity of at least one symptom of a disorder related to LECT2 expression in the patient.

In one embodiment, subject has a LECT2 amyloidosis. In another embodiment, the subject is at risk for developing a LECT2 amyloidosis.

In embodiments, the iRNA (e.g., dsRNA) is formulated as an LNP formulation.

In embodiments, the iRNA (e.g., dsRNA) is in the form of a GalNAc conjugate.

In embodiments, the iRNA (e.g., dsRNA) is administered at a dose of 0.05-50 mg/kg.

In embodiments, the iRNA (e.g., dsRNA) is administered at a concentration of 0.01 mg/kg-5 mg/kg bodyweight of the subject.

In embodiments, the iRNA (e.g., dsRNA) is formulated as an LNP formulation and is administered at a dose of 0.05-5 mg/kg. In embodiments, the iRNA (e.g., dsRNA) is formulated as an LNP formulation and is administered at a dose of 0.1 to 0.5 mg/kg.

In embodiments, the iRNA (e.g., dsRNA) is in the form of a GalNAc conjugate and is administered at a dose of 0.5-50 mg/kg. In embodiments, the iRNA (e.g., dsRNA) is in the form of a GalNAc conjugate and is administered at a dose of 1 to 10 mg/kg.

In embodiments, the method inhibits expression of a LECT2 gene, or inhibits amyloid deposition (e.g., by preventing amyloid deposition or reducing amyloid deposition, e.g., by reducing size, number, or extent of amyloid deposits). The inhibition optionally involves an inhibition of at least 5%, 10%, 15%, 20%, 25%, 30%, 35%, 40%, 45%, 50%, 55%, 60%, 65%, 70%, 75%, 80%, 85%, or 90% compared to a reference (e.g., a control that is untreated or treated with a non-targeting dsRNA (e.g., a dsRNA that does not target LECT2)).

In embodiments, the iRNA (e.g., dsRNA) has an $IC_{50}$ in the range of 0.0005-1 nM, e.g., between 0.001 and 0.2 nM, between 0.002 and 0.1 nM, between 0.005 and 0.075 nM, or between 0.01 and 0.05 nM. In embodiments, the iRNA (e.g., dsRNA) has an $IC_{50}$ equal to or less than 0.02 nM, e.g., between 0.0005 and 0.02 nM, between 0.001 and 0.02 nM, between 0.005 and 0.02 nM, or between 0.01 and 0.02 nM. In embodiments, the iRNA (e.g., dsRNA) has an $IC_{50}$ in the range of 0.01-1 nM.

In embodiments, a method described herein ameliorates a symptom associated with a LECT2 related disorder (e.g., a LECT2 amyloidosis).

In embodiments, a method described herein inhibits expression of a LECT2 gene in the subject.

In embodiments, a method described herein inhibits inhibits amyloid deposition (e.g., by preventing amyloid deposition or reducing amyloid deposition, e.g., by reducing size, number, or extent of amyloid deposits).

In embodiments, the iRNA (e.g., dsRNA) or composition comprising the iRNA is administered according to a dosing regimen.

In embodiments, the subject is of Mexican descent (e.g., a Mexican American).

In embodiments, the subject carries the G allele of the LECT2 gene that encodes valine at position 40 in the mature protein (amino acid 58 in the unprocessed protein). In embodiments, the subject is homozygous for the G allele (G/G genotype).

In embodiments, a LECT2 protein expressed in the subject has valine at position 40 in the mature protein (or at amino acid 58 in the unprocessed protein).

In embodiments, the iRNA (e.g., dsRNA) or composition comprising the iRNA is administered repeatedly, e.g., according to a dosing regimen.

In embodiments, the iRNA (e.g., dsRNA) or composition comprising the iRNA is administered subcutaneously. In embodiments, the iRNA is in the form of a GalNAc conjugate. In embodiments, the iRNA (e.g., the dsRNA) is administered at a dose of 0.5-50 mg/kg. In embodiments, the iRNA (e.g., dsRNA) is in the form of a GalNAc conjugate and is administered at a dose of 1 to 10 mg/kg.

In an aspect provided herein is a vector encoding at least one strand of an iRNA (e.g., a dsRNA) as described herein.

In an aspect provided herein is a vector encoding at least one strand of a dsRNA, wherein said dsRNA comprises a region of complementarity to at least a part of an mRNA encoding LECT2, wherein said dsRNA is 30 base pairs or less in length, and wherein said dsRNA targets said mRNA for cleavage.

In embodiments, the region of complementarity is at least 15 nucleotides in length.

In embodiments, the region of complementarity is 19 to 21 nucleotides in length.

In one aspect, a vector is provided for inhibiting the expression of a LECT2 gene in a cell. In one embodiment, the vector comprises an iRNA as described herein. In one embodiment, the vector includes at least one regulatory sequence operably linked to a nucleotide sequence that encodes at least one strand of an iRNA as described herein. In one embodiment the vector comprises at least one strand of a LECT2 iRNA.

In an aspect provided herein is a cell comprising a vector as described herein.

In an aspect provided herein is a cell containing a vector for inhibiting the expression of a LECT2 gene in a cell. The vector includes a regulatory sequence operably linked to a nucleotide sequence that encodes at least one strand of an iRNA described herein.

All publications, patent applications, patents, and other references mentioned herein are incorporated by reference in their entirety.

The details of various embodiments of the invention are set forth in the description below. Other features, objects, and advantages of the invention will be apparent from the description and the drawings, and from the claims.

DESCRIPTION OF THE DRAWINGS

FIG. 1 depicts a human LECT2 mRNA transcript sequence (Ref. Seq. NM_002302.2 GI:59806344, record dated Apr. 17, 2013; SEQ ID NO: 1).

DETAILED DESCRIPTION OF THE INVENTION iRNA directs the sequence-specific degradation of mRNA through a process known as RNA interference (RNAi). Described herein are iRNAs and methods of using them for modulating (e.g., inhibiting) the expression of a LECT2 gene. Also provided are compositions and methods for treatment of disorders related to LECT2 expression, such as amyloidosis (e.g., LECT2 amyloidosis).

The iRNAs of the compositions featured herein include an RNA strand (the antisense strand) having a region which is 30 nucleotides or less in length, i.e., 15-30 nucleotides in length, generally 19-24 nucleotides in length, which region is substantially complementary to at least part of an mRNA transcript of a LECT2 gene (also referred to herein as an "LECT2-specific iRNA"). The use of such an iRNA enables the targeted degradation of mRNAs of genes that are implicated in disorders related to LECT2 expression, as described herein. Very low dosages of LECT2-specific iRNAs can specifically and efficiently mediate RNAi, resulting in significant inhibition of expression of a LECT2 gene. iRNAs targeting LECT2 can specifically and efficiently mediate RNAi, resulting in significant inhibition of expression of a LECT2 gene, which can be assessed, e.g., in cell based assays.

The following description discloses how to make and use compositions containing iRNAs to modulate (e.g., inhibit) the expression of a LECT2 gene, as well as compositions and methods for treating disorders related to expression of a LECT2 gene.

Embodiments of the pharmaceutical compositions featured herein include an iRNA having an antisense strand comprising a region which is 30 nucleotides or less in length, generally 19-24 nucleotides in length, which region is substantially complementary to at least part of an RNA transcript of a LECT2 gene.

In some aspects, pharmaceutical compositions containing a LECT2 iRNA and a pharmaceutically acceptable carrier, methods of using the compositions to inhibit expression of a LECT2 gene, and methods of using the pharmaceutical compositions to treat disorders related to expression of a LECT2 gene (e.g., LECT2 amyloidosis) are featured herein.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

As used herein, "LECT2" refers to leukocyte chemotactic factor 2 (also known as leukocyte cell-derived chemotaxin 2, chondromodulin-II, chm-II or chm2). See, e.g., Yamagoe S et al. *Genomics,* 1998 Mar. 15; 48(3):324-9. LECT2 was first identified as a novel neutrophil chemotactic protein and is identical with chondromodulin II, a growth stimulator for chondrocytes and osteoblasts. The human LECT2 gene was mapped to chromosome 5q31.1-q32. Ibid.

The sequence of a human LECT2 mRNA transcript can be found at NM_002302.2 (SEQ ID NO: 1). The sequence of a mouse LECT2 mRNA can be found at NM_010702.1 and at NM_010702.2, and the sequence of a rat LECT2 mRNA can be found at NM_001108405.1.

The human LECT2 protein is a secreted, 16 kDa protein. The LECT2 protein is secreted by the liver. It has high sequence similarity to the chondromodulin repeat regions of the chicken myb-induced myeloid 1 protein. Polymorphism in the LECT2 gene has been associated with rheumatoid arthritis. Ibid.

LECT2 is expressed in various tissues, including the brain and stomach as well as the liver. Koshimizu, Y & Ohtomi, M. (2010) *Brain Res.* 1311:1-11. In a study using indirect immunoperoxidase staining to investigate the expression of LECT2 in normal and diseased human organs and tissues other than liver, it was found that LECT2 was generally expressed in vascular, endothelial and smooth muscle cells, adipocytes, cerebral nerve cells, apical squamous epithelia, parathyroid cells, sweat and sebaceous glandular epithelia, Hassall bodies and some mononuclear cells in immunohematopoeietic tissue. This protein was generally negative, although occasionally positively stained in osteoblasts, chondrocytes, cardiac and skeletal muscle cells, smooth muscle cells of the gastrointestinal tract, and the epithelial cells of some tissues. Nagai et al. (1998) *Pathol Int.* 48(11): 882-6.

The human LECT2 gene codes for 151 amino acids including an 18 amino acid signal peptide. The secreted protein has 133 residues. A G/A polymorphism at nucleotide 172 in exon 3 of the gene (codon change GTC to ATC) has been identified and accounts for the presence of either valine or isoleucine at position 58 of the unprocessed protein (or position 40 of the mature protein). The G allele has an overall frequency of 0.477 and a frequency range of 0.6-0.7 in individuals of European descent. See Benson, M. D. et al. (2008) *Kidney International,* 74: 218-222; Murphy, C. L. et al. (2010)*Am J Kidney Dis,* 56(6):1100-1107. Patients with LECT2 amyloidosis typically are homozygous for the G allele. Without wishing to be bound by theory, it has been suggested that replacement of the buried isoleucine (A allele) side chain with valine (G allele) could destabilize the protein and possibly account for the amyloidogenic propensity of this LECT2 variant. Murphy, C. L. et al. (2010) *Am J Kidney Dis,* 56(6):1100-1107.

As used herein, a "LECT2 amyloidosis" or "ALECT2" includes an amyloidosis involving deposits of amyloid or amyloid fibrils that contain a LECT2 protein (e.g., any polymorphic variant of a LECT2 protein) or a portion of a LECT2 protein. The LECT2 protein can be a variant (e.g., a mutant) LECT2 protein. The amyloidosis can be systemic or local. In embodiments, the LECT2 amyloidosis involves amyloid deposits in the kidney and/or liver.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, the term "iRNA," "RNAi", "iRNA agent," or "RNAi agent" refers to an agent that contains RNA as that term is defined herein, and which mediates the targeted cleavage of an RNA transcript, e.g., via an RNA-induced silencing complex (RISC) pathway. In one embodiment, an iRNA as described herein effects inhibition of LECT2 expression. Inhibition of ALECT2 expression may be assessed based on a reduction in the level of ALECT2 mRNA or a reduction in the level of the ALECT2 protein. As used herein, "target sequence" refers to a contiguous portion of the nucleotide sequence of an mRNA molecule formed during the transcription of an ALECT2 gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all subranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding an ALECT2 protein). For example, a polynucleotide is complementary to at least a part of a LECT2 mRNA if the sequence is substantially complementary to a non-interrupted portion of an mRNA encoding LECT2. As another example, a polynucleotide is complementary to at least a part of a LECT2 mRNA if the sequence is substantially complementary to a non-interrupted portion of an mRNA encoding LECT2.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA, e.g., through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

In another embodiment, the iRNA agent may be a "single-stranded siRNA" that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein (e.g., sequences provided in Tables 2-3, 5-6 and 9-10) may be used as a single-stranded siRNA as described herein or as chemically modified by the methods described in Lima et al., (2012) *Cell* 150:883-894.

In another aspect, the RNA agent is a "single-stranded antisense RNA molecule." An single-stranded antisense RNA molecule is complementary to a sequence within the target mRNA. Single-stranded antisense RNA molecules can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense molecules inhibit a target mRNA by hydridizing to the target and cleaving the target through an RNaseH cleavage event. The single-stranded antisense RNA molecule may be about 10 to about 30 nucleotides in length and have a sequence that is complementary to a target sequence. In one embodiment, the single-stranded antisense RNA molecule may comprise a sequence that is at least about 10, 11, 12, 13, 14, 15, 16, 17, 18, 19, 20, or more contiguous nucleotides complementary to any of the target sites described herein, e.g., sequences provided in any one of Tables 2-3, 5-6 and 9-10. In another embodiment, the single-stranded antisense RNA molecule may comprise a sequence that is at least about 10, 11, 12, 13, 14, 15, 16, 17, 18, 19, 20, or more contiguous nucleotides from any one of the antisense nucleotide sequences described herein, e.g., sequences provided in any one of Tables 2-3, 5-6 and 9-10.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure, in the ribose structure, or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, an acyclic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA, e.g., via a RISC pathway.

In one aspect, a modified ribonucleoside includes a deoxyribonucleoside. In such an instance, an iRNA agent can comprise one or more deoxynucleosides, including, for example, a deoxynucleoside overhang(s), or one or more deoxynucleosides within the double stranded portion of a dsRNA. In certain embodiments, the RNA molecule comprises a percentage of deoxyribonucleoses of at least 5, 10, 15, 20, 25, 30, 35, 40, 45, 50, 55, 60, 65, 70, 75, 80, 85, 90, 95% or higher (but not 100%) deoxyribonucleosides, e.g., in one or both strands. In other embodiments, the term "iRNA" does not encompass a double stranded DNA molecule (e.g., a naturally-occurring double stranded DNA molecule or a 100% deoxynucleoside-containing DNA molecule).

In one aspect, an RNA interference agent includes a single stranded RNA that interacts with a target RNA sequence to direct the cleavage of the target RNA. Without wishing to be bound by theory, long double stranded RNA introduced into cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 2006/0240093, 2007/

0135372, and in International Application No. WO 2009/082817. These applications are incorporated herein by reference in their entirety.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA may also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a β-glucan delivery system, such as those described in U.S. Pat. Nos. 5,032,401 and 5,607,677, and U.S. Publication No. 2005/0281781, which are hereby incorporated by reference in their entirety. In vitro introduction into a cell includes methods known in the art such as electroporation and lipofection. Further approaches are described herein below or known in the art.

As used herein, the term "modulate the expression of," refers to at an least partial "inhibition" or partial "activation" of a LECT2 gene expression in a cell treated with an iRNA composition as described herein compared to the expression of LECT2 in a control cell. A control cell includes an untreated cell, or a cell treated with a non-targeting control iRNA.

The terms "activate," "enhance," "up-regulate the expression of," "increase the expression of," and the like, in so far as they refer to a LECT2 gene, herein refer to the at least partial activation of the expression of a LECT2 gene, as manifested by an increase in the amount of LECT2 mRNA, which may be isolated from or detected in a first cell or group of cells in which a LECT2 gene is transcribed and which has or have been treated such that the expression of a LECT2 gene is increased, as compared to a second cell or group of cells substantially identical to the first cell or group of cells but which has or have not been so treated (control cells).

In one embodiment, expression of a LECT2 gene is activated by at least about 10%, 15%, 20%, 25%, 30%, 35%, 40%, 45%, or 50% by administration of an iRNA as described herein. In some embodiments, a LECT2 gene is activated by at least about 60%, 70%, or 80% by administration of an iRNA featured in the invention. In some embodiments, expression of a LECT2 gene is activated by at least about 85%, 90%, or 95% or more by administration of an iRNA as described herein. In some embodiments, the LECT2 gene expression is increased by at least 1-fold, at least 2-fold, at least 5-fold, at least 10-fold, at least 50-fold, at least 100-fold, at least 500-fold, at least 1000 fold or more in cells treated with an iRNA as described herein compared to the expression in an untreated cell. Activation of expression by small dsRNAs is described, for example, in Li et al., 2006 *Proc. Natl. Acad. Sci. U.S.A.* 103:17337-42, and in US2007/0111963 and US2005/226848, each of which is incorporated herein by reference.

The terms "silence," "inhibit expression of," "down-regulate expression of," "suppress expression of," and the like, in so far as they refer to a LECT2 gene, herein refer to the at least partial suppression of the expression of a LECT2 gene, as assessed, e.g., based on on LECT2 mRNA expression, LECT2 protein expression, or another parameter functionally linked to LECT2 gene expression. For example, inhibition of LECT2 expression may be manifested by a reduction of the amount of LECT2 mRNA which may be isolated from or detected in a first cell or group of cells in which a LECT2 gene is transcribed and which has or have been treated such that the expression of a LECT2 gene is inhibited, as compared to a control. The control may be a second cell or group of cells substantially identical to the first cell or group of cells, except that the second cell or group of cells have not been so treated (control cells). The degree of inhibition is usually expressed as a percentage of a control level, e.g., $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to LECT2 gene expression, e.g., the amount of protein encoded by a LECT2 gene. The reduction of a parameter functionally linked to LECT2 gene expression may similarly be expressed as a percentage of a control level. In principle, LECT2 gene silencing may be determined in any cell expressing LECT2, either constitutively or by genomic engineering, and by any appropriate assay.

For example, in certain instances, expression of a LECT2 gene is suppressed by at least about 10%, 15%, 20%, 25%, 30%, 35%, 40%, 45%, or 50% by administration of an iRNA disclosed herein. In some embodiments, a LECT2 gene is suppressed by at least about 60%, 65%, 70%, 75%, or 80% by administration of an iRNA disclosed herein. In some embodiments, a LECT2 gene is suppressed by at least about 85%, 90%, 95%, 98%, 99%, or more by administration of an iRNA as described herein.

In the context of the present disclosure, the terms "treat," "treatment," and the like mean to prevent, relieve or alleviate at least one symptom associated with a disorder related to LECT2 expression, or to slow or reverse the progression or anticipated progression of such a disorder. For example, the methods featured herein, when employed to treat a LECT2 amyloidosis, may serve to inhibit amyloid deposition, to reduce or prevent one or more symptoms of the amyloidosis, or to reduce the risk or severity of associated conditions (e.g., nephrotic syndrome or hepatitis). Thus, unless the context clearly indicates otherwise, the terms "treat," "treatment," and the like are intended to encompass prophylaxis, e.g., prevention of disorders and/or symptoms of disorders related to LECT2 expression.

By "lower" in the context of a disease marker or symptom is meant any decrease, e.g., a statistically or clinically significant decrease in such level. The decrease can be, for example, at least 10%, at least 20%, at least 30%, at least 40%, at least 40%, at least 50%, at least 60%, at least 70%, at least 80%, or at least 90%. The decrease can be down to a level accepted as within the range of normal for an individual without such disorder.

As used herein, the phrases "therapeutically effective amount" and "prophylactically effective amount" and the like refer to an amount that provides a therapeutic benefit in the treatment, prevention, or management of any disorder or pathological process related to LECT2 expression. The specific amount that is therapeutically effective may vary depending on factors known in the art, such as, for example, the type of disorder or pathological process, the patient's history and age, the stage of the disorder or pathological process, and the administration of other therapies.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, in a method of treating a disorder related to LECT2 expression (e.g., a LECT2 amyloidosis), an effective amount includes an amount effective to reduce one or more symptoms associated with the LECT2 amyloidosis, an amount effective to inhibit amyloid deposition (e.g., LECT2 amyloid deposition), or an amount effective to reduce the risk of developing conditions associated with LECT2 amyloidosis. For example, if a given clinical treatment is considered effective when there is at least a 10% reduction in a measurable parameter associated with a disease or disorder, a therapeutically effective amount of a drug for the treatment of that disease or disorder is the amount necessary to obtain at least a 10% reduction in that parameter. For example, a therapeutically effective amount of an iRNA targeting LECT2 can reduce a level of LECT2 mRNA or a level of LECT2 protein by any measurable amount, e.g., by at least 10%, 20%, 30%, 40% or 50%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

The term "about" when referring to a number or a numerical range means that the number or numerical range referred to is an approximation within experimental variability (or within statistical experimental error), and thus the number or numerical range may vary from, for example, between 1% and 15% of the stated number or numerical range.

II. iRNA Agents

Described herein are iRNA agents that modulate (e.g., inhibit) the expression of a LECT2 gene.

In some embodiments, the iRNA agent activates the expression of a LECT2 gene in a cell or mammal.

In some embodiments, the iRNA agent includes double-stranded ribonucleic acid (dsRNA) molecules for inhibiting the expression of a LECT2 gene in a cell or in a subject (e.g., in a mammal, e.g., in a human), where the dsRNA includes an antisense strand having a region of complementarity which is complementary to at least a part of an mRNA formed in the expression of a LECT2 gene, and where the region of complementarity is 30 nucleotides or less in length, generally 19-24 nucleotides in length, and where the dsRNA, upon contact with a cell expressing the LECT2 gene, inhibits the expression of the LECT2 gene, e.g., by at least 10%, 20%, 30%, 40%, or 50%.

The modulation (e.g., inhibition) of expression of the LECT2 gene can be assayed by, for example, a PCR or branched DNA (bDNA)-based method, or by a protein-based method, such as by Western blot. Expression of a LECT2 gene in cell culture, such as in COS cells, HeLa cells, primary hepatocytes, HepG2 cells, primary cultured cells or in a biological sample from a subject can be assayed by measuring LECT2 mRNA levels, such as by bDNA or TaqMan assay, or by measuring protein levels, such as by immunofluorescence analysis, using, for example, Western Blotting or flow cytometric techniques.

A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence, derived from the sequence of an mRNA formed during the expression of a LECT2 gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive.

In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, e.g., 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, an miRNA is a dsRNA. In another embodiment, a dsRNA is not a naturally occurring miRNA. In another embodiment, an iRNA agent useful to target LECT2 expression is not generated in the target cell by cleavage of a larger dsRNA.

A dsRNA as described herein may further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc.

In one embodiment, a LECT2 gene is a human LECT2 gene. In another embodiment the LECT2 gene is a mouse or a rat LECT2 gene.

In specific embodiments, the dsRNA comprises a sense strand that comprises or consists of a sense sequence selected from the sense sequences provided in Tables 2-3, 5-6 and 9-10, and an antisense strand that comprises or consists of an antisense sequence selected from the antisense sequences provided in Tables 2-3, 5-6 and 9-10.

In one aspect, a dsRNA will include at least sense and antisense nucleotide sequences, whereby the sense strand is selected from the sequences provided in Tables 2-3, 5-6 and 9-10, and the corresponding antisense strand is selected from the sequences provided in Tables 2-3, 5-6 and 9-10.

In these aspects, one of the two sequences is complementary to the other of the two sequences, with one of the sequences being substantially complementary to a sequence of an mRNA generated by the expression of a LECT2 gene. As such, a dsRNA will include two oligonucleotides, where one oligonucleotide is described as the sense strand, and the second oligonucleotide is described as the corresponding antisense strand. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., *EMBO* 2001, 20:6877-6888). However, others have found that shorter or longer RNA duplex structures can be effective as well.

In the embodiments described above, by virtue of the nature of the oligonucleotide sequences provided in Tables 2-3, 5-6 and 9-10, dsRNAs described herein can include at least one strand of a length of minimally 19 nucleotides. It can be reasonably expected that shorter duplexes having one of the sequences of Tables 2, 3, 5, 6, 9 or 10 minus only a few nucleotides on one or both ends will be similarly effective as compared to the dsRNAs described above.

In some embodiments, the dsRNA has a partial sequence of at least 15, 16, 17, 18, 19, 20, or more contiguous nucleotides from one of the sequences of Tables 2, 3, 5, 6, 9 or 10.

In some embodiments, the dsRNA has an antisense sequence that comprises at least 15, 16, 17, 18, or 19 contiguous nucleotides of an antisense sequence provided in Table 2 and a sense sequence that comprises at least 15, 16, 17, 18, or 19 contiguous nucleotides of a corresponding sense sequence provided in Table 2.

In some embodiments, the dsRNA comprises an antisense sequence that comprises at least 15, 16, 17, 18, 19, 20, 21, 22, or 23 contiguous nucleotides of an antisense sequence provided in Table 3 and a sense sequence that comprises at least 15, 16, 17, 18, 19, 20, or 21 contiguous nucleotides of a corresponding sense sequence provided in Table 3.

In some embodiments, the dsRNA comprises an antisense sequence that comprises at least 15, 16, 17, 18, 19, 20, 21, 22, or 23 contiguous nucleotides of an antisense sequence provided in Table 5 and a sense sequence that comprises at least 15, 16, 17, 18, 19, 20, or 21 contiguous nucleotides of a corresponding sense sequence provided in Table 5.

In some embodiments, the dsRNA comprises an antisense sequence that comprises at least 15, 16, 17, 18, 19, 20, 21, 22, or 23 contiguous nucleotides of an antisense sequence provided in Table 6 and a sense sequence that comprises at least 15, 16, 17, 18, 19, 20, or 21 contiguous nucleotides of a corresponding sense sequence provided in Table 6.

In some embodiments, the dsRNA comprises an antisense sequence that comprises at least 15, 16, 17, 18, 19, 20, 21, 22, or 23 contiguous nucleotides of an antisense sequence provided in Table 5 and a sense sequence that comprises at least 15, 16, 17, 18, 19, 20, or 21 contiguous nucleotides of a corresponding sense sequence provided in Table 9.

In some embodiments, the dsRNA comprises an antisense sequence that comprises at least 15, 16, 17, 18, 19, 20, 21, 22, or 23 contiguous nucleotides of an antisense sequence provided in Table 6 and a sense sequence that comprises at least 15, 16, 17, 18, 19, 20, or 21 contiguous nucleotides of a corresponding sense sequence provided in Table 10.

In some such embodiments, the dsRNA, although it comprises only a portion of the sequences provided in Table 2, 3, 5, 6, 9 or 10, is equally effective in inhibiting a level of LECT2 expression as is a dsRNA that comprises the full length sequences provided in Table 2, 3, 5, 6, 9 or 10. In some embodiments, the dsRNA differs in its inhibition of a level of expression of a LECT2 gene by not more than 5, 10, 15, 20, 25, 30, 35, 40, 45, or 50% inhibition compared with a dsRNA comprising the full sequence disclosed herein.

The iRNAs provided in Tables 2-3, 5-6 and 9-10 identify a site in a LECT2 transcript that is susceptible to RISC-mediated cleavage. As such, the present invention further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides from one of the sequences provided in Tables 2-3, 5-6 and 9-10 coupled to additional nucleotide sequences taken from the region contiguous to the selected sequence in a LECT2 gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays described herein or known in the art) to identify those sequences that perform optimally can identify those RNA sequences that, when targeted with an iRNA agent, mediate the best inhibition of target gene expression. Thus, while the sequences identified, for example, in Tables 2-3, 5-6 and 9-10, represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Tables 2-3, 5-6 and 9-10, further optimization can be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a LECT2 gene, the RNA strand generally does not contain any mismatch within the central 13 nucleotides. The methods described herein or methods known in the art can be used to determine whether an iRNA containing a mismatch to a target sequence is effective in inhibiting the expression of a LECT2 gene. Consideration of the efficacy of iRNAs with mismatches in inhibiting expression of a LECT2 gene is important, especially if the particular region of complementarity in a LECT2 gene is known to have polymorphic sequence variation within the population.

In one embodiment, at least one end of a dsRNA has a single-stranded nucleotide overhang of 1 to 4, generally 1 or 2 nucleotides. dsRNAs having at least one nucleotide overhang have unexpectedly superior inhibitory properties relative to their blunt-ended counterparts. In yet another embodiment, the RNA of an iRNA (e.g., a dsRNA) is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position, or having an acyclic sugar) or replacement of the sugar, as well as (d) backbone modifications, including modification or replacement of the phosphodiester linkages. Specific examples of RNA compounds useful in this invention include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —CH$_2$—NH—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$—[wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs may also contain one or more substituted sugar moieties. The iRNAs, e.g., dsRNAs, featured herein can include one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Exemplary suitable modifications include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, dsRNAs include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

In other embodiments, an iRNA agent comprises one or more (e.g., about 1, 2, 3, 4, 5, 6, 7, 8, 9, 10, or more) acyclic nucleotides (or nucleosides). In certain embodiments, the sense strand or the antisense strand, or both sense strand and antisense strand, include less than five acyclic nucleotides per strand (e.g., four, three, two or one acyclic nucleotides per strand). The one or more acyclic nucleotides can be found, for example, in the double-stranded region, of the sense or antisense strand, or both strands; at the 5'-end, the 3'-end, both of the 5' and 3'-ends of the sense or antisense strand, or both strands, of the iRNA agent. In one embodiment, one or more acyclic nucleotides are present at positions 1 to 8 of the sense or antisense strand, or both. In one embodiment, one or more acyclic nucleotides are found in the antisense strand at positions 4 to 10 (e.g., positions 6-8) from the 5'-end of the antisense strand. In another embodiment, the one or more acyclic nucleotides are found at one or both 3'-terminal overhangs of the iRNA agent.

The term "acyclic nucleotide" or "acyclic nucleoside" as used herein refers to any nucleotide or nucleoside having an acyclic sugar, e.g., an acyclic ribose. An exemplary acyclic nucleotide or nucleoside can include a nucleobase, e.g., a naturally-occurring or a modified nucleobase (e.g., a nucleobase as described herein). In certain embodiments, a bond between any of the ribose carbons (C1, C2, C3, C4, or C5), is independently or in combination absent from the nucleotide. In one embodiment, the bond between C2-C3 carbons of the ribose ring is absent, e.g., an acyclic 2'-3'-seconucleotide monomer. In other embodiments, the bond between C1-C2, C3-C4, or C4-C5 is absent (e.g., a 1'-2', 3'-4' or 4'-5'-seco nucleotide monomer). Exemplary acyclic nucleotides are disclosed in U.S. Pat. No. 8,314,227, incorporated herein by reference in its entirely. For example, an acyclic nucleotide can include any of monomers D-J in FIGS. 1-2 of U.S. Pat. No. 8,314,227. In one embodiment, the acyclic nucleotide includes the following monomer:

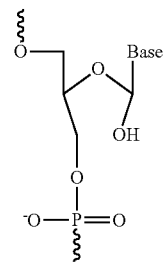

wherein Base is a nucleobase, e.g., a naturally-occurring or a modified nucleobase (e.g., a nucleobase as described herein).

In certain embodiments, the acyclic nucleotide can be modified or derivatized, e.g., by coupling the acyclic nucleotide to another moiety, e.g., a ligand (e.g., a GalNAc, a cholesterol ligand), an alkyl, a polyamine, a sugar, a polypeptide, among others.

In other embodiments, the iRNA agent includes one or more acyclic nucleotides and one or more LNAs (e.g., an LNA as described herein). For example, one or more acyclic nucleotides and/or one or more LNAs can be present in the sense strand, the antisense strand, or both. The number of acyclic nucleotides in one strand can be the same or different from the number of LNAs in the opposing strand. In certain embodiments, the sense strand and/or the antisense strand comprises less than five LNAs (e.g., four, three, two or one LNAs) located in the double-stranded region or a 3'-overhang. In other embodiments, one or two LNAs are located in the double stranded region or the 3'-overhang of the sense strand. Alternatively, or in combination, the sense strand and/or antisense strand comprises less than five acyclic nucleotides (e.g., four, three, two or one acyclic nucleotides) in the double-stranded region or a 3'-overhang. In one embodiment, the sense strand of the iRNA agent comprises one or two LNAs in the 3'-overhang of the sense strand, and one or two acyclic nucleotides in the double-stranded region of the antisense strand (e.g., at positions 4 to 10 (e.g., positions 6-8) from the 5'-end of the antisense strand) of the iRNA agent.

In other embodiments, inclusion of one or more acyclic nucleotides (alone or in addition to one or more LNAs) in the iRNA agent results in one or more (or all) of: (i) a reduction in an off-target effect; (ii) a reduction in passenger strand participation in RNAi; (iii) an increase in specificity of the guide strand for its target mRNA; (iv) a reduction in a microRNA off-target effect; (v) an increase in stability; or (vi) an increase in resistance to degradation, of the iRNA molecule.

Other modifications include 2'-methoxy (2'-OCH$_3$), 2'-aminopropoxy (2'-OCH$_2$CH$_2$CH$_2$NH$_2$) and 2'-fluoro (2'-F) Similar modifications may also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more (e.g., about 1, 2, 3, 4, 5, 6, 7, 8, 9, 10, or more) locked nucleic acids (LNA) (also referred to herein as "locked nucleotides"). In one embodiment, a locked nucleic acid is a nucleotide having a modified ribose moiety in which the ribose moiety comprises an extra bridge connecting, e.g., the 2' and 4' carbons. This structure effectively "locks" the ribose in the 3'-endo structural conformation. The addition of locked nucleic acids to siRNAs has been shown to increase siRNA stability in serum, increase thermal stability, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. Patents that teach the preparation of locked nucleic acids include, but are not limited to, the following: U.S. Pat. Nos. 6,268,490; 6,670,461; 6,794,499; 6,998,484; 7,053,207; 7,084,125; 7,399,845, and 8,314,227, each of which is herein incorporated by reference in its entirety. Exemplary LNAs include but are not limited to, a 2', 4'-C methylene bicyclo nucleotide (see for example Wengel et al., International PCT Publication No. WO 00/66604 and WO 99/14226).

In other embodiments, the iRNA agents include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, *J. Am. Chem. Soc.*, 120, 8531-8532. A single G-clamp analog substitution within an oligonucleotide can result in substantially enhanced helical thermal stability and mismatch discrimination when hybridized to complementary oligonucleotides. The inclusion of such nucleotides in the iRNA molecules can result in enhanced affinity and specificity to nucleic acid targets, complementary sequences, or template strands.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

iRNA Motifs

In one embodiment, the sense strand sequence may be represented by formula (I):

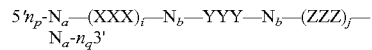

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12 or 11, 12, 13) of the sense strand, the count starting from the 1st nucleotide, from the 5'-end; or optionally, the count starting at the 1st paired nucleotide within the duplex region, from the 5'-end.

In one embodiment, i is 1 and j is 0, or i is 0 and j is 1, or both i and j are 1. The sense strand can therefore be represented by the following formulas:

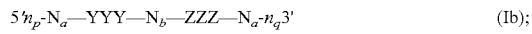  (Ib);

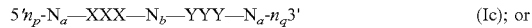  (Ic); or

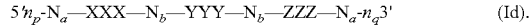  (Id).

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

  (Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

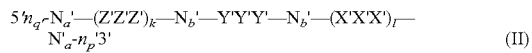  (II)

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides; each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the 1st nucleotide, from the 5'-end; or optionally, the count starting at the 1st paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1. The antisense strand can therefore be represented by the following formulas:

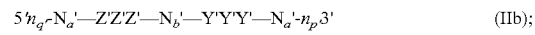  (IIb);

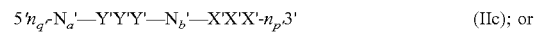  (IIc); or

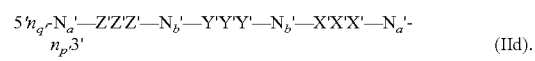  (IId).

When the antisense strand is represented by formula (IIb), $N_b'$ represents an oligonucleotide sequence comprising 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

  (Ia).

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1st nucleotide from the 5'-end, or optionally, the count starting at the 1$^{St}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

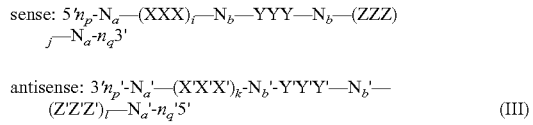

wherein:
j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, $n_p$, $n_q'$, and $n_q$, each of which may or may not be present, independently represents an overhang nucleotide; and
XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

 (IIIa)

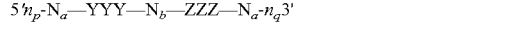

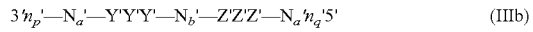 (IIIb)

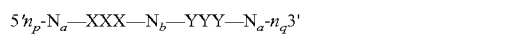

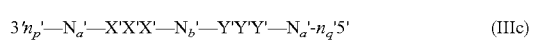 (IIIc)

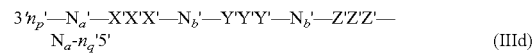 (IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker. In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to to a ligand. Each of the agents can target the same gene or two different genes; or each of the agents can target same gene at two different target sites.

iRNA Conjugates

The iRNA agents disclosed herein can be in the form of conjugates. The conjugate may be attached at any suitable location in the iRNA molecule, e.g., at the 3' end or the 5' end of the sense or the antisense strand. The conjugates are optionally attached via a linker.

In some embodiments, an iRNA agent described herein is chemically linked to one or more ligands, moieties or conjugates, which may confer functionality, e.g., by affecting (e.g., enhancing) the activity, cellular distribution or cellular uptake of the iRNA. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In some embodiments, a ligand provides an enhanced affinity for a selected target, e.g, molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an α helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

In some embodiments, the ligand is a GalNAc ligand that comprises one or more N-acetylgalactosamine (GalNAc) derivatives. In some embodiments, the GalNAc ligand is used to target the iRNA to the liver (e.g., to hepatocytes). Additional description of GalNAc ligands is provided in the section titled Carbohydrate Conjugates.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., *antennapedia* peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Lipid Conjugates

In one embodiment, the ligand is a lipid or lipid-based molecule. Such a lipid or lipid-based molecule can typically bind a serum protein, such as human serum albumin (HSA). An HSA binding ligand allows for distribution of the conjugate to a target tissue. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In one embodiment, the lipid based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In another embodiment, the lipid based ligand binds HSA weakly or not at all, such that distribution of the conjugate to the kidney is enhanced. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

Cell Permeation Agents

In another aspect, the ligand is a cell-permeation agent, such as a helical cell-permeation agent. In one embodiment, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an α-helical agent, and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 685). An RFGF analogue (e.g., amino acid sequence AALLPVLLAAP (SEQ ID NO: 686)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 687)) and the *Drosophila Antennapedia* protein (RQIKIWFQNRRMKWKK (SEQ ID NO: 688)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., *Cancer Res.,* 62:5139-43, 2002). An RGD peptide can facilitate targeting of an dsRNA agent to tumors of a variety of other tissues, including the lung, kidney, spleen, or liver (Aoki et al., *Cancer Gene Therapy* 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver a iRNA agent to a tumor cell expressing $\alpha_v\beta_3$ (Haubner et al., *Jour. Nucl. Med.,* 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate comprises a monosaccharide. In one embodiment, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein.

In some embodiments, the GalNAc conjugate is
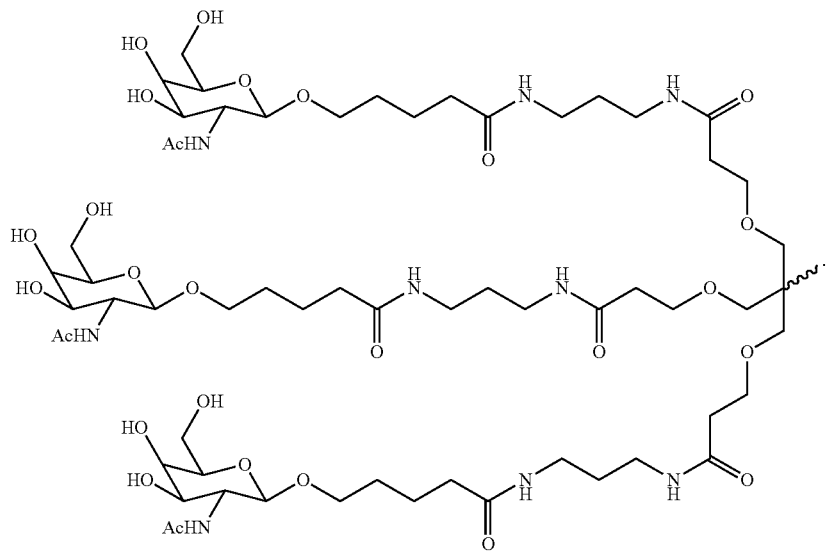
Formula II
In some embodiments, the RNAi agent is attached to the carbohydrate conjugate via a linker as shown in the following schematic, wherein X is O or S
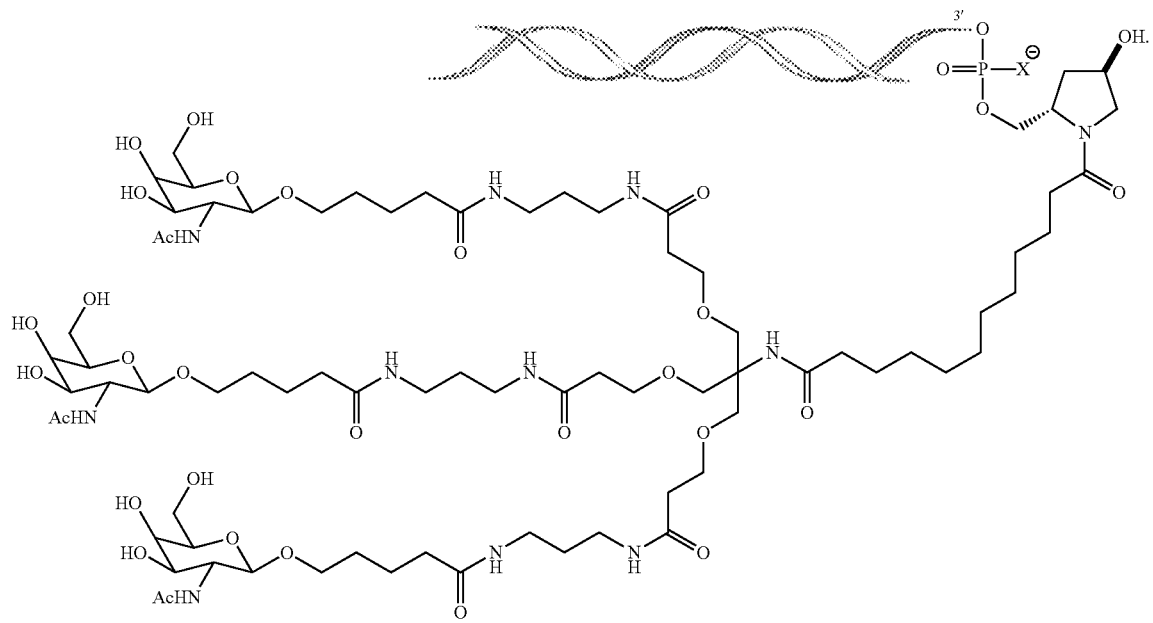
In some embodiments, the RNAi agent is conjugated to L96 as defined in Table 1 and shown below

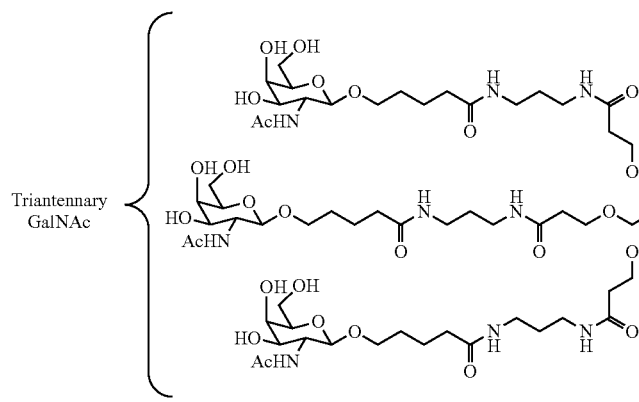
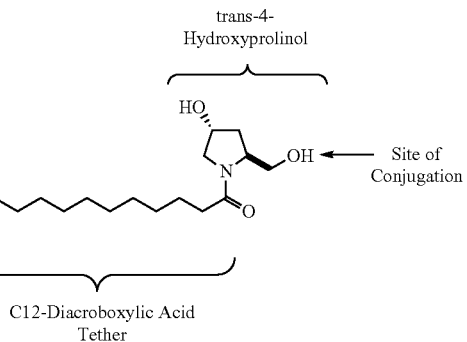
In some embodiments, a carbohydrate conjugate for use in the compositions and methods of the invention is selected from the group consisting of:
Formula II
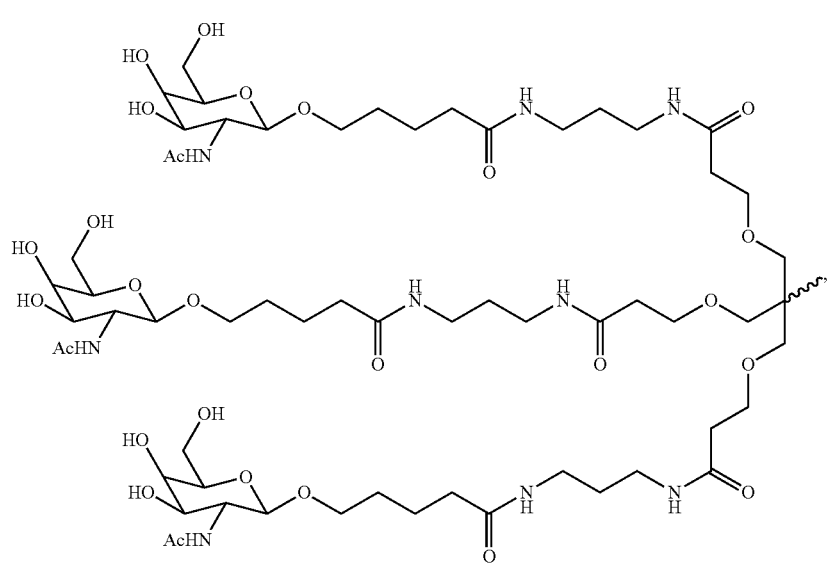
Formula III
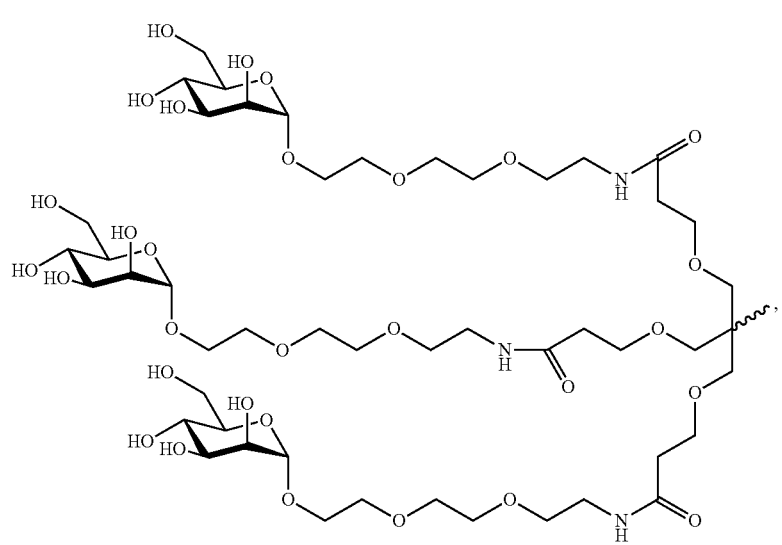

Formula IV
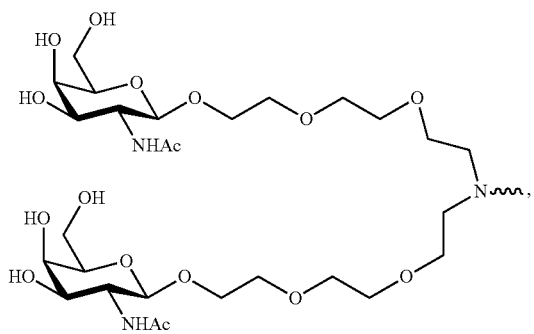
Formula V
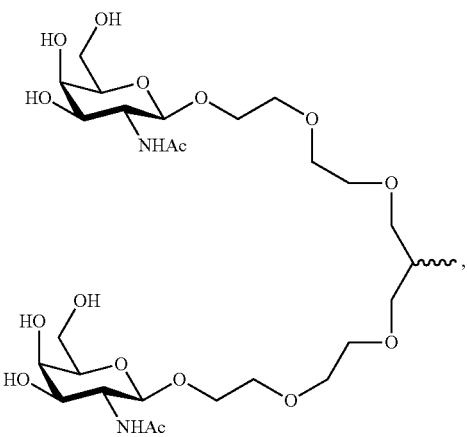
Formula VI
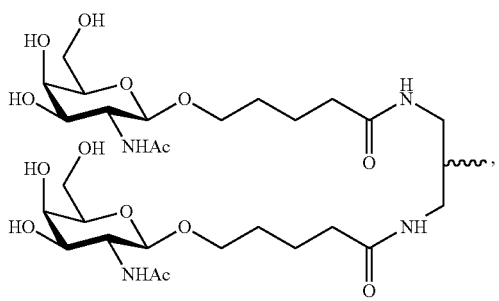
Formula VII
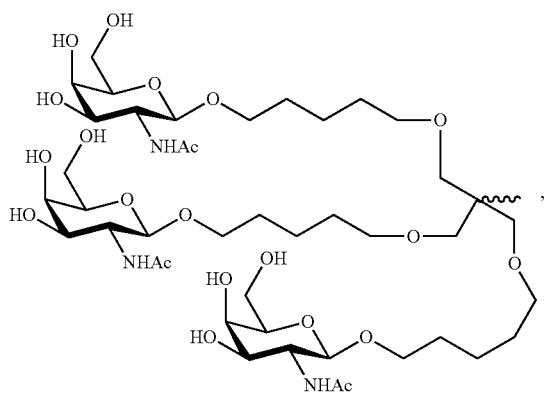
Formula VIII
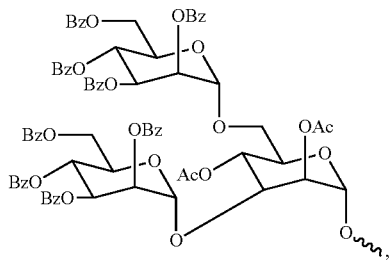
Formula IX
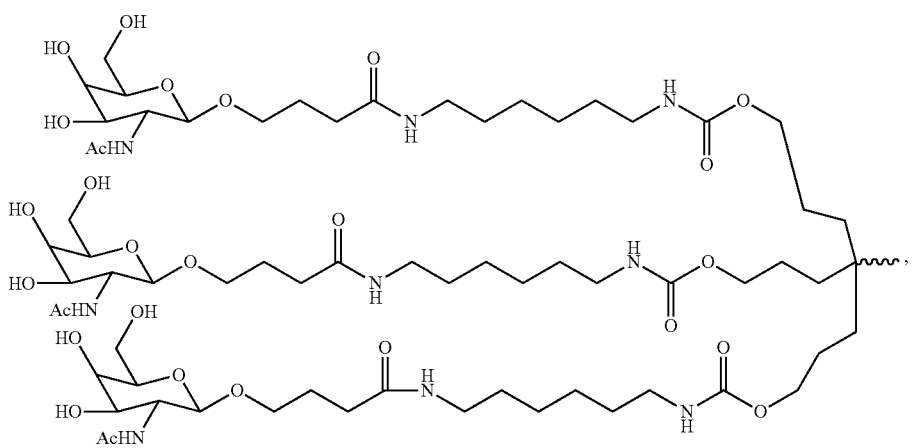

Formula X
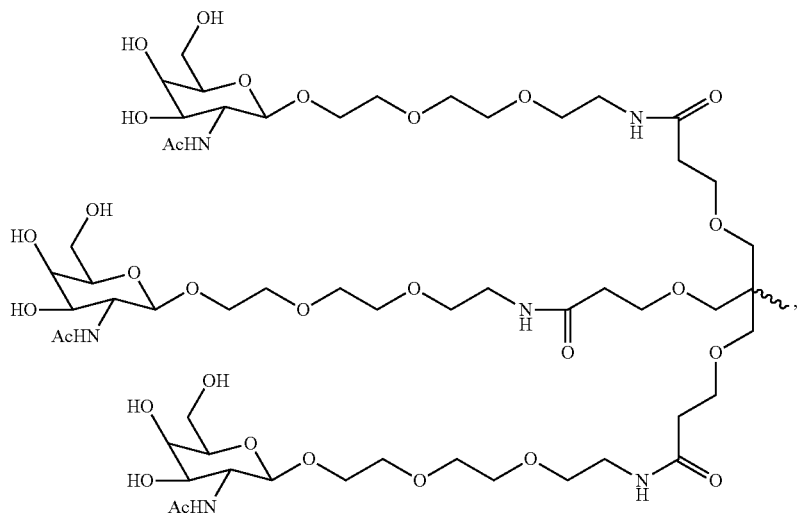
Formula XI
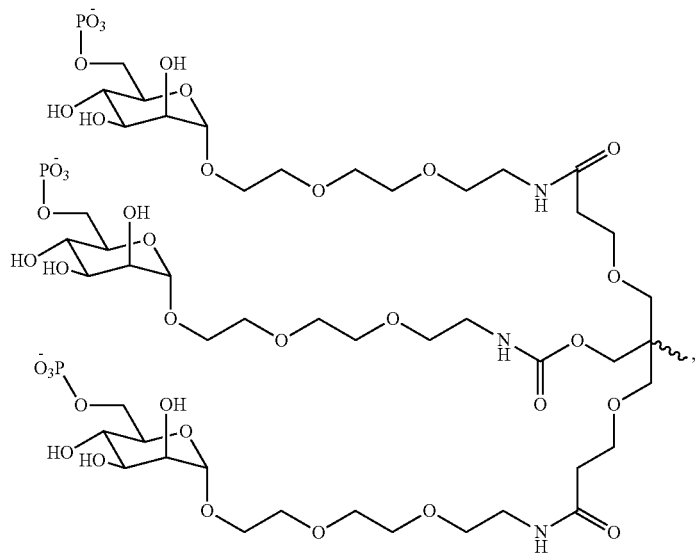

Formula XII
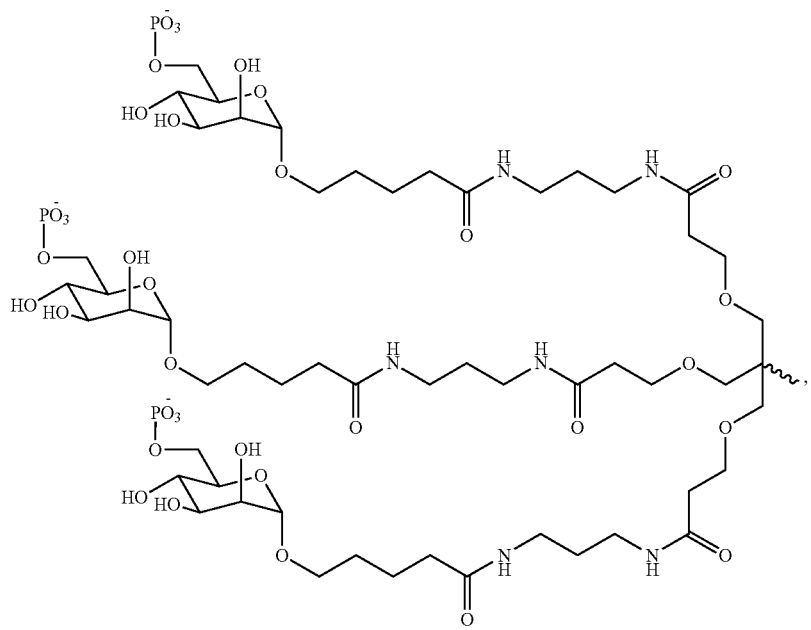
Formula XIII
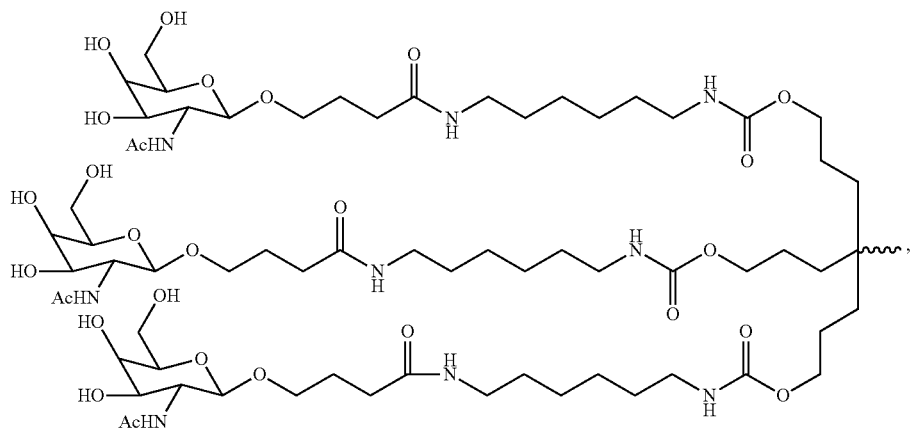
Formula XIV
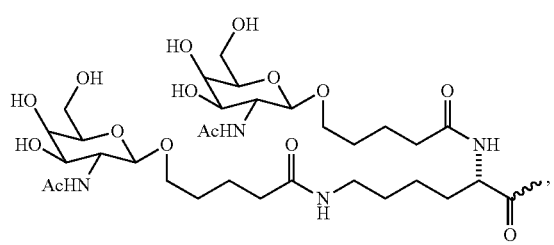
Formula XV
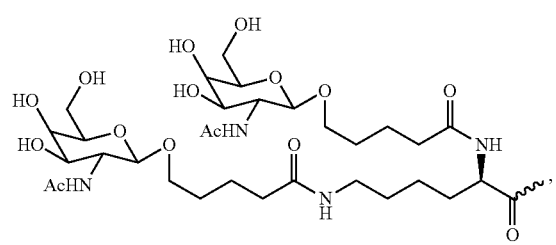
Formula XVI
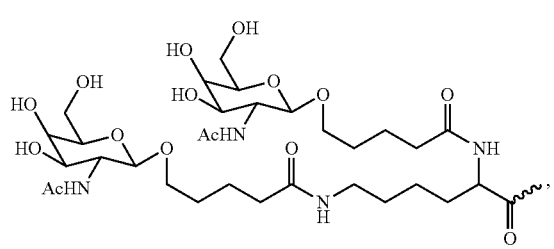
Formula XVII
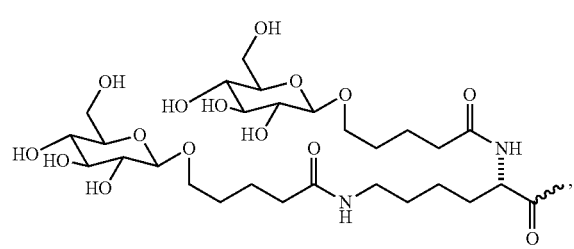

Formula XVIII
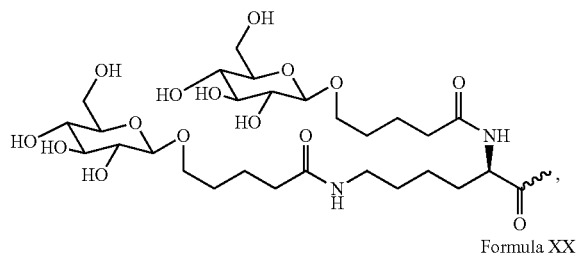
Formula XIX
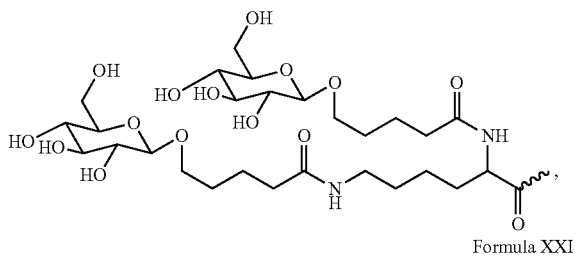
Formula XX Formula XXI
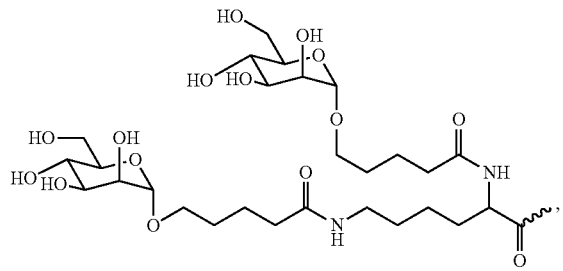
Formula XXII
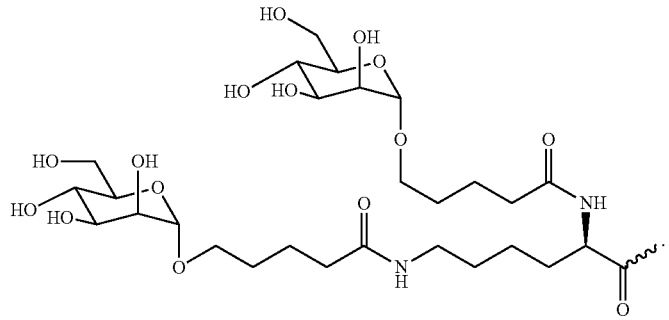
Another representative carbohydrate conjugate for use in the embodiments described herein includes, but is not limited to,
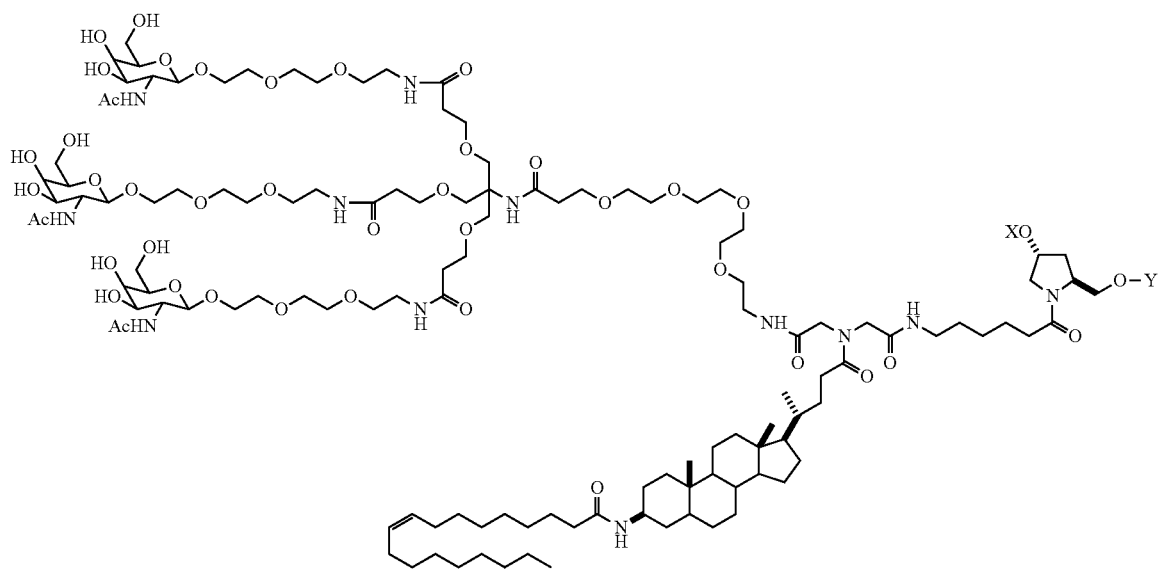
(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

In one embodiment, an iRNA of the invention is conjugated to a carbohydrate through a linker Non-limiting examples of iRNA carbohydrate conjugates with linkers of the compositions and methods of the invention include, but are not limited to, (Formula XXIV)

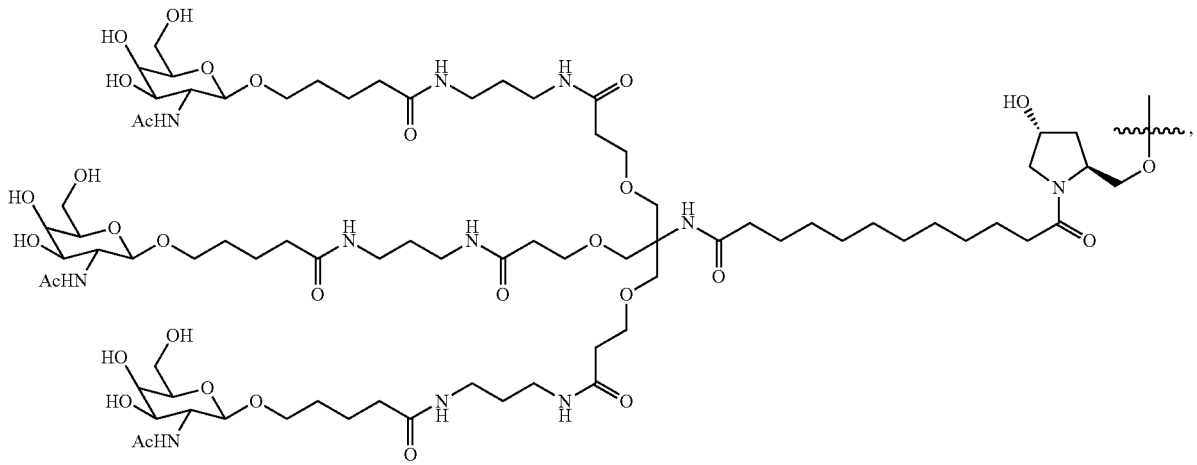

(Formula XXV)

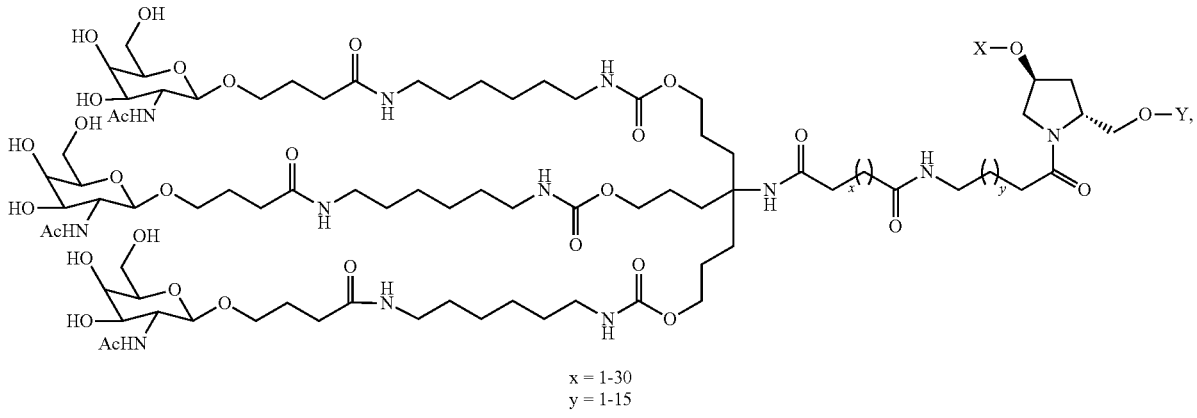

x = 1-30
y = 1-15

(Formula XXVI)

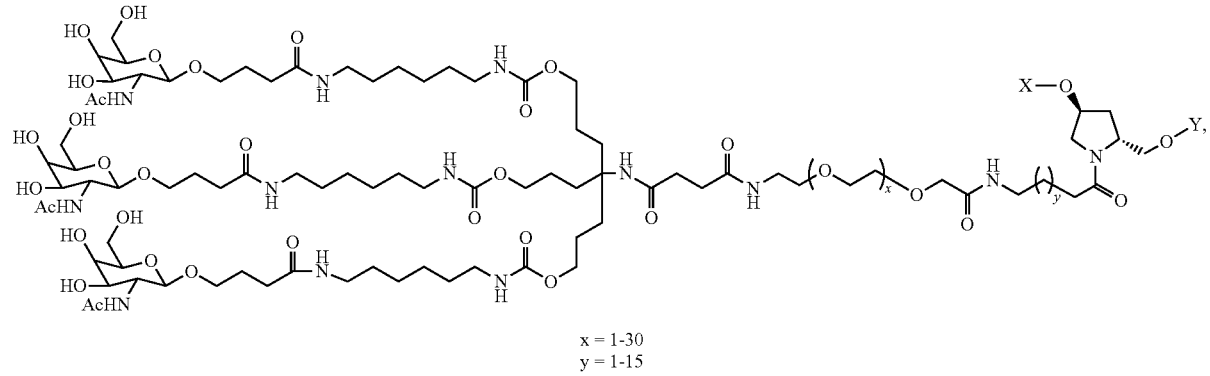

x = 1-30
y = 1-15

(Formula XXVII)
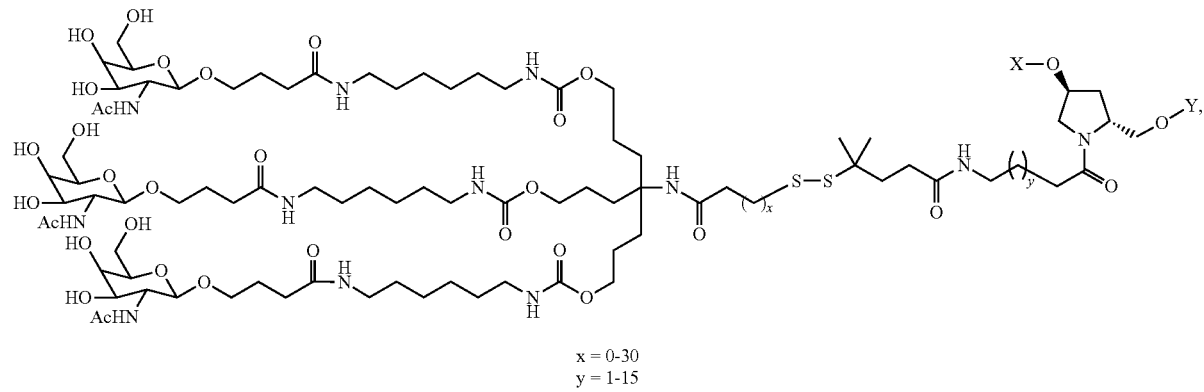
x = 0-30
y = 1-15
(Formula XXVIII)
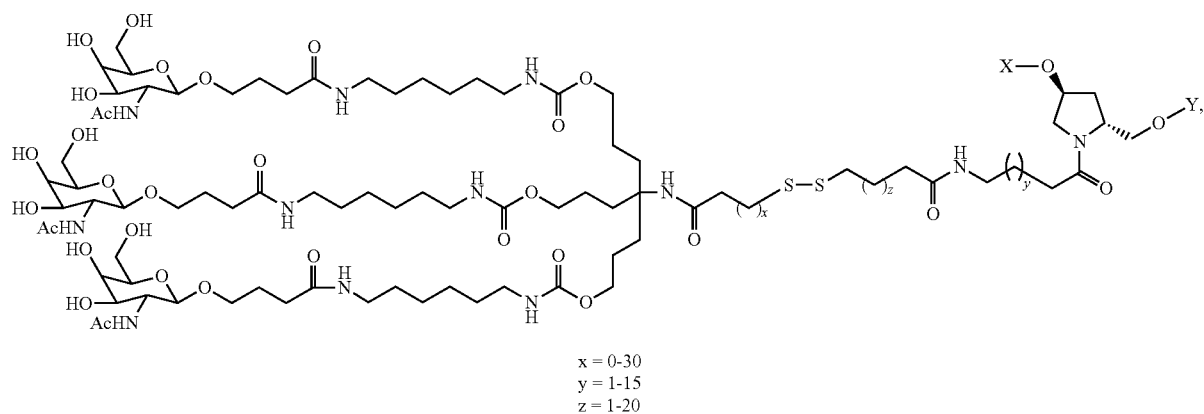
x = 0-30
y = 1-15
z = 1-20
(Formula XXIX)
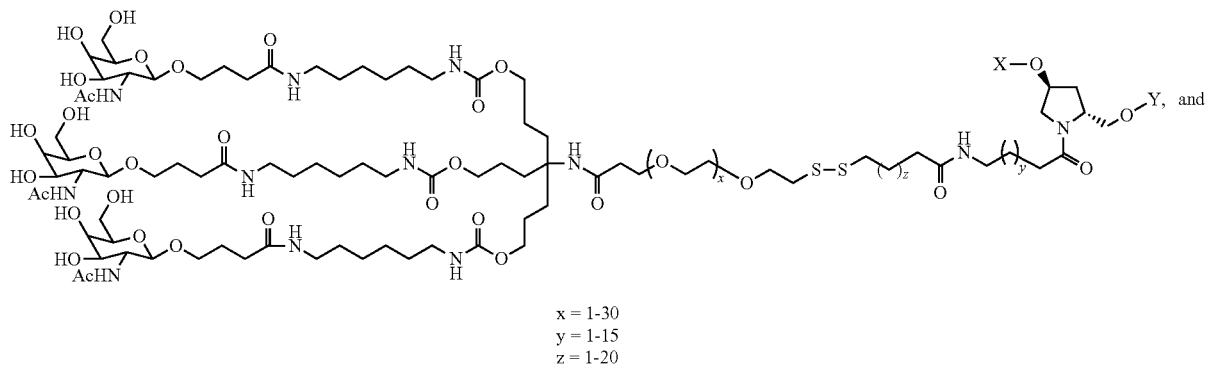
x = 1-30
y = 1-15
z = 1-20
(Formula XXX)
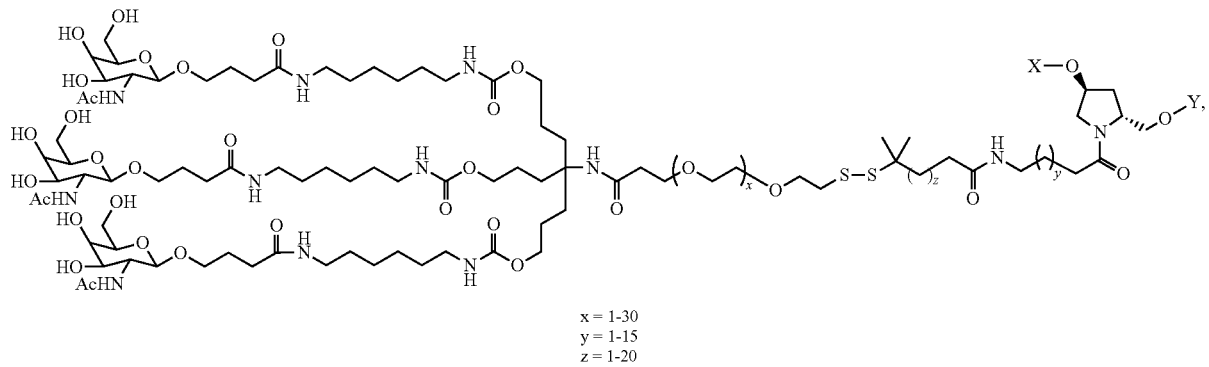
x = 1-30
y = 1-15
z = 1-20 when one of X or Y is an oligonucleotide, the other is a hydrogen.

Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

In one embodiment, a dsRNA of the invention is conjugated to a bivalent or trivalent branched linker selected from the group of structures shown in any of formula (XXXI)-(XXXIV):

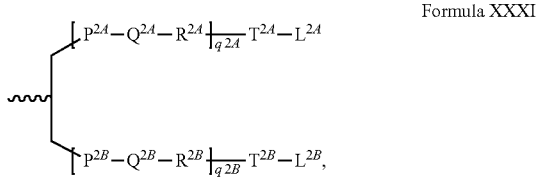

Formula XXXI

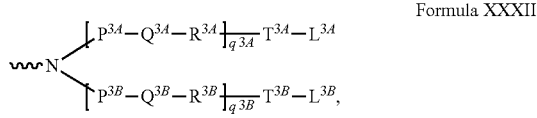

Formula XXXII

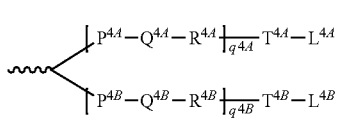

Formula XXXIII

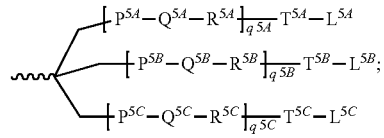

Formula XXXIV wherein:

q2A, q2B, q3A, q3B, q4A, q4B, q5A, q5B and q5C represent independently for each occurrence 0-20 and wherein the repeating unit can be the same or different; $P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$; $Q^{2A}$, $Q^{2B}$, $Q^{3A}$, $Q^{3B}$, $Q^{4A}$, $Q^{4B}$, $Q^{5A}$, $Q^{5B}$, $Q^{5C}$, are independently for each occurrence absent, alkylene, substituted alkylene wherein one or more methylenes can be interrupted or terminated by one or more of O, S, S(O), $SO_2$, N($R^N$), C(R')=C(R''), C≡C or C(O); $R^{2A}$, $R^{2B}$, $R^{3A}$, $R^{3B}$, $R^{4A}$, $R^{4B}$, $R^{5A}$, $R^{5B}$, $R^{5C}$, are each independently for each occurrence absent, NH, O, S, $CH_2$, C(O)O, C(O)NH, NHCH($R^a$)C(O), —C(O)—CH($R^a$)—NH—, CO, CH=N—O,

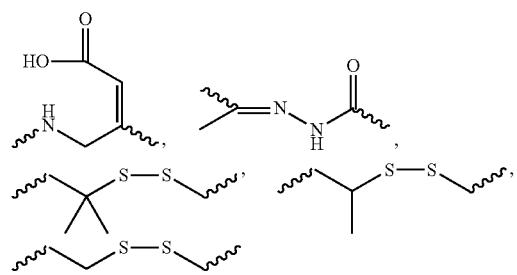

or heterocyclyl;

$L^{2A}$, $L^{2B}$, $L^{3A}$, $L^{3B}$, $L^{4A}$, $L^{4B}$, $L^{5A}$, $L^{5B}$, and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

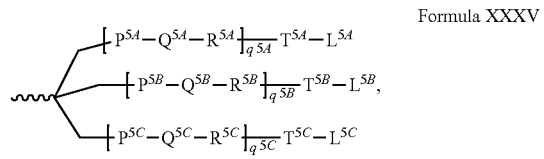

Formula XXXV wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Cleavable Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above. Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which is herein incorporated by reference.

It is not necessary for all positions in a given compound to be uniformly modified, and in fact more than one of the aforementioned modifications may be incorporated in a single compound or even at a single nucleoside within an iRNA. The present invention also includes iRNA compounds that are chimeric compounds.

"Chimeric" iRNA compounds, or "chimeras," in the context of the present invention, are iRNA compounds, e.g., dsRNAs, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

Delivery of iRNA

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA. These alternatives are discussed further below.

Direct Delivery

In general, any method of delivering a nucleic acid molecule can be adapted for use with an iRNA (see e.g., Akhtar S. and Julian R L. (1992) Trends Cell. Biol. 2(5): 139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo.

Modification of the RNA or the pharmaceutical carrier can also permit targeting of the iRNA composition to the target tissue and avoid undesirable off-target effects. iRNA molecules can be modified by chemical conjugation to other groups, e.g., a lipid or carbohydrate group as described herein. Such conjugates can be used to target iRNA to particular cells, e.g., liver cells, e.g., hepatocytes. For example, GalNAc conjugates or lipid (e.g., LNP) formulations can be used to target iRNA to particular cells, e.g., liver cells, e.g., hepatocytes.

Lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Intl. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded iRNAs

In another aspect, iRNA targeting the LECT2 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as an inverted repeat joined by a linker polynucleotide sequence such that the dsRNA has a stem and loop structure.

An iRNA expression vector is typically a DNA plasmid or viral vector. An expression vector compatible with eukaryotic cells, e.g., with vertebrate cells, can be used to produce recombinant constructs for the expression of an iRNA as described herein. Eukaryotic cell expression vectors are well known in the art and are available from a number of commercial sources. Typically, such vectors contain convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

An iRNA expression plasmid can be transfected into a target cell as a complex with a cationic lipid carrier (e.g., Oligofectamine) or a non-cationic lipid-based carrier (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-β-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., *Proc. Soc. Exp. Biol. Med.* 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol.*, 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another typical viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Containing iRNA

In one embodiment, the invention provides pharmaceutical compositions containing an iRNA, as described herein, and a pharmaceutically acceptable carrier. The pharmaceutical composition containing the iRNA is useful for treating a disease or disorder related to the expression or activity of a LECT2 gene (e.g., a LECT2 amyloidosis). Such pharmaceutical compositions are formulated based on the mode of delivery. For example, compositions can be formulated for systemic administration via parenteral delivery, e.g., by intravenous (IV) delivery. In some embodiments, a composition provided herein (e.g., an LNP formulation) is formulated for intravenous delivery. In some embodiments, a composition provided herein (e.g., a composition comprising a GalNAc conjugate) is formulated for subcutaneous delivery.

The pharmaceutical compositions featured herein are administered in a dosage sufficient to inhibit expression of a LECT2 gene. In general, a suitable dose of iRNA will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the iRNA may be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as can be used with the agents of the present invention. In this embodiment, the dosage unit contains a corresponding multiple of the daily dose.

The effect of a single dose on LECT2 levels can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using a suitable animal model.

A suitable animal model, e.g., a mouse containing a transgene expressing human LECT2, can be used to determine the therapeutically effective dose and/or an effective dosage regimen administration of LECT2 siRNA.

The present disclosure also includes pharmaceutical compositions and formulations that include the iRNA compounds featured herein. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as a tissue that produces erythrocytes. For example, the iRNA can be delivered to bone marrow, liver (e.g., hepatocyes of liver), lymph glands, spleen, lungs (e.g., pleura of lungs) or spine. In one embodiment, the iRNA is delivered to bone marrow.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245) Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin Application of liposomes containing interferon to guinea pig skin resulted in a reduction of skin herpes sores while delivery of interferon via other means (e.g., as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin Results indicated that such non-ionic liposomal systems were effective in facilitating the deposition of cyclosporin-A into different layers of the skin (Hu et al. S. T. P. *Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{1215G}$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.). Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Nucleic Acid Lipid Particles

In one embodiment, a LECT2 dsRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N, N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis (2-hydroxydodecyl)amino)ethyl)(2-hydroxydodecyl)amino) ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In some embodiments, the iRNA is formulated in a lipid nanoparticle (LNP).

LNP01

In one embodiment, the lipidoid ND98.4HCl (MW 1487) (see U.S. patent application Ser. No. 12/056,230, filed Mar. 26, 2008, which is herein incorporated by reference), Cholesterol (Sigma-Aldrich), and PEG-Ceramide C16 (Avanti Polar Lipids) can be used to prepare lipid-dsRNA nanoparticles (e.g., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

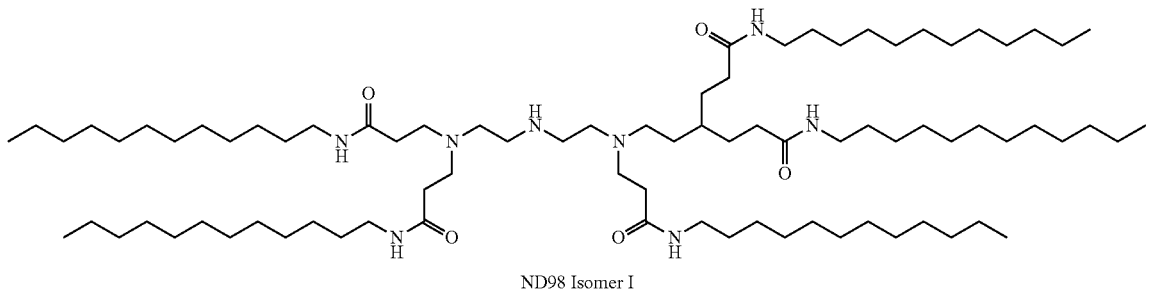

Formula 1

ND98 Isomer I

LNP01 formulations are described, e.g., in International Application Publication No. WO 2008/042973, which is hereby incorporated by reference.

Additional exemplary lipid-dsRNA formulations are provided in the following table.

TABLE 4

Exemplary lipid formulations

| | Cationic Lipid | cationic lipid/non-cationic lipid/cholesterol/PEG-lipid conjugate Lipid:siRNA ratio |
|---|---|---|
| SNALP | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA~7:1 |
| S-XTP | 2,2-Dilinoleyl-4-dimethylaminoethyl-[1,3]-dioxolane (XTC) | XTC/DSPC/Cholesterol/PEG-cDMA 57.1/7.1/34.4/1.4 lipid:siRNA~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl) (2-hydroxydodecyl)amino)ethyl) piperazin-1-yl)ethylazanediyl)didodecan-2-ol (C12-200) | C12-200/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalN Ac-PEG-DSG 50/10/35/4.5/0.5 Lipid:siRNA: 11:1 |

TABLE 4-continued

Exemplary lipid formulations

| Cationic Lipid | | cationic lipid/non-cationic lipid/cholesterol/PEG-lipid conjugate Lipid:siRNA ratio |
|---|---|---|
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. 61/185,712, filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Cationic Lipids

Any of the compounds, e.g., cationic lipids and the like, used in the nucleic acid-lipid particles featured in the invention may be prepared by known organic synthesis techniques. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR', —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO—R$^x$ and —SO$_2$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR'R$^y$, —SO—R$^x$ and —SO$_n$-NR$^x$R$^y$.

"Halogen" means fluoro, chloro, bromo and iodo.

In some embodiments, the methods featured in the invention may require the use of protecting groups. Protecting group methodology is well known to those skilled in the art (see, for example, PROTECTIVE GROUPS IN ORGANIC SYNTHESIS, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In one embodiments, nucleic acid-lipid particles featured in the invention are formulated using a cationic lipid of formula A:

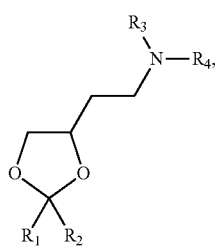

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

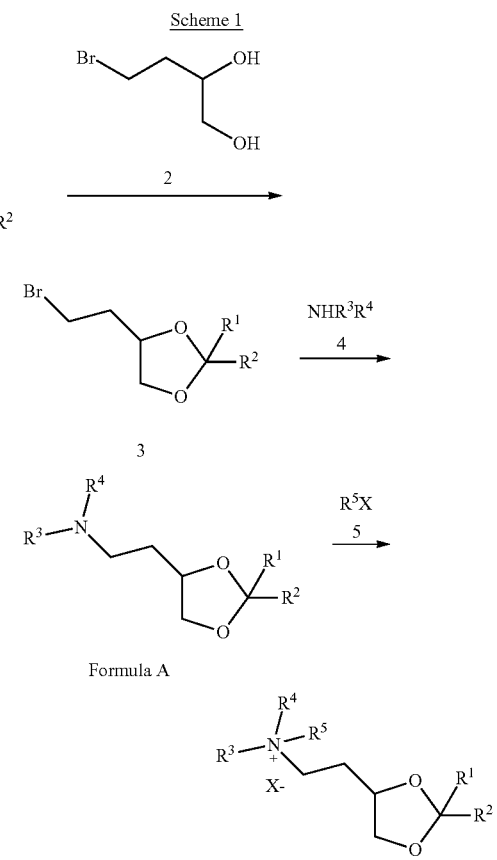

Lipid A, where R$_1$ and R$_2$ are independently alkyl, alkenyl or alkynyl, each can be optionally substituted, and R$_3$ and R$_4$ are independently lower alkyl or R$_3$ and R$_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

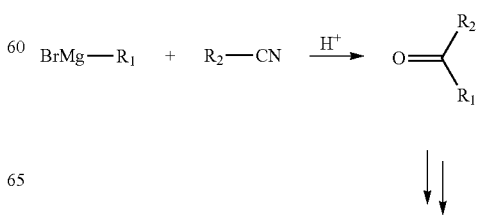

-continued

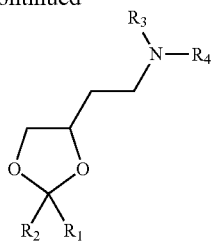

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

Synthesis of 515:

To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516:

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H] −232.3 (96.94%).

Synthesis of 517A and 517B:

The cyclopentene 516 (5 g, 0.02164 mol) was dissolved in a solution of 220 mL acetone and water (10:1) in a single neck 500 mL RBF and to it was added N-methyl morpho-

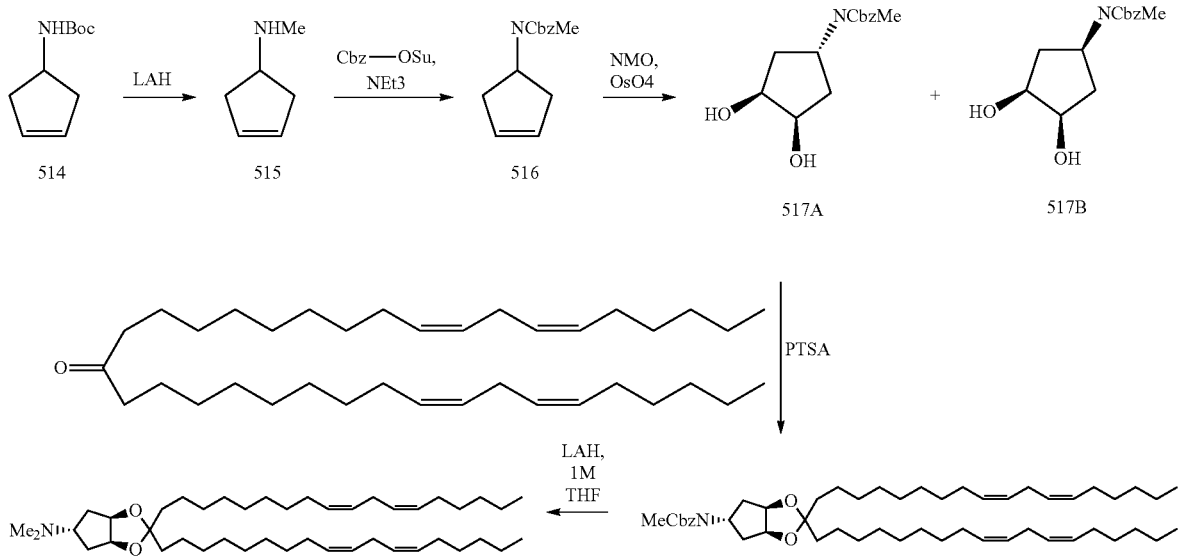

line-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (lx 50 mL) Organic phase was dried over an. Na2SO4 and solvent was removed in vacuum Silica gel column chromatographic purification of the crude material was afforded a mixture of diastereomers, which were separated by prep HPLC. Yield:—6 g crude 517A-Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H] −266.3, [M+NH4+] −283.5 present, HPLC-97.86%. Stereochemistry confirmed by X-ray.

Synthesis of 518:

Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519:

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+Calc. 654.6. Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano Z S (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations featured in the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions featured in the present invention may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Additional Formulations

Emulsions

The compositions of the present invention may be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in *Pharmaceutical Dosage Forms*, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (see e.g., Ansel's *Pharmaceutical Dosage Forms and Drug Delivery Systems*, Allen, L V., Popovich N G., and Ansel H C., 2004, Lippincott Williams & Wilkins (8th ed.), New York, N.Y.; Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's *Pharmaceutical Dosage Forms and Drug Delivery Systems*, Allen, L V., Popovich N G., and Ansel H C., 2004, Lippincott Williams & Wilkins (8th ed.), New York, N.Y.; Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (see e.g., Ansel's *Pharmaceutical Dosage Forms and Drug Delivery Systems*, Allen, L V., Popovich N G., and Ansel H C., 2004, Lippincott Williams & Wilkins (8th ed.), New York, N.Y. Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's *Pharmaceutical Dosage Forms and Drug Delivery Systems*, Allen, L V., Popovich N G., and Ansel H C., 2004, Lippincott Williams & Wilkins (8th ed.), New York, N.Y.; Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's *Pharmaceutical Dosage Forms* and Drug Delivery Systems, Allen, L V., Popovich N G., and Ansel H C., 2004, Lippincott Williams & Wilkins (8th ed.), New York, N.Y.; Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of iRNAs and nucleic acids are formulated as microemulsions. A microemulsion may be defined as a system of water, oil and amphiphile which is a single optically isotropic and thermodynamically stable liquid solution (see e.g., Ansel's *Pharmaceutical Dosage Forms and Drug Delivery Systems*, Allen, LV., Popovich N G., and Ansel H C., 2004, Lippincott Williams & Wilkins (8th ed.), New York, N.Y.; Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's *Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's *Pharmaceutical Dosage Forms and Drug Delivery Systems*, Allen, L V., Popovich N G., and Ansel H C., 2004, Lippincott Williams & Wilkins (8th ed.), New York, N.Y.; Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions may form spontaneously when their components are brought together at ambient temperature. This may be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention may also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (see e.g., Malmsten, M. Surfactants and polymers in drug delivery, *Informa Health Care,* New York, N.Y., 2002; Lee et al., *Critical Reviews in Therapeutic Drug Carrier Systems,* 1991, p. 92). Each of the above mentioned classes of penetration enhancers are described below in greater detail.

Surfactants:

In connection with the present invention, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., *Critical Reviews in Therapeutic Drug Carrier Systems,* 1991, p. 92); and perfluorochemical emulsions, such as FC-43. Takahashi et al., *J. Pharm. Pharmacol.,* 1988, 40, 252).

Fatty Acids:

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. *Enhancement in Drug Delivery,* CRC Press, Danvers, Mass., 2006; Lee et al., *Critical Reviews in Therapeutic Drug Carrier Systems,* 1991, p. 92; Muranishi, *Critical Reviews in Therapeutic Drug Carrier Systems,* 1990, 7, 1-33; El Hariri et al., *J. Pharm. Pharmacol.,* 1992, 44, 651-654).

Bile Salts:

The physiological role of bile includes the facilitation of dispersion and absorption of lipids and fat-soluble vitamins (see e.g., Malmsten, M. Surfactants and polymers in drug delivery, *Informa Health Care,* New York, N.Y., 2002; Brunton, Chapter 38 in: Goodman & Gilman's *The Pharmacological Basis of Therapeutics,* 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, *Informa Health Care,* New York, N.Y., 2002; Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1-33; Yamamoto et al., *J. Pharm. Exp. Ther.,* 1992, 263, 25; Yamashita et al., *J. Pharm. Sci.,* 1990, 79, 579-583).

Chelating Agents:

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of β-diketones (enamines)(see e.g., Katdare, A. et al., *Excipient development for pharmaceutical, biotechnology, and drug delivery,* CRC Press, Danvers, Mass., 2006; Lee et al., *Critical Reviews in Therapeutic Drug Carrier Systems,* 1991, page 92; Muranishi, *Critical Reviews in Therapeutic Drug Carrier Systems,* 1990, 7, 1-33; Buur et al., *J. Control Rel.,* 1990, 14, 43-51).

Non-Chelating Non-Surfactants:

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, *Critical Reviews in Therapeutic Drug Carrier Systems*, 1990, 7, 1-33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of iRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass' D1 Transfection Reagent (New England Biolabs; Ipswich, Mass., USA), LyoVec™/LipoGen™ (Invivogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., *DsRNA Res. Dev.*, 1995, 5, 115-121; Takakura et al., *DsRNA & Nucl. Acid Drug Dev.*, 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances that increase the viscosity of the suspension including, for example, sodium carboxymethylcellulose, sorbitol and/or dextran. The suspension may also contain stabilizers.

In some embodiments, pharmaceutical compositions featured in the invention include (a) one or more iRNA compounds and (b) one or more biologic agents which function by a non-RNAi mechanism. Examples of such biologic agents include agents that interfere with an interaction of LECT2 and at least one LECT2 binding partner.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are typical.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the iRNAs featured in the invention can be administered in combination with other known agents effective in treatment of diseases or disorders related to LECT2 expression. In any event, the administering physician can adjust the amount and timing of iRNA administration on the basis of results observed using standard measures of efficacy known in the art or described herein.

Methods of Treating Disorders Related to Expression of a LECT2 Gene

The present disclosure relates to the use of an iRNA targeting LECT2 to inhibit LECT2 expression and/or to treat a disease, disorder, or pathological process that is related to LECT2 expression.

In one aspect, a method of treatment of a disorder related to expression of LECT2 is provided, the method comprising administering an iRNA (e.g., a dsRNA) disclosed herein to a subject in need thereof. In some embodiments, the iRNA inhibits (decreases) LECT2 expression. In some embodiments, the iRNA increases LECT2 expression.

As used herein, "a disorder related to LECT2 expression," a "disease related to LECT2 expression, a "pathological process related to LECT2 expression," or the like includes any condition, disorder, or disease in which LECT2 expression is altered (e.g., decreased or increased relative to a normal level). In some embodiments, LECT2 expression is decreased. In some embodiments, LECT2 expression is increased. In embodiments, the decrease or increase in LECT2 expression is detectable in the blood (e.g., in the plasma) of the subject. In embodiments, the decrease or increase in LECT2 expression is detectable in a tissue sample from the subject (e.g., in a kidney sample or a liver sample). The decrease or increase may be assessed relative the level observed in the same individual prior to the development of the disorder or relative to other individual(s) who do not have the disorder. The decrease or increase may be limited to a particular organ, tissue, or region of the body (e.g., the kidney or the liver).

As used herein, a "subject" to be treated according to the methods described herein, includes a human or non-human animal, e.g., a mammal. The mammal may be, for example, a rodent (e.g., a rat or mouse) or a primate (e.g., a monkey). In some embodiments, the subject is a human.

A "subject in need thereof" includes a subject having, suspected of having, or at risk of developing a disorder related to LECT2 expression. In some embodiments, the subject has, or is suspected of having, a disorder related to LECT2 expression. In some embodiments, the subject is at risk of developing a disorder related to LECT2 expression.

In some embodiments, the subject is an animal that serves as a model for a disorder related to LECT2 expression, e.g., a LECT2 amyloidosis.

LECT2 Amyloidosis

In embodiments, the disorder related to LECT2 expression is an amyloidosis, e.g., a LECT2 amyloidosis. LECT2 amyloidosis has been described in several clinical studies. See, e.g., Benson, M. D. et al (2008) *Kidney International*, 74: 218-222; Murphy, C. L. et al. (2010) *Am J Kidney Dis*, 56(6):1100-1107; Larsen, C. P. et al. (2010) *Kidney Int.*, 77(9):816-819; Holanda, D. G. et al. (20011) *Nephrol. Dial. Transplant.*, 26 (1): 373-376; and Sethi, S. et al. (2012) *Kidney International* 82, 226-234 (hereinafter Sethi et al.).

Clinical and pathological features of LECT2 amyloidosis mimic those of amyloid light chain (AL) amyloidosis. These symptoms include, e.g., symptoms of kidney disease and renal failure, e.g., fluid retention, swelling, and shortness of breath. Amyloidosis may affect the heart, peripheral nervous system, gastrointestinal tract, blood, lungs and skin. Heart complications include, e.g., heart failure and irregular heart beat. Other symptoms include, e.g., stroke, gastrointestinal disorders, enlarged liver, diminished spleen function, diminished function of the adrenal and other endocrine glands, skin color change or growths, lung problems, bleeding and bruising problems, fatigue and weight loss. In embodiments, the methods described herein are associated with improvement in one or more symptoms described herein.

Methods for diagnosis of amyloidosis, e.g., LECT2 amyloidosis, are described, e.g., in Leung, N. et al. (2010) *Blood*, published online Sep. 4, 2012; DOI 10.1182/blood-2012-03-413682; Shiller, S. M. et al. (2011). Laboratory Methods for the Diagnosis of Hereditary Amyloidoses, Amyloidosis—Mechanisms and Prospects for Therapy, Dr. Svetlana Sarantseva (Ed.), ISBN: 978-953-307-253-1; Sethi et al. (see above) and in U.S. Patent Application Publication No. 20100323381.

Based on the results provided by Sethi et al., LECT2 amyloidosis accounts for a significant percentage of cases of renal amyloidosis. See Table 1 of Sethi et al., which shows that 26 out of 127 cases of renal amyloidosis studied by laser microdissection and mass spectrometry of renal biopsy and/or nephrectomy specimens were determined to be of the LECT2 amyloid type. Sethi et al. further report that apolipoprotein E protein and serum amyloid P component (SAP) were also present in all cases of LECT2 amyloidosis.

In embodiments, the amyloidosis, e.g., the LECT2 amyloidosis, involves systemic amyloid deposition. In embodiments, the amyloidosis, e.g., the LECT2 amyloidosis, is localized entirely or predominately to a particular tissue or organ (e.g., to the kidney or liver).

In embodiments, the amyloidosis, e.g., the LECT2 amyloidosis, is hereditary.

In embodiments, a LECT2 amyoidosis is diagnosed using analysis of a sample from the subject (e.g., a biopsy sample). In embodiments, the biopsy sample is a renal biopsy. In embodiments, the sample is a nephrectomy sample. In embodiments, the sample is from a liver biopsy or from other resected liver tissue. In embodiments, the sample is analyzed using methods selected from one or more of immunohistochemistry, LECT2 immunoassay, electron microscopy, laser microdissection, and mass spectrometry. In embodiments, the LECT2 amyloidosis is diagnosed using laser microdissection and mass spectrometry.

In embodiments, the amyloidosis, e.g., the LECT2 amyloidosis, affects the kidney, e.g., involves amyloid deposition in the kidney. In embodiments, kidney function is compromised as a result of the amyloidosis. In embodiments, the subject suffers from one or more of fluid retention, swelling, and shortness of breath. In embodiments, the subject has nephrotic syndrome. In embodiments, the subject suffers from proteinuria. In embodiments, the subject has renal failure.

In embodiments, the amyloidosis, e.g., the LECT2 amyloidosis, affects the liver, e.g., involves amyloid deposition in the liver. In embodiments, liver function is compromised as a result of the amyloidosis. In embodiments, the subject has hepatitis, e.g., chronic hepatitis. In embodiments, the hepatitis is a viral hepatitis.

LECT2 amyloidosis has been found to be particularly prevalent in Mexican Americans and has also been associated with homozygosity for the G allele of the LECT2 gene that encodes valine at position 40 in the mature protein (amino acid 58 in the unprocessed protein). See, e.g., Benson, M. D. et al. (2008) *Kidney International,* 74: 218-222; Murphy, C. L. et al. (2010) *Am J Kidney Dis,* 56(6):1100-1107.

In some embodiments, the subject is of Mexican descent. In some embodiments, the subject is a Mexican American.

In embodiments, the subject carries the G allele of the LECT2 gene that encodes valine at position 40 in the mature protein (amino acid 58 in the unprocessed protein). In embodiments, the subject is homozygous for the G allele (G/G genotype). In embodiments, a LECT2 protein expressed in the subject has valine at position 40 in the mature protein (or at amino acid 58 in the unprocessed protein).

In some embodiments, the method decreases LECT2 expression. In embodiments, the decrease in LECT2 expression is assessed relative to the level in the same individual prior to the treatment. In some embodiments, the method is shown to decrease LECT2 expression by comparing the levels of LECT2 expression in a treated subject (or group of subjects) with the levels in a control subject (or group of subjects), e.g., an untreated subject (or group of subjects) or a subject (or group of subjects) treated with a control treatment (e.g., an iRNA (e.g., a dsRNA) that does not target LECT2).

In embodiments, the method reduces amyloid deposition, e.g., deposition of amyloid comprising a LECT2 protein or a portion thereof. In embodiments, the protein is a wild type protein. In embodiments, the protein is a human LECT2 protein, or a portion thereof, that includes valine at position 40 (position 40 of the mature, secreted protein, or at amino acid 58 in the unprocessed protein, as described herein). In embodiments, the method decreases the size, number, and/or extent of amyloid deposits.

In embodiments, the method decreases one or more symptoms associated with amyloid deposition.

In some embodiments, the dsRNA is administered in a form that targets the dsRNA to a particular organ or tissue to inhibit amyloid deposition in the organ or tissue.

In some embodiments, the dsRNA is targeted to the liver. In some embodiments, the dsRNA is conjugated to a ligand, e.g., a GalNAc ligand (e.g., a GalNAc ligand as described herein) that targets the dsRNA to the liver (e.g., to hepatocytes).

Also provided herein is a method of reducing amyloid deposition, the method comprising administering a dsRNA as disclosed herein to a subject in need thereof (e.g., a subject having, suspected of having, or at risk for developing a LECT2 amyloidosis). In embodiments, the method decreases (e.g., prevents or diminishes) the size, number, and/or extent of amyloid deposits. The size, number, and/or extent of amyloid deposits may be assessed using any method known in the art (e.g., immunoassay, immunohistochemistry, mass spectrometry). The reduction of amyloid deposition may involve a decrease in amyloid deposition (e.g., size, number, and/or extent of amyloid deposits) of at least 5%, 10%, 15%, 20%, 25%, 30%, 35%, 40%, 45%, 50% or more.

In the methods provided herein, the iRNA (e.g., dsRNA) and compositions thereof are administered in a therapeutically effective amount. Therapeutic effects of administration of a LECT2 siRNA can be established, for example, by comparison with an appropriate control. For example, inhibition of amyloid deposition may be established, for example, in a group of patients with amyloidosis (e.g., LECT2 amyloidosis) by comparison of any appropriate parameter (e.g., a parameter assessing the size, number, or extent of amyloid deposition) with the same parameter in an appropriate control group. A control group (e.g., a group of similar individuals or the same group of individuals in a crossover design) may include, for example, an untreated population, a population that has been treated with a conventional treatment; a population that has been treated with placebo or a non-targeting iRNA; and the like.

Rheumatoid Arthritis

Rheumatoid arthritis is also a disorder related to LECT2 expression. In particular, in a Japanese population, it was found that possession of one A allele of the LECT2 gene that encodes isoleucine at position 40 in the mature protein (or amino acid 58 in the unprocessed protein) was found to increase the overall risk of developing rheumatoid arthritis. Possessing two A alleles was strongly associated with disease severity. See Kameoka, Y. et al. (2000) *Arth Rheum*, 43(6):1419-20.

In one embodiment of the methods provided herein, the disorder related to LECT2 expression is rheumatoid arthritis. In one embodiment, the dsRNA inhibits LECT2 expression in a subject having rheumatoid arthritis. In some such embodiments, the dsRNA inhibits LECT2 expression in synovial tissue and/or in synovial fluid-derived cells (e.g., mononuclear cells and fibroblasts). In some embodiments, the dsRNA targets an mRNA that encodes isoleucine at position 40 in the mature protein (amino acid 58 in the unprocessed protein).

Liver Injury

LECT2 expression can increase during acute liver injury.

In one embodiment of the methods provided herein, the disorder related to LECT2 expression is acute liver injury. In embodiments, the iRNA (e.g., dsRNA) modulates (e.g., increases or decreases) LECT2 expression. In embodiments, the iRNA modulates LECT2 expression in the liver. In embodiments, the iRNA decreases LECT2 expression in the liver. In embodiments, the iRNA increases LECT2 expression in the liver.

Combination Therapies

In embodiments, an iRNA (e.g., a dsRNA) disclosed herein is administered in combination with a second therapy (e.g., one or more additional therapies) known to be effective in treating a disorder related to LECT2 expression (e.g., a LECT2 amyloidosis) or a symptom of such a disorder. The iRNA may be administered before, after, or concurrent with the second therapy. In embodiments, the iRNA is administered before the second therapy. In embodiments, the iRNA is administered after the second therapy. In embodiments, the iRNA is administered concurrent with the second therapy.

The second therapy may be an additional therapeutic agent. The iRNA and the additional therapeutic agent can be administered in combination in the same composition or the additional therapeutic agent can be administered as part of a separate composition.

In some embodiments, the second therapy is a non-iRNA therapeutic agent that is effective to treat the disorder or symptoms of the disorder.

In some embodiments, the disorder to be treated by the compositions or methods disclosed herein is a LECT2 amyloidosis that affects kidney function, e.g., through amyloid deposition in the kidney. In some such embodiments, the iRNA is administered in conjunction with a therapy that supports kidney function (e.g., dialysis, a diuretic, an angiotensin converting enzyme (ACE) inhibitor, an angiotensin receptor blocker (ARB), or dialysis).

In some embodiments, the disorder to be treated by the compositions or methods disclosed herein is a LECT2 amyloidosis involving amyloid deposits in the liver. In some such embodiments, the iRNA is administered in conjunction with a therapy that supports liver function.

In some embodiments, the disorder to be treated by the compositions or methods disclosed herein is a LECT2 amyloidosis, and the iRNA is administered in conjunction with removal of all or part of the organ(s) affected by the amyloidosis (e.g., resection of all or part of kidney or liver tissue affected by the amyloidosis). The removal is optionally conducted in conjunction with a replacement of all or part of the organ removed (e.g., in conjunction with a kidney or liver organ transplant).

Administration Dosages, Routes, and Timing

A subject (e.g., a human subject, e.g., a patient) can be administered a therapeutic amount of iRNA. The therapeutic amount can be, e.g., 0.05-50 mg/kg. For example, the therapeutic amount can be 0.05, 0.1, 0.2, 0.3, 0.4, 0.5, 0.6, 0.7, 0.8, 0.9, 1.0, 1.5, 2.0, or 2.5, 3.0, 3.5, 4.0, 4.5, 5, 10, 15, 20, 25, 30, 35, 40, 45, or 50 mg/kg dsRNA.

In some embodiments, the iRNA is formulated for delivery to a target organ, e.g., to the liver.

In some embodiments, the iRNA is formulated as a lipid formulation, e.g., an LNP formulation as described herein. In some such embodiments, the therapeutic amount is 0.05-5 mg/kg, e.g., 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mg/kg dsRNA. In some embodiments, the lipid formulation, e.g., LNP formulation, is administered intravenously. In embodiments, the iRNA (e.g., dsRNA) is formulated as an LNP formulation and is administered (e.g., intravenously administered) at a dose of 0.1 to 0.5 mg/kg.

In some embodiments, the iRNA is administered by intravenous infusion over a period of time, such as over a 5 minute, 10 minute, 15 minute, 20 minute, or 25 minute period.

In some embodiments, the iRNA is in the form of a GalNAc conjugate as described herein. In some such embodiments, the therapeutic amount is 0.5-50 mg, e.g., 0.5, 0.6, 0.7, 0.8, 0.9, 1.0, 1.5, 2.0, 2.5, 3.0, 3.5, 4.0, 4.5, 5.0, 6, 7, 8, 9, 10, 15, 20, 25, 30, 35, 40, 45, or 50 mg/kg dsRNA. In some embodiments, the GalNAc conjugate is administered subcutaneously. In embodiments, the iRNA (e.g., dsRNA) is in the form of a GalNAc conjugate and is administered (e.g., subcutaneously administered) at a dose of 1 to 10 mg/kg.

In some embodiments, the administration is repeated, for example, on a regular basis, such as, daily, biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer.

In some embodiments, the iRNA agent is administered in two or more doses. In some embodiments, the number or amount of subsequent doses is dependent on the achievement of a desired effect, e.g., inhibition of amyloid deposition, or the achievement of a therapeutic or prophylactic effect, e.g., reduction or prevention of one or more symptoms associated with the disorder.

In some embodiments, the iRNA agent is administered according to a schedule. For example, the iRNA agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly. In embodiments, the iRNA agent is administered at the frequency required to achieve a desired effect.

In embodiments, the schedule involves closely spaced administrations followed by a longer period of time during which the agent is not administered. For example, the schedule may involve an initial set of doses that are administered in a relatively short period of time (e.g., about every 6 hours, about every 12 hours, about every 24 hours, about every 48 hours, or about every 72 hours) followed by a longer time period (e.g., about 1 week, about 2 weeks, about 3 weeks, about 4 weeks, about 5 weeks, about 6 weeks, about 7 weeks, or about 8 weeks) during which the iRNA agent is not administered. In one embodiment, the iRNA agent is initially administered hourly and is later administered at a longer interval (e.g., daily, weekly, biweekly, or monthly). In another embodiment, the iRNA agent is initially administered daily and is later administered at a longer interval (e.g., weekly, biweekly, or monthly). In certain embodiments, the longer interval increases over time or is determined based on the achievement of a desired effect.

Before administration of a full dose of the iRNA, patients can be administered a smaller dose, such as a 5% infusion dose, and monitored for adverse effects, such as an allergic reaction, or for elevated lipid levels or blood pressure. In another example, the patient can be monitored for unwanted effects.

Methods for Modulating Expression of a LECT2 Gene

In yet another aspect, the invention provides a method for modulating (e.g., inhibiting or activating) the expression of LECT2 gene, e.g., in a cell or in a subject. In some embodiments, the cell is ex vivo, in vitro, or in vivo. In some embodiments, the cell is in the liver (e.g., a hepatocyte). In some embodiments, the cell is in a subject (e.g., a mammal, such as, for example, a human) In some embodiments, the subject (e.g., the human) is at risk, or is diagnosed with a disorder related to expression of LECT2 expression, as described herein.

In one embodiment, the method includes contacting the cell with an iRNA as described herein, in an amount effective to decrease the expression of a LECT2 gene in the cell.

"Contacting," as used herein, includes directly contacting a cell, as well as indirectly contacting a cell. For example, a cell within a subject may be contacted when a composition comprising an iRNA is administered (e.g., intravenously or subcutaneously) to the subject.

The expression of a LECT2 gene may be assessed based on the level of expression of a LECT2 mRNA, a LECT2 protein, or the level of another parameter functionally linked to the level of expression of a LECT2 gene. In some embodiments, the expression of LECT2 is inhibited by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the iRNA has an $IC_{50}$ in the range of 0.001-0.01 nM, 0.001-0.10 nM, 0.001-1.0 nM, 0.001-10 nM, 0.01-0.05 nM, 0.01-0.50 nM, 0.02-0.60 nM, 0.01-1.0 nM, 0.01-1.5 nM, 0.01-10 nM. The $IC_{50}$ value may be normalized relative to an appropriate control value, e.g., the $IC_{50}$ of a non-targeting iRNA.

In some embodiments, the method includes introducing into the cell an iRNA as described herein and maintaining the cell for a time sufficient to obtain degradation of the mRNA transcript of a LECT2 gene, thereby inhibiting the expression of the LECT2 gene in the cell.

In one embodiment, the method includes administering a composition described herein, e.g., a composition comprising an iRNA that targets LECT2, to the mammal such that expression of the target LECT2 gene is decreased, such as for an extended duration, e.g., at least two, three, four days or more, e.g., one week, two weeks, three weeks, or four weeks or longer. In some embodiments, the decrease in expression of LECT2 is detectable within 1 hour, 2 hours, 4 hours, 8 hours, 12 hours, or 24 hours of the first administration.

In another embodiment, the method includes administering a composition as described herein to a mammal such that expression of the target LECT2 gene is increased by e.g., at least 10% compared to an untreated animal. In some embodiments, the activation of LECT2 occurs over an extended duration, e.g., at least two, three, four days or more, e.g., one week, two weeks, three weeks, four weeks, or more. Without wishing to be bound by theory, an iRNA can activate LECT2 expression by stabilizing the LECT2 mRNA transcript, interacting with a promoter in the genome, and/or inhibiting an inhibitor of LECT2 expression.

The iRNAs useful for the methods and compositions featured in the invention specifically target RNAs (primary or processed) of a LECT2 gene. Compositions and methods for inhibiting the expression of a LECT2 gene using iRNAs can be prepared and performed as described elsewhere herein.

In one embodiment, the method includes administering a composition containing an iRNA, where the iRNA includes a nucleotide sequence that is complementary to at least a part of an RNA transcript of the LECT2 gene of the subject, e.g., the mammal, e.g., the human, to be treated. The composition may be administered by any appropriate means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration.

In certain embodiments, the composition is administered by intravenous infusion or injection. In some such embodiments, the composition comprises a lipid formulated siRNA (e.g., an LNP formulation, such as an LNP11 formulation) for intravenous infusion.

In other embodiments, the composition is administered subcutaneously. In some such embodiments, the composition comprises an iRNA conjugated to a GalNAc ligand. In some such embodiments, the ligand targets the iRNA to the liver (e.g., to hepatocytes).

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. LECT2 siRNA

Nucleic acid sequences provided herein are represented using standard nomenclature. See the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| (Chd) | 2'-O-hexadecyl-cytidine-3'-phosphate |
| (Chds) | 2'-O-hexadecyl-cytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tb | beta-L-thymidine-3'-phosphate |
| Tbs | beta-L-thymidine-3'-phosphorothioate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Ub | beta-L-uridine-3'-phosphate |
| Ubs | beta-L-uridine-3'-phosphorothioate |
| Uf | 2'-fluorouridine-3'-phosphate |
| Ufs | 2'-fluorouridine-3'-phosphorothioate |
| (Uhd) | 2'-O-hexadecyl-uridine-3'-phosphate |
| (Uhds) | 2'-O-hexadecyl-uridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96[1] | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |

[1] The chemical structure of L96 is as follows:

TABLE 1-continued

Abbreviations of nucleotide monomers used in nucleic acid sequence representation. It will be understood that these monomers, when present in an oligonucleotide, are mutually linked by 5'-3'-phosphodiester bonds.

Abbreviation     Nucleotide(s)

Triantennary GalNAc

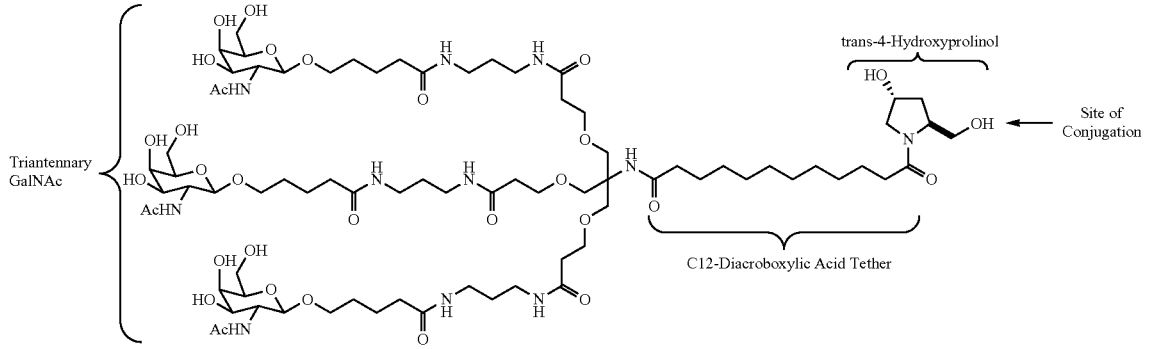

Experimental Methods

Bioinformatics

Transcripts siRNA design was carried out to identify siRNAs targeting human, cynomolgus monkey (*Macaca fascicularis*; henceforth "cyno"), mouse, and rat LECT2 transcripts. Design used the following transcripts from the NCBI RefSeq collection, annotated in the NCBI Gene database: Human, NM_002302.2; mouse, NM_010702.1; rat, NM_001108405.1. For cyno, design used a transcript sequenced from a liver-derived cDNA library. Due to high primate/rodent sequence divergence, siRNA duplexes were designed in several separate batches, including but not limited to batches containing duplexes matching human and cyno transcripts only; human, cyno, and mouse transcripts only; and human, cyno, mouse, and rat transcripts only. Most siRNA duplexes were designed that shared 100% identity in the designated region with the listed human transcript and other species transcripts considered in each design batch (above). In some instances, mismatches between duplex and mRNA target were allowed at the first antisense (last sense) position when the antisense strand: target mRNA complementary basepair was a GC or CG pair (see Table 3, oligos with label G21U, G21A, C21A). In these cases, duplexes were designed with UA or AU pairs at the first antisense:last sense pair. Thus the duplexes maintained complementarity but were mismatched with respect to target (U:C, U:G, A:C, or A:G).

siRNA Design, Specificity, and Efficacy Prediction

The predicted specificity of all possible 19mers was predicted from each sequence. Candidate 19mers were then selected that lacked repeats longer than 7 nucleotides. These 353 candidate human/cyno, 24 human/cyno/mouse, and 10 human/cyno/mouse/rat siRNAs were used in comprehensive searches against the appropriate transcriptomes (defined as the set of NM_ and XM_ records within the human, cyno, mouse, or rat NCBI Refseq sets) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start is used to create 2 heptamers and one octomer. A 'heptamer1' was created by adding a 3' A to the hexamer; we create heptamer2 by adding a 5' A to the hexamer; we create the octomer by adding an A to both 5' and 3' ends of the hexamer. The frequency of octomers and heptamers in the human, cyno, mouse, or rat 3'UTRome (defined as the subsequence of the transcriptome from NCBI's Refseq database where the end of the coding region, the 'CDS', is clearly defined) was pre-calculated. The octomer frequency was normalized to the heptamer frequency using the median value from the range of octomer frequencies. A 'mirSeedScore' was then calculated by calculating the sum of ((3×normalized octomer count)+(2× heptamer2 count)+(1×heptamer1 count)).

Both siRNA strands were assigned to a category of specificity according to the calculated scores: a score above 3 qualifies as highly specific, equal to 3 as specific and between 2.2 and 2.8 as moderately specific. The duplexes were sorted by the specificity of the antisense strand, and then moderately (or higher) specific duplexes whose antisense oligos possessed characteristics of duplexes with high predicted efficacy, including maximal UA content in the seed region and low overall GC content, were selected. 23 human/cyno/mouse sense:antisense oligo pairs, including 6 where the first antisense position was swapped to UA (above), were selected. Similarly, 24 human/cyno, and 5 human/cyno/mouse/rat, oligo pairs were selected. The selected antisense oligos were then extended to 23 nucleotides in length, and sense oligos to 21 nucleotides in length. The 48 oligo pairs that still fully matched at least human and cyno transcripts (excluding the first position for UA-swapped sequences) were then selected for synthesis and annealing into duplexes. (Table 3)

We also selected a set of 198 pairs of 19mer oligos that matched at least the human LECT2 transcript. These were selected to have at least one mismatch to all other annotated human transcripts, and possess good predicted efficacy as above. (Table 2)

TABLE 2

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 2 | 3 | NM_002302.2_1-19_s | 1 | AAAUCAAAUAGCUAUCCAU | AUGGAUAGCUAUUUGAUUU |
| 4 | 5 | NM_002302.2_7-25_s | 7 | AAUAGCUAUCCAUGGAAUA | UAUUCCAUGGAUAGCUAUU |
| 6 | 7 | NM_002302.2_13-31_s | 13 | UAUCCAUGGAAUAUUAGAA | UUCUAAUAUUCCAUGGAUA |
| 8 | 9 | NM_002302.2_18-36_s | 18 | AUGGAAUAUUAGAACUUGA | UCAAGUUCUAAUAUUCCAU |
| 10 | 11 | NM_002302.2_21-39_s | 21 | GAAUAUUAGAACUUGACUU | AAGUCAAGUUCUAAUAUUC |
| 12 | 13 | NM_002302.2_28-46_s | 28 | AGAACUUGACUUGCUCCAU | AUGGAGCAAGUCAAGUUCU |
| 14 | 15 | NM_002302.2_29-47_s | 29 | GAACUUGACUUGCUCCAUC | GAUGGAGCAAGUCAAGUUC |
| 16 | 17 | NM_002302.2_34-52_s | 34 | UGACUUGCUCCAUCCUCUU | AAGAGGAUGGAGCAAGUCA |
| 18 | 19 | NM_002302.2_43-61_s | 43 | CCAUCCUCUUAAACUUUUU | AAAAAGUUUAAGAGGAUGG |
| 20 | 21 | NM_002302.2_47-65_s | 47 | CCUCUUAAACUUUUUGUGU | ACACAAAAAGUUUAAGAGG |
| 22 | 23 | NM_002302.2_49-67_s | 49 | UCUUAAACUUUUUGUGUCU | AGACACAAAAAGUUUAAGA |
| 24 | 25 | NM_002302.2_56-74_s | 56 | CUUUUUGUGUCUCACACUA | UAGUGUGAGACACAAAAAG |
| 26 | 27 | NM_002302.2_62-80_s | 62 | GUGUCUCACACUAAAGAAA | UUUCUUUAGUGUGAGACAC |
| 28 | 29 | NM_002302.2_67-85_s | 67 | UCACACUAAAGAAAUGAGA | UCUCAUUUCUUUAGUGUGA |
| 30 | 31 | NM_002302.2_69-87_s | 69 | ACACUAAAGAAAUGAGAGA | UCUCUCAUUUCUUUAGUGU |
| 32 | 33 | NM_002302.2_76-94_s | 76 | AGAAAUGAGAGAUGCAGAA | UUCUGCAUCUCUCAUUUCU |
| 34 | 35 | NM_002302.2_82-100_s | 82 | GAGAGAUGCAGAAUUCUAA | UUAGAAUUCUGCAUCUCUC |
| 36 | 37 | NM_002302.2_87-105_s | 87 | AUGCAGAAUUCUAAGGCUA | UAGCCUUAGAAUUCUGCAU |
| 38 | 39 | NM_002302.2_92-110_s | 92 | GAAUUCUAAGGCUAAAUAG | CUAUUUAGCCUUAGAAUUC |
| 40 | 41 | NM_002302.2_95-113_s | 95 | UUCUAAGGCUAAAUAGCUA | UAGCUAUUUAGCCUUAGAA |
| 42 | 43 | NM_002302.2_103-121_s | 103 | CUAAAUAGCUAGGAAGUAU | AUACUUCCUAGCUAUUUAG |
| 44 | 45 | NM_002302.2_107-125_s | 107 | AUAGCUAGGAAGUAUUCAU | AUGAAUACUUCCUAGCUAU |
| 46 | 47 | NM_002302.2_114-132_s | 114 | GGAAGUAUUCAUUCAAACU | AGUUUGAAUGAAUACUUCC |
| 48 | 49 | NM_002302.2_123-141_s | 123 | CAUUCAAACUUGAAUAUUC | GAAUAUUCAAGUUUGAAUG |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 50 | 51 | NM_002302.2_131-149_s | 131 | CUUGAAUAUUCUUCAAAGA | UCUUUGAAGAAUAUUCAAG |
| 52 | 53 | NM_002302.2_141-159_s | 141 | CUUCAAAGAGAGUGUGGGG | CCCCACACUCUCUUUGAAG |
| 54 | 55 | NM_002302.2_144-162_s | 144 | CAAAGAGAGUGUGGGGGCA | UGCCCCCACACUCUCUUUG |
| 56 | 57 | NM_002302.2_152-170_s | 152 | GUGUGGGGGCAACUCUAAU | AUUAGAGUUGCCCCCACAC |
| 58 | 59 | NM_002302.2_156-174_s | 156 | GGGGGCAACUCUAAUCAGA | UCUGAUUAGAGUUGCCCCC |
| 60 | 61 | NM_002302.2_162-180_s | 162 | AACUCUAAUCAGAGGAAGA | UCUUCCUCUGAUUAGAGUU |
| 62 | 63 | NM_002302.2_168-186_s | 168 | AAUCAGAGGAAGAAACUAA | UUAGUUUCUUCCUCUGAUU |
| 64 | 65 | NM_002302.2_169-187_s | 169 | AUCAGAGGAAGAAACUAAA | UUUAGUUUCUUCCUCUGAU |
| 66 | 67 | NM_002302.2_178-196_s | 178 | AGAAACUAAAGGAAGUAAA | UUUACUUCCUUUAGUUUCU |
| 68 | 69 | NM_002302.2_179-197_s | 179 | GAAACUAAAGGAAGUAAAA | UUUUACUUCCUUUAGUUUC |
| 70 | 71 | NM_002302.2_184-202_s | 184 | UAAAGGAAGUAAAACCAGA | UCUGGUUUUACUUCCUUUA |
| 72 | 73 | NM_002302.2_190-208_s | 190 | AAGUAAAACCAGAUGUUUU | AAAACAUCUGGUUUUACUU |
| 74 | 75 | NM_002302.2_198-216_s | 198 | CCAGAUGUUUUCCACCAAA | UUUGGUGGAAAACAUCUGG |
| 76 | 77 | NM_002302.2_199-217_s | 199 | CAGAUGUUUUCCACCAAAG | CUUUGGUGGAAAACAUCUG |
| 78 | 79 | NM_002302.2_208-226_s | 208 | UCCACCAAAGCCCUCCUUU | AAAGGAGGGCUUUGGUGGA |
| 80 | 81 | NM_002302.2_209-227_s | 209 | CCACCAAAGCCCUCCUUUU | AAAAGGAGGGCUUUGGUGG |
| 82 | 83 | NM_002302.2_218-236_s | 218 | CCCUCCUUUUGGCUGGUCU | AGACCAGCCAAAAGGAGGG |
| 84 | 85 | NM_002302.2_228-246_s | 228 | GGCUGGUCUGAUUUCUACC | GGUAGAAAUCAGACCAGCC |
| 86 | 87 | NM_002302.2_232-250_s | 232 | GGUCUGAUUUCUACCGCAC | GUGCGGUAGAAAUCAGACC |
| 88 | 89 | NM_002302.2_237-255_s | 237 | GAUUUCUACCGCACUGGCA | UGCCAGUGCGGUAGAAAUC |
| 90 | 91 | NM_002302.2_243-261_s | 243 | UACCGCACUGGCAGGGCCA | UGGCCCUGCCAGUGCGGUA |
| 92 | 93 | NM_002302.2_245-263_s | 245 | CCGCACUGGCAGGGCCAUG | CAUGGCCCUGCCAGUGCGG |
| 94 | 95 | NM_002302.2_252-270_s | 252 | GGCAGGGCCAUGGGCUAAU | AUUAGCCCAUGGCCCUGCC |
| 96 | 97 | NM_002302.2_258-276_s | 258 | GCCAUGGGCUAAUAUAUGU | ACAUAUAUUAGCCCAUGGC |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 98 | 99 | NM_002302.2_259-277_s | 259 | CCAUGGGCUAAUAUAUGUG | CACAUAUAUUAGCCCAUGG |
| 100 | 101 | NM_002302.2_266-284_s | 266 | CUAAUAUAUGUGCUGGCAA | UUGCCAGCACAUAUAUUAG |
| 102 | 103 | NM_002302.2_271-289_s | 271 | AUAUGUGCUGGCAAGUCUU | AAGACUUGCCAGCACAUAU |
| 104 | 105 | NM_002302.2_278-296_s | 278 | CUGGCAAGUCUUCCAAUGA | UCAUUGGAAGACUUGCCAG |
| 106 | 107 | NM_002302.2_281-299_s | 281 | GCAAGUCUUCCAAUGAGAU | AUCUCAUUGGAAGACUUGC |
| 108 | 109 | NM_002302.2_286-304_s | 286 | UCUUCCAAUGAGAUCCGGA | UCCGGAUCUCAUUGGAAGA |
| 110 | 111 | NM_002302.2_293-311_s | 293 | AUGAGAUCCGGACGUGUGA | UCACACGUCCGGAUCUCAU |
| 112 | 113 | NM_002302.2_297-315_s | 297 | GAUCCGGACGUGUGACCGC | GCGGUCACACGUCCGGAUC |
| 114 | 115 | NM_002302.2_301-319_s | 301 | CGGACGUGUGACCGCCAUG | CAUGGCGGUCACACGUCCG |
| 116 | 117 | NM_002302.2_304-322_s | 304 | ACGUGUGACCGCCAUGGCU | AGCCAUGGCGGUCACACGU |
| 118 | 119 | NM_002302.2_312-330_s | 312 | CCGCCAUGGCUGUGGACAG | CUGUCCACAGCCAUGGCGG |
| 120 | 121 | NM_002302.2_315-333_s | 315 | CCAUGGCUGUGGACAGUAC | GUACUGUCCACAGCCAUGG |
| 122 | 123 | NM_002302.2_319-337_s | 319 | GGCUGUGGACAGUACUCUG | CAGAGUACUGUCCACAGCC |
| 124 | 125 | NM_002302.2_330-348_s | 330 | GUACUCUGCUCAAAGAAGU | ACUUCUUUGAGCAGAGUAC |
| 126 | 127 | NM_002302.2_334-352_s | 334 | UCUGCUCAAAGAAGUCAGA | UCUGACUUCUUUGAGCAGA |
| 128 | 129 | NM_002302.2_340-358_s | 340 | CAAAGAAGUCAGAGGCCUC | GAGGCCUCUGACUUCUUUG |
| 130 | 131 | NM_002302.2_345-363_s | 345 | AAGUCAGAGGCCUCACCAG | CUGGUGAGGCCUCUGACUU |
| 132 | 133 | NM_002302.2_351-369_s | 351 | GAGGCCUCACCAGGGUGUG | CACACCCUGGUGAGGCCUC |
| 134 | 135 | NM_002302.2_354-372_s | 354 | GCCUCACCAGGGUGUGGAC | GUCCACACCCUGGUGAGGC |
| 136 | 137 | NM_002302.2_360-378_s | 360 | CCAGGGUGUGGACAUCUUG | CAAGAUGUCCACACCCUGG |
| 138 | 139 | NM_002302.2_364-382_s | 364 | GGUGUGGACAUCUUGUGCU | AGCACAAGAUGUCCACACC |
| 140 | 141 | NM_002302.2_371-389_s | 371 | ACAUCUUGUGCUCUGCUGG | CCAGCAGAGCACAAGAUGU |
| 142 | 143 | NM_002302.2_378-396_s | 378 | GUGCUCUGCUGGAUCUACU | AGUAGAUCCAGCAGAGCAC |
| 144 | 145 | NM_002302.2_383-401_s | 383 | CUGCUGGAUCUACUGUGUA | UACACAGUAGAUCCAGCAG |

TABLE 2-continued

Human LECT2 siRNA Single Strands and Duplex Sequences

| SEQ ID NO: (sense) | SEQ ID NO: (antisense) | Oligo Name | Start Position on transcript NM_002302.2 | Sense Sequence (5'-3') | Antisense Sequence (5'-3') |
|---|---|---|---|---|---|
| 146 | 147 | NM_002302.2_388-406_s | 388 | GGAUCUACUGUGUACGCAC | GUGCGUACACAGUAGAUCC |
| 148 | 149 | NM_002302.2_392-410_s | 392 | CUACUGUGUACGCACCAUU | AAUGGUGCGUACACAGUAG |
| 150 | 151 | NM_002302.2_395-413_s | 395 | CUGUGUACGCACCAUUCAC | GUGAAUGGUGCGUACACAG |
| 152 | 153 | NM_002302.2_403-421_s | 403 | GCACCAUUCACUGGAAUGA | UCAUUCCAGUGAAUGGUGC |
| 154 | 155 | NM_002302.2_406-424_s | 406 | CCAUUCACUGGAAUGAUUG | CAAUCAUUCCAGUGAAUGG |
| 156 | 157 | NM_002302.2_413-431_s | 413 | CUGGAAUGAUUGUGGGCCA | UGGCCCACAAUCAUUCCAG |
| 158 | 159 | NM_002302.2_416-434_s | 416 | GAAUGAUUGUGGGCCAGGA | UCCUGGCCCACAAUCAUUC |
| 160 | 161 | NM_002302.2_420-438_s | 420 | GAUUGUGGGCCAGGAGAAA | UUUCUCCUGGCCCACAAUC |
| 162 | 163 | NM_002302.2_426-444_s | 426 | GGGCCAGGAGAAACCUUAU | AUAAGGUUUCUCCUGGCCC |
| 164 | 165 | NM_002302.2_430-448_s | 430 | CAGGAGAAACCUUAUCAAA | UUUGAUAAGGUUUCUCCUG |
| 166 | 167 | NM_002302.2_436-454_s | 436 | AAACCUUAUCAAACAAGA | UCUUGUUUUGAUAAGGUUU |
| 168 | 169 | NM_002302.2_442-460_s | 442 | UAUCAAACAAGAAUGCUA | UAGCAUUCUUGUUUUGAUA |
| 170 | 171 | NM_002302.2_448-466_s | 448 | AACAAGAAUGCUAUCAAUA | UAUUGAUAGCAUUCUUGUU |
| 172 | 173 | NM_002302.2_450-468_s | 450 | CAAGAAUGCUAUCAAUAAU | AUUAUUGAUAGCAUUCUUG |
| 174 | 175 | NM_002302.2_462-480_s | 462 | CAAUAAUGGUGUUCGAAUA | UAUUCGAACACCAUUAUUG |
| 176 | 177 | NM_002302.2_465-483_s | 465 | UAAUGGUGUUCGAAUAUCU | AGAUAUUCGAACACCAUUA |
| 178 | 179 | NM_002302.2_471-489_s | 471 | UGUUCGAAUAUCUGGAAGA | UCUUCCAGAUAUUCGAACA |
| 180 | 181 | NM_002302.2_478-496_s | 478 | AUAUCUGGAAGAGGUUUUU | AAAAACCUCUUCCAGAUAU |
| 182 | 183 | NM_002302.2_480-498_s | 480 | AUCUGGAAGAGGUUUUUGU | ACAAAACCUCUUCCAGAU |
| 184 | 185 | NM_002302.2_487-505_s | 487 | AGAGGUUUUUGUGUCAAAA | UUUUGACACAAAAACCUCU |
| 186 | 187 | NM_002302.2_490-508_s | 490 | GGUUUUUGUGUCAAAAUGU | ACAUUUUGACACAAAAACC |
| 188 | 189 | NM_002302.2_497-515_s | 497 | GUGUCAAAAUGUUCUACAU | AUGUAGAACAUUUUGACAC |
| 190 | 191 | NM_002302.2_500-518_s | 500 | UCAAAAUGUUCUACAUUAA | UUAAUGUAGAACAUUUUGA |
| 192 | 193 | NM_002302.2_506-524_s | 506 | UGUUCUACAUUAAGCCAAU | AUUGGCUUAAUGUAGAACA |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 194 | 195 | NM_002302.2_528-546_s | 528 | GUAUAAAGGUCCUAUUAAG | CUUAAUAGGACCUUUAUAC |
| 196 | 197 | NM_002302.2_529-547_s | 529 | UAUAAAGGUCCUAUUAAGA | UCUUAAUAGGACCUUUAUA |
| 198 | 199 | NM_002302.2_538-556_s | 538 | CCUAUUAAGAAGGGAGAAA | UUUCUCCCUUCUUAAUAGG |
| 200 | 201 | NM_002302.2_539-557_s | 539 | CUAUUAAGAAGGGAGAAAA | UUUUCUCCCUUCUUAAUAG |
| 202 | 203 | NM_002302.2_544-562_s | 544 | AAGAAGGGAGAAAACUUG | CAAGUUUUCUCCCUUCUU |
| 204 | 205 | NM_002302.2_552-570_s | 552 | AGAAAACUUGGAACUCUA | UAGAGUUCCAAGUUUUUCU |
| 206 | 207 | NM_002302.2_555-573_s | 555 | AAACUUGGAACUCUAUUG | CAAUAGAGUUCCAAGUUUU |
| 208 | 209 | NM_002302.2_559-577_s | 559 | CUUGGAACUCUAUUGCCCU | AGGGCAAUAGAGUUCCAAG |
| 210 | 211 | NM_002302.2_566-584_s | 566 | CUCUAUUGCCCUUGCAGAA | UUCUGCAAGGGCAAUAGAG |
| 212 | 213 | NM_002302.2_573-591_s | 573 | GCCCUUGCAGAAAGUUUAU | AUAAACUUUCUGCAAGGGC |
| 214 | 215 | NM_002302.2_574-592_s | 574 | CCCUUGCAGAAAGUUUAUC | GAUAAACUUUCUGCAAGGG |
| 216 | 217 | NM_002302.2_581-599_s | 581 | AGAAAGUUUAUCCUGGCAU | AUGCCAGGAUAAACUUUCU |
| 218 | 219 | NM_002302.2_585-603_s | 585 | AGUUUAUCCUGGCAUACAA | UUGUAUGCCAGGAUAAACU |
| 220 | 221 | NM_002302.2_592-610_s | 592 | CCUGGCAUACAAUCGCAUG | CAUGCGAUUGUAUGCCAGG |
| 222 | 223 | NM_002302.2_598-616_s | 598 | AUACAAUCGCAUGUGCACA | UGUGCACAUGCGAUUGUAU |
| 224 | 225 | NM_002302.2_603-621_s | 603 | AUCGCAUGUGCACAUUGAA | UUCAAUGUGCACAUGCGAU |
| 226 | 227 | NM_002302.2_606-624_s | 606 | GCAUGUGCACAUUGAAAAC | GUUUUCAAUGUGCACAUGC |
| 228 | 229 | NM_002302.2_611-629_s | 611 | UGCACAUUGAAAACUGUGA | UCACAGUUUUCAAUGUGCA |
| 230 | 231 | NM_002302.2_616-634_s | 616 | AUUGAAAACUGUGACUCGA | UCGAGUCACAGUUUUCAAU |
| 232 | 233 | NM_002302.2_620-638_s | 620 | AAAACUGUGACUCGAGUGA | UCACUCGAGUCACAGUUUU |
| 234 | 235 | NM_002302.2_625-643_s | 625 | UGUGACUCGAGUGACCCUA | UAGGGUCACUCGAGUCACA |
| 236 | 237 | NM_002302.2_633-651_s | 633 | GAGUGACCCUACUGCAUAC | GUAUGCAGUAGGGUCACUC |
| 238 | 239 | NM_002302.2_637-655_s | 637 | GACCCUACUGCAUACCUGU | ACAGGUAUGCAGUAGGGUC |
| 240 | 241 | NM_002302.2_640-658_s | 640 | CCUACUGCAUACCUGUAAA | UUUACAGGUAUGCAGUAGG |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 242 | 243 | NM_002302.2_644-662_s | 644 | CUGCAUACCUGUAAAUCGA | UCGAUUUACAGGUAUGCAG |
| 244 | 245 | NM_002302.2_651-669_s | 651 | CCUGUAAAUCGAAGGCCAA | UUGGCCUUCGAUUUACAGG |
| 246 | 247 | NM_002302.2_657-675_s | 657 | AAUCGAAGGCCAAUGGUCA | UGACCAUUGGCCUUCGAUU |
| 248 | 249 | NM_002302.2_663-681_s | 663 | AGGCCAAUGGUCAGAUCUU | AAGAUCUGACCAUUGGCCU |
| 250 | 251 | NM_002302.2_667-685_s | 667 | CAAUGGUCAGAUCUUCAAA | UUUGAAGAUCUGACCAUUG |
| 252 | 253 | NM_002302.2_674-692_s | 674 | CAGAUCUUCAAAAUAAAAA | UUUUUAUUUUGAAGAUCUG |
| 254 | 255 | NM_002302.2_686-704_s | 686 | AUAAAAGUCAUCUUAAAA | UUUUAAGAUGACUUUUUAU |
| 256 | 257 | NM_002302.2_691-709_s | 691 | AAGUCAUCUUAAAACCUG | CAGGUUUUAAGAUGACUU |
| 258 | 259 | NM_002302.2_698-716_s | 698 | CUUAAAACCUGGAUGCAU | AUGCAUCCAGGUUUUUAAG |
| 260 | 261 | NM_002302.2_699-717_s | 699 | UUAAAACCUGGAUGCAUA | UAUGCAUCCAGGUUUUUAA |
| 262 | 263 | NM_002302.2_706-724_s | 706 | CCUGGAUGCAUACCCUUCU | AGAAGGGUAUGCAUCCAGG |
| 264 | 265 | NM_002302.2_709-727_s | 709 | GGAUGCAUACCCUUCUCUU | AAGAGAAGGGUAUGCAUCC |
| 266 | 267 | NM_002302.2_716-734_s | 716 | UACCCUUCUCUUCAAGAAA | UUUCUUGAAGAGAAGGGUA |
| 268 | 269 | NM_002302.2_719-737_s | 719 | CCUUCUCUUCAAGAAAUUU | AAAUUUCUUGAAGAGAAGG |
| 270 | 271 | NM_002302.2_728-746_s | 728 | CAAGAAAUUUGUGUUCACA | UGUGAACACAAAUUUCUUG |
| 272 | 273 | NM_002302.2_730-748_s | 730 | AGAAAUUUGUGUUCACAAA | UUUGUGAACACAAAUUUCU |
| 274 | 275 | NM_002302.2_736-754_s | 736 | UUGUGUUCACAAAGGAAAA | UUUUCCUUUGUGAACACAA |
| 276 | 277 | NM_002302.2_743-761_s | 743 | CACAAAGGAAAAUGCAUG | CAUGCAUUUUCCUUUGUG |
| 278 | 279 | NM_002302.2_745-763_s | 745 | CAAAGGAAAAUGCAUGAA | UUCAUGCAUUUUCCUUUG |
| 280 | 281 | NM_002302.2_750-768_s | 750 | GAAAAUGCAUGAAGGGAU | AUCCCUUCAUGCAUUUUC |
| 282 | 283 | NM_002302.2_755-773_s | 755 | AUGCAUGAAGGGAUGGAUA | UAUCCAUCCCUUCAUGCAU |
| 284 | 285 | NM_002302.2_763-781_s | 763 | AGGGAUGGAUACCCCAUUU | AAAUGGGGUAUCCAUCCCU |
| 286 | 287 | NM_002302.2_764-782_s | 764 | GGGAUGGAUACCCCAUUUU | AAAAUGGGGUAUCCAUCCC |
| 288 | 289 | NM_002302.2_773-791_s | 773 | ACCCCAUUUUCCAUGACAU | AUGUCAUGGAAAAUGGGGU |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 290 | 291 | NM_002302.2_774-792_s | 774 | CCCCAUUUUCCAUGACAUG | CAUGUCAUGGAAAAUGGGG |
| 292 | 293 | NM_002302.2_783-801_s | 783 | CCAUGACAUGAUUAUUACA | UGUAAUAAUCAUGUCAUGG |
| 294 | 295 | NM_002302.2_786-804_s | 786 | UGACAUGAUUAUUACACAU | AUGUGUAAUAAUCAUGUCA |
| 296 | 297 | NM_002302.2_792-810_s | 792 | GAUUAUUACACAUUGCAUG | CAUGCAAUGUGUAAUAAUC |
| 298 | 299 | NM_002302.2_798-816_s | 798 | UACACAUUGCAUGCCUGUA | UACAGGCAUGCAAUGUGUA |
| 300 | 301 | NM_002302.2_803-821_s | 803 | AUUGCAUGCCUGUAUCAAA | UUUGAUACAGGCAUGCAAU |
| 302 | 303 | NM_002302.2_804-822_s | 804 | UUGCAUGCCUGUAUCAAAA | UUUUGAUACAGGCAUGCAA |
| 304 | 305 | NM_002302.2_815-833_s | 815 | UAUCAAAACAUCUCACGUA | UACGUGAGAUGUUUUGAUA |
| 306 | 307 | NM_002302.2_823-841_s | 823 | CAUCUCACGUACCUCAUAA | UUAUGAGGUACGUGAGAUG |
| 308 | 309 | NM_002302.2_828-846_s | 828 | CACGUACCUCAUAAACAUA | UAUGUUUAUGAGGUACGUG |
| 310 | 311 | NM_002302.2_830-848_s | 830 | CGUACCUCAUAAACAUAUA | UAUAUGUUUAUGAGGUACG |
| 312 | 313 | NM_002302.2_840-858_s | 840 | AAACAUAUACACCUAUGUA | UACAUAGGUGUAUAUGUUU |
| 314 | 315 | NM_002302.2_848-866_s | 848 | ACACCUAUGUACCCACAAA | UUUGUGGGUACAUAGGUGU |
| 316 | 317 | NM_002302.2_849-867_s | 849 | CACCUAUGUACCCACAAAA | UUUUGUGGGUACAUAGGUG |
| 318 | 319 | NM_002302.2_858-876_s | 858 | ACCCACAAAAUUUUUUAA | UUAAAAAAUUUUGUGGGU |
| 320 | 321 | NM_002302.2_863-881_s | 863 | CAAAAUUUUUUAAUUAAA | UUUAAUUAAAAAAUUUUG |
| 322 | 323 | NM_002302.2_872-890_s | 872 | UUUAAUUAAAAAAGGAAA | UUUCCUUUUUUAAUUAAA |
| 324 | 325 | NM_002302.2_877-895_s | 877 | UUAAAAAAGGAAAUUUGA | UCAAAUUUCCUUUUUUAA |
| 326 | 327 | NM_002302.2_883-901_s | 883 | AAAGGAAAUUUGAGUUUAA | UUAAACUCAAAUUUCCUUU |
| 328 | 329 | NM_002302.2_886-904_s | 886 | GGAAAUUUGAGUUUAAAUA | UAUUUAAACUCAAAUUUCC |
| 330 | 331 | NM_002302.2_889-907_s | 889 | AAUUUGAGUUUAAAUAGAA | UUCUAUUUAAACUCAAAUU |
| 332 | 333 | NM_002302.2_895-913_s | 895 | AGUUUAAAUAGAAACAUGA | UCAUGUUUCUAUUUAAACU |
| 334 | 335 | NM_002302.2_899-917_s | 899 | UAAAUAGAAACAUGAUAAA | UUUAUCAUGUUUCUAUUUA |
| 336 | 337 | NM_002302.2_905-923_s | 905 | GAAACAUGAUAAAUGCAAG | CUUGCAUUUAUCAUGUUUC |

TABLE 2-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') |
|---|---|---|---|---|---|
| 338 | 339 | NM_002302.2_912-930_s | 912 | GAUAAAUGCAAGAAAGAAA | UUUCUUUCUUGCAUUUAUC |
| 340 | 341 | NM_002302.2_915-933_s | 915 | AAAUGCAAGAAAGAAACA | UGUUUUCUUUCUUGCAUUU |
| 342 | 343 | NM_002302.2_920-938_s | 920 | CAAGAAAGAAACAUUUUG | CAAAAUGUUUUCUUUCUUG |
| 344 | 345 | NM_002302.2_926-944_s | 926 | AGAAAACAUUUUGAUUUUA | UAAAAUCAAAAUGUUUUCU |
| 346 | 347 | NM_002302.2_932-950_s | 932 | CAUUUUGAUUUUAACUCAU | AUGAGUUAAAAUCAAAAUG |
| 348 | 349 | NM_002302.2_938-956_s | 938 | GAUUUUAACUCAUUGUCAC | GUGACAAUGAGUUAAAAUC |
| 350 | 351 | NM_002302.2_939-957_s | 939 | AUUUUAACUCAUUGUCACU | AGUGACAAUGAGUUAAAAU |
| 352 | 353 | NM_002302.2_948-966_s | 948 | CAUUGUCACUCUGAUGUUC | GAACAUCAGAGUGACAAUG |
| 354 | 355 | NM_002302.2_950-968_s | 950 | UUGUCACUCUGAUGUUCAU | AUGAACAUCAGAGUGACAA |
| 356 | 357 | NM_002302.2_956-974_s | 956 | CUCUGAUGUUCAUGUGAAC | GUUCACAUGAACAUCAGAG |
| 358 | 359 | NM_002302.2_960-978_s | 960 | GAUGUUCAUGUGAACUGGU | ACCAGUUCACAUGAACAUC |
| 360 | 361 | NM_002302.2_966-984_s | 966 | CAUGUGAACUGGUUGCUUC | GAAGCAACCAGUUCACAUG |
| 362 | 363 | NM_002302.2_973-991_s | 973 | ACUGGUUGCUUCGGGCUCU | AGAGCCCGAAGCAACCAGU |
| 364 | 365 | NM_002302.2_977-995_s | 977 | GUUGCUUCGGGCUCUUUGA | UCAAAGAGCCCGAAGCAAC |
| 366 | 367 | NM_002302.2_980-998_s | 980 | GCUUCGGGCUCUUUGAUCU | AGAUCAAAGAGCCCGAAGC |
| 368 | 369 | NM_002302.2_984-1002_s | 984 | CGGGCUCUUUGAUCUGUCA | UGACAGAUCAAAGAGCCCG |
| 370 | 371 | NM_002302.2_989-1007_s | 989 | UCUUUGAUCUGUCACCUAU | AUAGGUGACAGAUCAAAGA |
| 372 | 373 | NM_002302.2_994-1012_s | 994 | GAUCUGUCACCUAUGGAAU | AUUCCAUAGGUGACAGAUC |
| 374 | 375 | NM_002302.2_1001-1019_s | 1001 | CACCUAUGGAAUCUGAGUG | CACUCAGAUUCCAUAGGUG |
| 376 | 377 | NM_002302.2_1008-1026_s | 1008 | GGAAUCUGAGUGGUUUUAU | AUAAAACCACUCAGAUUCC |
| 378 | 379 | NM_002302.2_1013-1031_s | 1013 | CUGAGUGGUUUUAUUUUUU | AAAAAAUAAAACCACUCAG |
| 380 | 381 | NM_002302.2_1015-1033_s | 1015 | GAGUGGUUUUAUUUUUUAG | CUAAAAAAUAAAACCACUC |
| 382 | 383 | NM_002302.2_1019-1037_s | 1019 | GGUUUUAUUUUUUAGAUUU | AAAUCUAAAAAAUAAAACC |
| 384 | 385 | NM_002302.2_1025-1043_s | 1025 | AUUUUUUAGAUUUCUCAGU | ACUGAGAAAUCUAAAAAAU |

TABLE 2-continued

Human LECT2 siRNA Single Strands and Duplex Sequences

| SEQ ID NO: (sense) | SEQ ID NO: (antisense) | Oligo Name | Start Position on transcript NM_002302.2 | Sense Sequence (5'-3') | Antisense Sequence (5'-3') |
|---|---|---|---|---|---|
| 386 | 387 | NM_002302.2_1031-1049_s | 1031 | UAGAUUUCUCAGUCCCAAA | UUUGGGACUGAGAAAUCUA |
| 388 | 389 | NM_002302.2_1038-1056_s | 1038 | CUCAGUCCCAAAGAUCUAA | UUAGAUCUUUGGGACUGAG |
| 390 | 391 | NM_002302.2_1043-1061_s | 1043 | UCCCAAAGAUCUAAGAUAA | UUAUCUUAGAUCUUUGGGA |
| 392 | 393 | NM_002302.2_1046-1064_s | 1046 | CAAAGAUCUAAGAUAAAUA | UAUUUAUCUUAGAUCUUUG |
| 394 | 395 | NM_002302.2_1053-1071_s | 1053 | CUAAGAUAAAUAAACAAGA | UCUUGUUUAUUUAUCUUAG |
| 396 | 397 | NM_002302.2_1055-956_s | 1055 | AAGAUAAAUAAACAAGAGA | UCUCUUGUUUAUUUAUCUU |

TABLE 3

Human LECT2 siRNA Single Strands and Duplex Sequences

| SEQ ID NO: (sense) | SEQ ID NO: (antisense) | Oligo Name | Start Position on transcript NM_002302.2 | Sense Sequence (5'-3') | Antisense Sequence (5'-3') | Species[1] |
|---|---|---|---|---|---|---|
| 398 | 399 | NM_002302.2_512-534_s | 512 | AUUAAGCCAAUUAAGUAUAAA | UUUAUACUUAAUUGGCUUAAUGU | HCMR |
| 400 | 401 | NM_002302.2_511-533_s | 511 | CAUUAAGCCAAUUAAGUAUAA | UUAUACUUAAUUGGCUUAAUGUA | HCMR |
| 402 | 403 | NM_002302.2_508-530_s | 508 | CUACAUUAAGCCAAUUAAGUA | UACUUAAUUGGCUUAAUGUAGAA | HCMR |
| 404 | 405 | NM_002302.2_509-531_s | 509 | UACAUUAAGCCAAUUAAGUAU | AUACUUAAUUGGCUUAAUGUAGA | HCMR |
| 406 | 407 | NM_002302.2_510-532_s | 510 | ACAUUAAGCCAAUUAAGUAUA | UAUACUUAAUUGGCUUAAUGUAG | HCMR |
| 408 | 409 | NM_002302.2_320-342_s | 320 | UGUGGACAGUACUCUGCUCAA | UUGAGCAGAGUACUGUCCACAGC | HCM |
| 410 | 411 | NM_002302.2_515-537_s | 515 | AAGCCAAUUAAGUAUAAAGGU | ACCUUUAUACUUAAUUGGCUUAA | HCM |
| 412 | 413 | NM_002302.2_513-535_s | 513 | UUAAGCCAAUUAAGUAUAAAG | CUUUAUACUUAAUUGGCUUAAUG | HCM |
| 414 | 415 | NM_002302.2_317-339_s | 317 | GGCUGUGGACAGUACUCUGCU | AGCAGAGUACUGUCCACAGCCAU | HCM |
| 416 | 417 | NM_002302.2_319-341_s | 319 | CUGUGGACAGUACUCUGCUCA | UGAGCAGAGUACUGUCCACAGCC | HCM |
| 418 | 419 | NM_002302.2_321-343_s | 321 | GUGGACAGUACUCUGCUCAAA | UUUGAGCAGAGUACUGUCCACAG | HCM |
| 420 | 421 | NM_002302.2_318-340_s | 318 | GCUGUGGACAGUACUCUGCUC | GAGCAGAGUACUGUCCACAGCCA | HCM |
| 422 | 423 | NM_002302.2_514-536_s | 514 | UAAGCCAAUUAAGUAUAAAGG | CCUUUAUACUUAAUUGGCUUAAU | HCM |
| 424 | 425 | NM_002302.2_324-346_s | 324 | GACAGUACUCUGCUCAAAGAA | UUCUUUGAGCAGAGUACUGUCCA | HCM |

TABLE 3-continued

Human LECT2 siRNA Single Strands and Duplex Sequences

| SEQ ID NO: (sense) | SEQ ID NO: (antisense) | Oligo Name | Start Position on transcript NM_002302.2 | Sense Sequence (5'-3') | Antisense Sequence (5'-3') | Species[1] |
|---|---|---|---|---|---|---|
| 426 | 427 | NM_002302.2_323-345_s | 323 | GGACAGUACUCUGCUCAAAGA | UCUUUGAGCAGAGUACUGUCCAC | HCM |
| 428 | 429 | NM_002302.2_322-344_s | 322 | UGGACAGUACUCUGCUCAAAG | CUUUGAGCAGAGUACUGUCCACA | HCM |
| 430 | 431 | NM_002302.2_513-535_G21U_s | 513 | UUAAGCCAAUUAAGUAUAAAU | AUUUAUACUUAAUUGGCUUAAUG | HCM |
| 432 | 433 | NM_002302.2_318-340_C21A_s | 318 | GCUGUGGACAGUACUCUGCUA | UAGCAGAGUACUGUCCACAGCCA | HCM |
| 434 | 435 | NM_002302.2_514-536_G21A_s | 514 | UAAGCCAAUUAAGUAUAAAGA | UCUUUAUACUUAAUUGGCUUAAU | HCM |
| 436 | 437 | NM_002302.2_322-344_G21U_s | 322 | UGGACAGUACUCUGCUCAAAU | AUUUGAGCAGAGUACUGUCCACA | HCM |
| 438 | 439 | NM_002302.2_516-538_C21A_s | 516 | AGCCAAUUAAGUAUAAAGGUA | UACCUUUAUACUUAAUUGGCUUA | HCM |
| 440 | 441 | NM_002302.2_516-538_s | 516 | AGCCAAUUAAGUAUAAAGGUC | GACCUUUAUACUUAAUUGGCUUA | HCM |
| 442 | 443 | NM_002302.2_507-529_s | 507 | UCUACAUUAAGCCAAUUAAGU | ACUUAAUUGGCUUAAUGUAGAAC | HC |
| 444 | 445 | NM_002302.2_506-528_s | 506 | UUCUACAUUAAGCCAAUUAAG | CUUAAUUGGCUUAAUGUAGAACA | HC |
| 446 | 447 | NM_002302.2_505-527_s | 505 | GUUCUACAUUAAGCCAAUUAA | UUAAUUGGCUUAAUGUAGAACAU | HC |
| 448 | 449 | NM_002302.2_504-526_s | 504 | UGUUCUACAUUAAGCCAAUUA | UAAUUGGCUUAAUGUAGAACAUU | HC |
| 450 | 451 | NM_002302.2_314-336_s | 314 | CAUGGCUGUGGACAGUACUCU | AGAGUACUGUCCACAGCCAUGGC | HC |
| 452 | 453 | NM_002302.2_316-338_s | 316 | UGGCUGUGGACAGUACUCUGC | GCAGAGUACUGUCCACAGCCAUG | HC |
| 454 | 455 | NM_002302.2_506-528_G21A_s | 506 | UUCUACAUUAAGCCAAUUAAA | UUUAAUUGGCUUAAUGUAGAACA | HC |
| 456 | 457 | NM_002302.2_316-338_C21A_s | 316 | UGGCUGUGGACAGUACUCUGA | UCAGAGUACUGUCCACAGCCAUG | HC |
| 458 | 459 | NM_002302.2_263-285_G21A_s | 263 | GCUAAUAUAUGUGCUGGCAAA | UUUGCCAGCACAUAUAUUAGCCC | HC |
| 460 | 461 | NM_002302.2_571-593_C21A_s | 571 | GCCCUUGCAGAAAGUUUAUCA | UGAUAAACUUUCUGCAAGGGCAA | HC |
| 462 | 463 | NM_002302.2_130-152_G21A_s | 130 | UUGAAUAUUCUUCAAAGAGAA | UUCUCUUUGAAGAAUAUUCAAGU | HC |
| 464 | 465 | NM_002302.2_263-285_s | 263 | GCUAAUAUAUGUGCUGGCAAG | CUUGCCAGCACAUAUAUUAGCCC | HC |
| 466 | 467 | NM_002302.2_118-140_s | 118 | AUUCAUUCAAACUUGAAUAUU | AAUAUUCAAGUUUGAAUGAAUAC | HC |
| 468 | 469 | NM_002302.2_107-129_s | 107 | AGCUAGGAAGUAUUCAUUCAA | UUGAAUGAAUACUUCCUAGCUAU | HC |
| 470 | 471 | NM_002302.2_665-687_s | 665 | CAAUGGUCAGAUCUUCAAAAU | AUUUUGAAGAUCUGACCAUUGGC | HC |
| 472 | 473 | NM_002302.2_668-690_s | 668 | UGGUCAGAUCUUCAAAAUAAA | UUUAUUUUGAAGAUCUGACCAUU | HC |

TABLE 3-continued

Human LECT2 siRNA Single Strands and Duplex Sequences

| SEQ ID NO: (sense) | SEQ ID NO: (anti-sense) | Oligo Name | Start Position on transcript NM_002302.2 | Sense Sequence (5'-3') | Antisense Sequence (5'-3') | Species[1] |
|---|---|---|---|---|---|---|
| 474 | 475 | NM_002302.2_427-449_s | 427 | CCAGGAGAAACCUUAUCAAAA | UUUUGAUAAGGUUUCUCCUGGCC | HC |
| 476 | 477 | NM_002302.2_572-594_s | 572 | CCCUUGCAGAAAGUUUAUCCU | AGGAUAAACUUUCUGCAAGGGCA | HC |
| 478 | 479 | NM_002302.2_123-145_s | 123 | UUCAAACUUGAAUAUUCUUCA | UGAAGAAUAUUCAAGUUUGAAUG | HC |
| 480 | 481 | NM_002302.2_106-128_s | 106 | UAGCUAGGAAGUAUUCAUUCA | UGAAUGAAUACUUCCUAGCUAUU | HC |
| 482 | 483 | NM_002302.2_571-593_s | 571 | GCCCUUGCAGAAAGUUUAUCC | GGAUAAACUUUCUGCAAGGGCAA | HC |
| 484 | 485 | NM_002302.2_130-152_s | 130 | UUGAAUAUUCUUCAAAGAGAG | CUCUCUUUGAAGAAUAUUCAAGU | HC |
| 486 | 487 | NM_002302.2_664-686_s | 664 | CCAAUGGUCAGAUCUUCAAAA | UUUUGAAGAUCUGACCAUUGGCC | HC |
| 488 | 489 | NM_002302.2_666-688_s | 666 | AAUGGUCAGAUCUUCAAAAUA | UAUUUUGAAGAUCUGACCAUUGG | HC |
| 490 | 491 | NM_002302.2_421-443_s | 421 | UGUGGGCCAGGAGAAACCUUA | UAAGGUUUCUCCUGGCCCACAAU | HC |
| 492 | 493 | NM_002302.2_368-390_s | 368 | GACAUCUUGUGCUCUGCUGGA | UCCAGCAGAGCACAAGAUGUCCA | HC |

[1]H: human; C: cynomolgus monkey; M: mouse; R: rat

Example 2. In Vitro Screening of LECT2 siRNA

Experimental Methods

Cell Culture and Transfections:

Primary Cynomolgus monkey hepatocytes (PCH) (Celsis # M003055, lot CBT) were transfected by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. 80 µl of InVitroGRO CP Rat media (InVitro Technologies) containing ~2×10$^4$ PCH cells were then added to the siRNA mixture. Cells were incubated for 24 hours prior to RNA purification. Single dose experiments were performed at 10 nM and 0.1 nM final duplex concentration and dose response experiments were done over a range of doses from 10 nM to 36 fM final duplex concentration over 8, 6-fold dilutions.

RNA Isolation:

Total RNA was isolated using DYNABEADS mRNA Isolation Kit (Invitrogen, part #: 610-12). Cells were harvested and lysed in 150 µl of Lysis/Binding Buffer then mixed for 5 minute at 850 rpm using an Eppendorf Thermomixer (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis:

cDNA was synthesized using ABI High capacity cDNA reverse transcription kit (Applied Biosystems, Foster City, Calif., Cat #4368813). A master mix of 2 µl 10× Buffer, 0.8 µl 25×dNTPs, 2 µl Random primers, 1 µl Reverse Transcriptase, 1 µl RNase inhibitor and 3.2 µl of H$_2$O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µl of cDNA were added to a master mix containing 0.5 µl of custom designed Cynomolgus monkey GAPDH TaqMan Probe (F-GCATCCTGGGCTACACTGA (SEQ ID NO: 494), R-TGGGTGTCGCTGTTGAAGTC (SEQ ID NO: 495), Probe-CCAGGTGGTCTCCTCC (SEQ ID NO: 496)), 0.5 µl human Lect2 (Hs01040204_m1—which is cross reactive with Cynomolgus monkey Lect2) and 5 µl Lightcycler 480 probe master mix (Roche Cat #04887301001) per well in a 384 well plates (Roche cat #04887301001). Real time PCR was done in a LightCycler480 Real Time PCR system (Roche) using the ΔΔCt(RQ) assay. Each duplex was tested in two independent transfections and each transfection was assayed in duplicate, unless otherwise noted in the summary tables.

To calculate relative fold change, real time data were analyzed using the ΔΔCt method and normalized to assays performed with cells transfected with 10 nM AD-1955, or mock transfected cells. IC50s were calculated using a 4 parameter fit model using XLFit and normalized to cells transfected with AD-1955 or naïve cells.

The modified and unmodified LECT2 siRNA sequences are shown in Tables 5 and 6, respectively. Nucleic acid sequences provided herein are represented using standard nomenclature (see the abbreviations of Table 1). In some instances, mismatches between duplex and mRNA target were allowed at the first antisense (last sense) position when the antisense strand:target mRNA complementary basepair was a GC or CG pair (see Tables 5 and 6, oligos with label G21U, G21A, C21A). In these cases, duplexes were designed with UA or AU pairs at the first antisense:last sense pair. Thus the duplexes maintained complementarity but were mismatched with respect to target (U:C, U:G, A:C, or A:G).

TABLE 5

Modified LECT2 siRNA Sequences

| Duplex Name | Sense Oligo Name | Sense Sequence | SEQ ID NO | Antisense Oligo Name |
|---|---|---|---|---|
| AD-61249 | A-122943 | UfsasGfcUfaGfgAfAfGfuAfuUfcAfuUfcAfL96 | 497 | A-122944 |
| AD-61260 | A-122931 | AfsgsCfuAfgGfaAfGfUfaUfuCfaUfuCfaAfL96 | 499 | A-122932 |
| AD-61254 | A-122929 | AfsusUfcAfuUfcAfAfAfcUfuGfaAfuAfuUfL96 | 501 | A-122930 |
| AD-61243 | A-122941 | UfsusCfaAfaCfuUfGfAfaUfaUfuCfuUfcAfL96 | 503 | A-122942 |
| AD-61261 | A-122947 | UfsusGfaAfuAfuUfCfUfuCfaAfaGfaGfaGfL96 | 505 | A-122948 |
| AD-61242 | A-122925 | UfsusGfaAfuAfuUfCfUfuCfaAfaGfaGfaAfL96 | 507 | A-122926 |
| AD-61248 | A-122927 | GfscsUfaAfuAfuAfUfGfuGfcUfgGfcAfaGfL96 | 509 | A-122928 |
| AD-61277 | A-122921 | GfscsUfaAfuAfuAfUfGfuGfcUfgGfcAfaAfL96 | 511 | A-122922 |
| AD-61253 | A-122913 | CfsasUfgGfcUfgUfGfGfaCfaGfuAfcUfcUfL96 | 513 | A-122914 |
| AD-61259 | A-122915 | UfsgsGfcUfgUfgGfAfCfaGfuAfcUfcUfgCfL96 | 515 | A-122916 |
| AD-61271 | A-122919 | UfsgsGfcUfgUfgGfAfCfaGfuAfcUfcUfgAfL96 | 517 | A-122920 |
| AD-61239 | A-122877 | GfsgsCfuGfuGfgAfCfAfgUfaCfuCfuGfcUfL96 | 519 | A-122878 |
| AD-61257 | A-122883 | GfscsUfgUfgGfaCfAfGfuAfcUfcUfgCfuCfL96 | 521 | A-122884 |
| AD-61246 | A-122895 | GfscsUfgUfgGfaCfAfGfuAfcUfcUfgCfuAfL96 | 523 | A-122896 |
| AD-61245 | A-122879 | CfsusGfuGfgAfcAfGfUfaCfuCfuGfcUfcAfL96 | 525 | A-122880 |
| AD-61268 | A-122871 | UfsgsUfgGfaCfaGfUfAfcUfcUfgCfuCfaAfL96 | 527 | A-122872 |
| AD-61251 | A-122881 | GfsusGfgAfcAfgUfAfCfuCfuGfcUfcAfaAfL96 | 529 | A-122882 |
| AD-61281 | A-122891 | UfsgsGfaCfaGfuAfCfUfcUfgCfuCfaAfaGfL96 | 531 | A-122892 |
| AD-61258 | A-122899 | UfsgsGfaCfaGfuAfCfUfcUfgCfuCfaAfaUfL96 | 533 | A-122900 |
| AD-61275 | A-122889 | GfsgsAfcAfgUfaCfUfCfuGfcUfcAfaAfgAfL96 | 535 | A-122890 |
| AD-61269 | A-122887 | GfsasCfaGfuAfcUfCfUfgCfuCfaAfaGfaAfL96 | 537 | A-122888 |
| AD-61279 | A-122955 | UfsgsUfgGfcCfcAfGfGfaGfaAfaCfcUfuAfL96 | 539 | A-122956 |
| AD-61278 | A-122937 | CfscsAfgGfaGfaAfAfCfcUfuAfuCfaAfaAfL96 | 541 | A-122938 |
| AD-61247 | A-122911 | UfsgsUfuCfuAfcAfUfUfaAfgCfcAfaUfuAfL96 | 543 | A-122912 |
| AD-61241 | A-122909 | GfsusUfcUfaCfaUfUfAfaGfcCfaAfuUfaAfL96 | 545 | A-122910 |
| AD-61282 | A-122907 | UfsusCfuAfcAfuUfAfAfgCfcAfaUfuAfaGfL96 | 547 | A-122908 |
| AD-61265 | A-122917 | UfsusCfuAfcAfuUfAfAfgCfcAfaUfuAfaAfL96 | 549 | A-122918 |
| AD-61276 | A-122905 | UfscsUfaCfaUfuAfAfGfcCfaAfuUfaAfgUfL96 | 551 | A-122906 |
| AD-61250 | A-122865 | CfsusAfcAfuUfaAfGfCfcAfaUfuAfaGfuAfL96 | 553 | A-122866 |
| AD-61256 | A-122867 | UfsasCfaUfuAfaGfCfCfaAfuUfaAfgUfaUfL96 | 555 | A-122868 |
| AD-61262 | A-122869 | AfscsAfuUfaAfgCfCfCfaAfuUfaAfgUfaUfL96 | 557 | A-122870 |

TABLE 5-continued

Modified LECT2 siRNA Sequences

| | | | | |
|---|---|---|---|---|
| AD-61244 | A-122863 | CfsasUfuAfaGfcCfAfAfuUfaAfgUfaUfaAfL96 | 559 | A-122864 |
| AD-61238 | A-122861 | AfsusUfaAfgCfcAfAfUfuAfaGfuAfuAfaAfL96 | 561 | A-122862 |
| AD-61280 | A-122875 | UfsusAfaGfcCfaAfUfUfaAfgUfaUfaAfaGfL96 | 563 | A-122876 |
| AD-61240 | A-122893 | UfsusAfaGfcCfaAfUfUfaAfgUfaUfaAfaUfL96 | 565 | A-122894 |
| AD-61263 | A-122885 | UfsasAfgCfcAfaUfUfAfaGfuAfuAfaAfgGfL96 | 567 | A-122886 |
| AD-61252 | A-122897 | UfsasAfgCfcAfaUfUfAfaGfuAfuAfaAfgAfL96 | 569 | A-122898 |
| AD-61274 | A-122873 | AfsasGfcCfaAfuUfAfAfgUfaUfaAfaGfgUfL96 | 571 | A-122874 |
| AD-61270 | A-122903 | AfsgsCfcAfaUfuAfAfGfuAfuAfaAfgGfuCfL96 | 573 | A-122904 |
| AD-61264 | A-122901 | AfsgsCfcAfaUfuAfAfGfuAfuAfaAfgGfuAfL96 | 575 | A-122902 |
| AD-61255 | A-122945 | GfscsCfcUfuGfcAfGfaAfaGfuUfaUfcCfL96 | 577 | A-122946 |
| AD-61283 | A-122923 | GfscsCfcUfuGfcAfGfaAfaGfuUfaUfcAfL96 | 579 | A-122924 |
| AD-61284 | A-122939 | CfscsCfuUfgCfaGfAfaGfuUfaUfcCfUfL96 | 581 | A-122940 |
| AD-61267 | A-122950 | CfscsAfaUfgGfuCfAfGfaUfcUfuCfaAfaAfL96 | 583 | A-122952 |
| AD-61266 | A-122933 | CfsasAfuGfgUfcAfGfAfuCfuUfcAfaAfaUfL96 | 585 | A-122934 |
| AD-61273 | A-122953 | AfsasUfgGfuCfaGfAfUfcUfuCfaAfaAfuAfL96 | 587 | A-122954 |
| AD-61272 | A-122935 | UfsgsGfuCfaGfaUfCfUfuCfaAfaAfuAfaAfL96 | 589 | A-122936 |

| Duplex Name | Antisense Sequence | SEQ ID NO | Antisense position in NM_002302 |
|---|---|---|---|
| AD-61249 | usGfsaAfuGfaAfuAfcuuCfcUfaGfcUfasusu | 498 | 106-128 |
| AD-61260 | usUfsgAfaUfgAfaUfacuUfcCfuAfgCfusasu | 500 | 107-129 |
| AD-61254 | asAfsuAfuUfcAfaGfuuuGfaAfuGfaAfusasc | 502 | 118-140 |
| AD-61243 | usGfsaAfgAfaUfaUfucaAfgUfuUfgAfasusg | 504 | 123-145 |
| AD-61261 | csUfscUfcUfuUfgAfagaAfuAfuUfcAfasgsu | 506 | 130-152 |
| AD-61242 | usUfscUfcUfuUfgAfagaAfuAfuUfcAfasgsu | 508 | 130-152_G21A |
| AD-61248 | csUfsuGfcCfaGfcAfcauAfuAfuUfaGfcscsc | 510 | 263-285 |
| AD-61277 | usUfsuGfcCfaGfcAfcauAfuAfuUfaGfcscsc | 512 | 263-285_G21A |
| AD-61253 | asGfsaGfuAfcUfgUfccaCfaGfcCfaUfgsgsc | 514 | 314-336 |
| AD-61259 | gsCfsaGfaGfuAfcUfgucCfaCfaGfcCfasusg | 516 | 316-338 |
| AD-61271 | usCfsaGfaGfuAfcUfgucCfaCfaGfcCfasusg | 518 | 316-338_C21A |
| AD-61239 | asGfscAfgAfgUfaCfuguCfcAfcAfgCfcsasu | 520 | 317-339 |
| AD-61257 | gsAfsgCfaGfaGfuAfcugUfcCfaCfaGfcscsa | 522 | 318-340 |
| AD-61246 | usAfsgCfaGfaGfuAfcugUfcCfaCfaGfcscsa | 524 | 318-340_C21A |
| AD-61245 | usGfsaGfcAfgAfgUfacuGfuCfcAfcAfgscsc | 526 | 319-341 |
| AD-61268 | usUfsgAfgCfaGfaGfuacUfgUfcCfaCfasgsc | 528 | 320-342 |
| AD-61251 | usUfsuGfaGfcAfgAfguaCfuGfuCfcAfcsasg | 530 | 321-343 |
| AD-61281 | csUfsuUfgAfgCfaGfaguAfcUfgUfcCfascsa | 532 | 322-344 |
| AD-61258 | asUfsuUfgAfgCfaGfaguAfcUfgUfcCfascsa | 534 | 322-344_G21U |
| AD-61275 | usCfsuUfuGfaGfcAfgagUfaCfuGfuCfcscsa | 536 | 323-345 |
| AD-61269 | usUfscUfuUfgAfgCfagaGfuAfcUfgUfcscsa | 538 | 324-346 |

TABLE 5-continued

Modified LECT2 siRNA Sequences

| | | | |
|---|---|---|---|
| AD-61279 | usAfsaGfgUfuUfcUfccuGfgCfcCfaCfasasu | 540 | 421-443 |
| AD-61278 | usUfsuUfgAfuAfaGfguuUfcUfcCfuGfgscsc | 542 | 427-449 |
| AD-61247 | usAfsaUfuGfgCfuUfaauGfuAfgAfaCfasusu | 544 | 504-526 |
| AD-61241 | usUfsaAfuUfgGfcUfuaaUfgUfaGfaAfcsasu | 546 | 505-527 |
| AD-61282 | csUfsuAfaUfuGfgCfuuaAfuGfuAfgAfascsa | 548 | 506-528 |
| AD-61265 | usUfsuAfuUfgGfcUfuaaAfuGfuAfgAfascsa | 550 | 506-528_G21A |
| AD-61276 | asCfsuUfaAfuUfgGfcuuAfaUfgUfaGfasasc | 552 | 507-529 |
| AD-61250 | usAfscUfuAfaUfuGfgcuUfaAfuGfuAfgsasa | 554 | 508-530 |
| AD-61256 | asUfsaCfuUfaAfuUfggCfuUfaAfuGfUfasgsa | 556 | 509-531 |
| AD-61262 | usAfsuAfcUfuAfaUfuggCfuUfaAfuGfusasg | 558 | 510-532 |
| AD-61244 | usUfsaUfaCfuUfaAfuugGfcUfuAfaUfgsusa | 560 | 511-533 |
| AD-61238 | usUfsuAfuAfcUfuAfauuGfgCfuUfaAfusgsu | 562 | 512-534 |
| AD-61280 | csUfsuUfaUfaCfuUfaauUfgGfcUfuAfasusg | 564 | 513-535 |
| AD-61240 | asUfsuUfaUfaCfuUfaauUfgGfcUfuAfasusg | 566 | 513-535_G21U |
| AD-61263 | csCfsuUfuAfuAfcUfuaaUfuGfgCfuUfasasu | 568 | 514-536 |
| AD-61252 | usCfsuUfuAfuAfcUfuaaAfuGfgCfuUfasasu | 570 | 514-536_G21A |
| AD-61274 | asUfscUfuUfaUfaCfuuaAfuUfgGfcUfusasa | 572 | 515-537 |
| AD-61270 | gsAfscCfuUfuAfuAfcuuAfaUfuGfgCfususa | 574 | 516-538 |
| AD-61264 | usAfscCfuUfuAfuAfcuuAfaUfuGfgCfususa | 576 | 516-538_C21A |
| AD-61255 | gsGfsaUfaAfaCfuUfucuGfcAfaGfgGfcsasa | 578 | 571-593 |
| AD-61283 | usGfsaUfaAfaCfuUfucuGfcAfaGfgGfcsasa | 580 | 571-593_C21A |
| AD-61284 | asGfsgAfuAfaAfcUfuucUfgCfaAfgGfgscsa | 582 | 572-594 |
| AD-61267 | usUfsuUfgAfaGfaUfcugAfcCfaUfuGfgscsc | 584 | 664-686 |
| AD-61266 | asUfsuUfuGfaAfgAfucuGfaCfcAfuUfgsgsc | 586 | 665-687 |
| AD-61273 | usAfsuUfuUfgAfaGfaucUfgAfcCfaUfusgsg | 588 | 666-688 |
| AD-61272 | usUfsuAfuUfuUfgAfagaUfcUfgAfcCfasusu | 590 | 668-690 |

TABLE 6

Unmodified LECT2 siRNA Sequences

| Duplex Name | Sense Oligo Name | Sense Sequence | SEQ ID NO | Sense Position in NM_002302 |
|---|---|---|---|---|
| AD-61249_UM | A-122943 | UAGCUAGGAAGUAUUCAUUCA | 591 | 108-128 |
| AD-61260_UM | A-122931 | AGCUAGGAAGUAUUCAUUCAA | 593 | 109-129 |
| AD-61254_UM | A-122929 | AUUCAUUCAAACUUGAAUAUU | 595 | 120-140 |
| AD-61243_UM | A-122941 | UUCAAACUUGAAUAUUCUUCA | 597 | 125-145 |
| AD-61261_UM | A-122947 | UUGAAUAUUCUUCAAAGAGAG | 599 | 132-152 |
| AD-61242_UM | A-122925 | UUGAAUAUUCUUCAAAGAGAA | 601 | 132-152_G21A |
| AD-61248_UM | A-122927 | GCUAAUAUAUGUGCUGGCAAG | 603 | 265-285 |

TABLE 6-continued

Unmodified LECT2 siRNA Sequences

| | | | | |
|---|---|---|---|---|
| AD-61277 UM | A-122921 | GCUAAUAUAUGUGCUGGCAAA | 605 | 265-285_G21A |
| AD-61253 UM | A-122913 | CAUGGCUGUGGACAGUACUCU | 607 | 316-336 |
| AD-61259 UM | A-122915 | UGGCUGUGGACAGUACUCUGC | 609 | 318-338 |
| AD-61271 UM | A-122919 | UGGCUGUGGACAGUACUCUGA | 611 | 318-338_C21A |
| AD-61239 UM | A-122877 | GGCUGUGGACAGUACUCUGCU | 613 | 319-339 |
| AD-61257 UM | A-122883 | GCUGUGGACAGUACUCUGCUC | 615 | 320-340 |
| AD-61246 UM | A-122895 | GCUGUGGACAGUACUCUGCUA | 617 | 320-340_C21A |
| AD-61245 UM | A-122879 | CUGUGGACAGUACUCUGCUCA | 619 | 321-341 |
| AD-61268 UM | A-122871 | UGUGGACAGUACUCUGCUCAA | 621 | 322-342 |
| AD-61251 UM | A-122881 | GUGGACAGUACUCUGCUCAAA | 623 | 323-343 |
| AD-61281 UM | A-122891 | UGGACAGUACUCUGCUCAAAG | 625 | 324-344 |
| AD-61258 UM | A-122899 | UGGACAGUACUCUGCUCAAAU | 627 | 324-344_G21U |
| AD-61275 UM | A-122889 | GGACAGUACUCUGCUCAAAGA | 629 | 325-345 |
| AD-61269 UM | A-122887 | GACAGUACUCUGCUCAAAGAA | 631 | 326-346 |
| AD-61279 UM | A-122955 | UGUGGGCCAGGAGAAACCUUA | 633 | 423-443 |
| AD-61278 UM | A-122937 | CCAGGAGAAACCUUAUCAAAA | 635 | 429-449 |
| AD-61247 UM | A-122911 | UGUUCUACAUUAAGCCAAUUA | 637 | 506-526 |
| AD-61241 UM | A-122909 | GUUCUACAUUAAGCCAAUUAA | 639 | 507-527 |
| AD-61282 UM | A-122907 | UUCUACAUUAAGCCAAUUAAG | 641 | 508-528 |
| AD-61265 UM | A-122917 | UUCUACAUUAAGCCAAUUAAA | 643 | 508-528_G21A |
| AD-61276 UM | A-122905 | UCUACAUUAAGCCAAUUAAGU | 645 | 509-529 |
| AD-61250 UM | A-122865 | CUACAUUAAGCCAAUUAAGUA | 647 | 510-530 |
| AD-61256 UM | A-122867 | UACAUUAAGCCAAUUAAGUAU | 649 | 511-531 |
| AD-61262 UM | A-122869 | ACAUUAAGCCAAUUAAGUAUA | 651 | 512-532 |
| AD-61244 UM | A-122863 | CAUUAAGCCAAUUAAGUAUAA | 653 | 513-533 |
| AD-61238 UM | A-122861 | AUUAAGCCAAUUAAGUAUAAA | 655 | 514-534 |
| AD-61280 UM | A-122875 | UUAAGCCAAUUAAGUAUAAAG | 657 | 515-535 |
| AD-61240 UM | A-122893 | UUAAGCCAAUUAAGUAUAAAU | 659 | 515-535_G21U |
| AD-61263 UM | A-122885 | UAAGCCAAUUAAGUAUAAAGG | 661 | 516-536 |
| AD-61252 UM | A-122897 | UAAGCCAAUUAAGUAUAAAGA | 663 | 516-536_G21A |
| AD-61274 UM | A-122873 | AAGCCAAUUAAGUAUAAAGGU | 665 | 517-537 |
| AD-61270 UM | A-122903 | AGCCAAUUAAGUAUAAAGGUC | 667 | 518-538 |
| AD-61264 UM | A-122901 | AGCCAAUUAAGUAUAAAGGUA | 669 | 518-538_C21A |
| AD-61255 UM | A-122945 | GCCCUUGCAGAAAGUUUAUCC | 671 | 573-593 |
| AD-61283 UM | A-122923 | GCCCUUGCAGAAAGUUUAUCA | 673 | 573-593_C21A |
| AD-61284 UM | A-122939 | CCCUUGCAGAAAGUUUAUCCU | 675 | 574-594 |
| AD-61267 UM | A-122950 | CCAAUGGUCAGAUCUUCAAAA | 677 | 666-686 |
| AD-61266 UM | A-122933 | CAAUGGUCAGAUCUUCAAAAU | 679 | 667-687 |

TABLE 6-continued

Unmodified LECT2 siRNA Sequences

| Duplex Name | Antisense Oligo Name | Antisense Sequence | SEQ ID NO | Antisense position in NM_002302 |
|---|---|---|---|---|
| AD-61273 UM | A-122953 | AAUGGUCAGAUCUUCAAAAUA | 681 | 668-688 |
| AD-61272 UM | A-122935 | UGGUCAGAUCUUCAAAAUAAA | 683 | 670-690 |
| AD-61249 UM | A-122944 | UGAAUGAAUACUUCCUAGCUAUU | 592 | 106-128 |
| AD-61260 UM | A-122932 | UUGAAUGAAUACUUCCUAGCUAU | 594 | 107-129 |
| AD-61254 UM | A-122930 | AAUAUUCAAGUUUGAAUGAAUAC | 596 | 118-140 |
| AD-61243 UM | A-122942 | UGAAGAAUAUUCAAGUUUGAAUG | 598 | 123-145 |
| AD-61261 UM | A-122948 | CUCUCUUUGAAGAAUAUUCAAGU | 600 | 130-152 |
| AD-61242 UM | A-122926 | UUCUCUUUGAAGAAUAUUCAAGU | 602 | 130-152_G21A |
| AD-61248 UM | A-122928 | CUUGCCAGCACAUAUAUUAGCCC | 604 | 263-285 |
| AD-61277 UM | A-122922 | UUUGCCAGCACAUAUAUUAGCCC | 606 | 263-285_G21A |
| AD-61253 UM | A-122914 | AGAGUACUGUCCACAGCCAUGGC | 608 | 314-336 |
| AD-61259 UM | A-122916 | GCAGAGUACUGUCCACAGCCAUG | 610 | 316-338 |
| AD-61271 UM | A-122920 | UCAGAGUACUGUCCACAGCCAUG | 612 | 316-338_C21A |
| AD-61239 UM | A-122878 | AGCAGAGUACUGUCCACAGCCAU | 614 | 317-339 |
| AD-61257 UM | A-122884 | GAGCAGAGUACUGUCCACAGCCA | 616 | 318-340 |
| AD-61246 UM | A-122896 | UAGCAGAGUACUGUCCACAGCCA | 618 | 318-340_C21A |
| AD-61245 UM | A-122880 | UGAGCAGAGUACUGUCCACAGCC | 620 | 319-341 |
| AD-61268 UM | A-122872 | UUGAGCAGAGUACUGUCCACAGC | 622 | 320-342 |
| AD-61251 UM | A-122882 | UUUGAGCAGAGUACUGUCCACAG | 624 | 321-343 |
| AD-61281 UM | A-122892 | CUUUGAGCAGAGUACUGUCCACA | 626 | 322-344 |
| AD-61258 UM | A-122900 | AUUUGAGCAGAGUACUGUCCACA | 628 | 322-344_G21U |
| AD-61275 UM | A-122890 | UCUUUGAGCAGAGUACUGUCCAC | 630 | 323-345 |
| AD-61269 UM | A-122888 | UUCUUUGAGCAGAGUACUGUCCA | 632 | 324-346 |
| AD-61279 UM | A-122956 | UAAGGUUUCUCCUGGCCCACAAU | 634 | 421-443 |
| AD-61278 UM | A-122938 | UUUUGAUAAGGUUUCUCCUGGCC | 636 | 427-449 |
| AD-61247 UM | A-122912 | UAAUUGGCUUAAUGUAGAACAUU | 638 | 504-526 |
| AD-61241 UM | A-122910 | UUAAUUGGCUUAAUGUAGAACAU | 640 | 505-527 |
| AD-61282 UM | A-122908 | CUUAAUUGGCUUAAUGUAGAACA | 642 | 506-528 |
| AD-61265 UM | A-122918 | UUUAAUUGGCUUAAUGUAGAACA | 644 | 506-528_G21A |
| AD-61276 UM | A-122906 | ACUUAAUUGGCUUAAUGUAGAAC | 646 | 507-529 |
| AD-61250 UM | A-122866 | UACUUAAUUGGCUUAAUGUAGAA | 648 | 508-530 |
| AD-61256 UM | A-122868 | AUACUUAAUUGGCUUAAUGUAGA | 650 | 509-531 |
| AD-61262 UM | A-122870 | UAUACUUAAUUGGCUUAAUGUAG | 652 | 510-532 |
| AD-61244 UM | A-122864 | UUAUACUUAAUUGGCUUAAUGUA | 654 | 511-533 |
| AD-61238 UM | A-122862 | UUUAUACUUAAUUGGCUUAAUGU | 656 | 512-534 |
| AD-61280 UM | A-122876 | CUUUAUACUUAAUUGGCUUAAUG | 658 | 513-535 |

TABLE 6-continued

Unmodified LECT2 siRNA Sequences

| | | | | | |
|---|---|---|---|---|---|
| AD-61240 | UM | A-122894 | AUUUAUACUUAAUUGGCUUAAUG | 660 | 513-535_G21U |
| AD-61263 | UM | A-122886 | CCUUUAUACUUAAUUGGCUUAAU | 662 | 514-536 |
| AD-61252 | UM | A-122898 | UCUUUAUACUUAAUUGGCUUAAU | 664 | 514-536_G21A |
| AD-61274 | UM | A-122874 | ACCUUUAUACUUAAUUGGCUUAA | 666 | 515-537 |
| AD-61270 | UM | A-122904 | GACCUUUAUACUUAAUUGGCUUA | 668 | 516-538 |
| AD-61264 | UM | A-122902 | UACCUUUAUACUUAAUUGGCUUA | 670 | 516-538_C21A |
| AD-61255 | UM | A-122946 | GGAUAAACUUUCUGCAAGGGCAA | 672 | 571-593 |
| AD-61283 | UM | A-122924 | UGAUAAACUUUCUGCAAGGGCAA | 674 | 571-593_C21A |
| AD-61284 | UM | A-122940 | AGGAUAAACUUUCUGCAAGGGCA | 676 | 572-594 |
| AD-61267 | UM | A-122952 | UUUUGAAGAUCUGACCAUUGGCC | 678 | 664-686 |
| AD-61266 | UM | A-122934 | AUUUUGAAGAUCUGACCAUUGGC | 680 | 665-687 |
| AD-61273 | UM | A-122954 | UAUUUUGAAGAUCUGACCAUUGG | 682 | 666-688 |
| AD-61272 | UM | A-122936 | UUUAUUUUGAAGAUCUGACCAUU | 684 | 668-690 |

Results

The results of single dose screen in primary monkey hepatocytes are shown in Table 7. The single dose experiments were performed at 10 nM and 0.1 nM final duplex concentration and the data are expressed as percent message remaining relative to AD-1955 non-targeting control.

TABLE 7

LECT2 siRNA Single Dose Screen in Primary Monkey Hepatocytes

| DuplexID | 10 nM_AVG | 0.1 nM_AVG | 10 nM_STDEV | 0.1 nM_STDEV |
|---|---|---|---|---|
| AD-61278 | 1.8 | 22.3 | 0.78 | 6.56 |
| AD-61268 | 4.6 | 43.2 | 2.72 | 9.01 |
| AD-61251 | 4.8 | 41.0 | 1.50 | 9.73 |
| AD-61260 | 5.6 | 48.9 | 0.40 | 4.98 |
| AD-61258 | 5.9 | 50.8 | 0.70 | 0.29 |
| AD-61277 | 6.2 | 33.4 | 0.14 | 8.56 |
| AD-61241 | 6.3 | 32.3 | 4.28 | 8.26 |
| AD-61242 | 6.8 | 64.2 | 0.58 | 14.00 |
| AD-61273 | 7.0 | 18.0 | 0.46 | 0.16 |
| AD-61243 | 7.0 | 34.9 | 3.27 | 6.84 |
| AD-61267 | 7.2 | 20.1 | 1.52 | 0.31 |
| AD-61266 | 7.3 | 20.0 | 1.12 | 0.57 |
| AD-61256 | 7.3 | 18.6 | 1.44 | 2.53 |
| AD-61284 | 7.6 | 31.0 | 1.42 | 0.58 |
| AD-61246 | 7.6 | 74.2 | 0.62 | 8.28 |
| AD-61272 | 7.8 | 15.3 | 0.17 | 0.99 |
| AD-61244 | 7.9 | 20.5 | 0.14 | 3.97 |
| AD-61275 | 8.3 | 63.8 | 3.06 | 5.57 |
| AD-61265 | 9.8 | 34.4 | 1.42 | 0.65 |
| AD-61281 | 10.2 | 48.2 | 0.28 | 12.35 |
| AD-61254 | 10.4 | 63.6 | 1.65 | 15.68 |
| AD-61257 | 10.5 | 66.5 | 1.36 | 16.73 |
| AD-61238 | 11.0 | 42.2 | 1.69 | 2.24 |
| AD-61240 | 11.6 | 30.7 | 0.31 | 2.28 |
| AD-61250 | 11.8 | 57.0 | 1.24 | 15.15 |
| AD-61262 | 13.7 | 57.7 | 2.37 | 10.92 |
| AD-61249 | 13.8 | 74.7 | 0.57 | 1.53 |
| AD-61283 | 14.3 | 59.2 | ND | 13.47 |
| AD-61282 | 14.7 | 44.6 | 0.11 | 1.13 |
| AD-61261 | 15.6 | 58.0 | 0.65 | 25.10 |
| AD-61264 | 16.2 | 66.7 | 0.75 | 2.89 |
| AD-61239 | 16.6 | 78.5 | 6.08 | 4.68 |
| AD-61274 | 17.9 | 66.9 | 3.54 | 13.94 |
| AD-61253 | 18.8 | 90.1 | 0.23 | 4.49 |
| AD-61280 | 18.8 | 56.8 | 4.16 | 9.66 |

TABLE 7-continued

LECT2 siRNA Single Dose Screen in Primary Monkey Hepatocytes

| DuplexID | 10 nM_AVG | 0.1 nM_AVG | 10 nM_STDEV | 0.1 nM_STDEV |
|---|---|---|---|---|
| AD-61276 | 21.0 | 71.0 | 0.87 | 3.88 |
| AD-61269 | 21.1 | 85.8 | 2.52 | 10.42 |
| AD-61279 | 21.5 | 67.6 | 0.58 | 1.60 |
| AD-61255 | 22.1 | 87.0 | 4.14 | 1.78 |
| AD-61248 | 25.7 | 85.8 | 2.95 | 9.58 |
| AD-61270 | 27.4 | 77.8 | 3.94 | 12.22 |
| AD-61252 | 28.1 | 82.3 | 0.89 | 0.07 |
| AD-61245 | 41.9 | 90.1 | 6.65 | 3.46 |
| AD-61271 | 46.5 | 82.5 | 4.44 | 26.55 |
| AD-61263 | 53.2 | 82.4 | 4.04 | 11.61 |
| AD-61247 | 56.7 | 93.6 | 1.25 | 4.20 |
| AD-61259 | 78.1 | 90.2 | 0.96 | 7.14 |
| AD-1955 | 100.6 | | 11.1 | |

A subset of LECT2 siRNA duplexes tested in the single dose screen were further tested in a dose response screen in primary monkey hepatocytes. The results are shown in Table 8. The dose response experiments were performed over a range of doses from 10 nM to 36 fM final duplex concentration. The data are expressed as 1050 values.

TABLE 8

LECT2 SiRNA Dose Response Screen in Primary Monkey Hepatocytes

| Duplex ID | IC50 (nM) |
|---|---|
| AD-61272 | 0.0024 |
| AD-61273 | 0.0006 |
| AD-61266 | 0.003 |
| AD-61267 | 0.0026 |
| AD-61278 | 0.0124 |
| AD-61284 | 0.0522 |
| AD-61240 | 0.0084 |
| AD-61251 | 0.0621 |
| AD-61268 | 0.117 |
| AD-61256 | 0.0163 |
| AD-61244 | 0.0165 |

Example 3. LECT2 siRNA Gene Walk

Experimental Methods

Bioinformatics:

A set of 93 overlapping siRNAs targeting the human LECT2 gene (NCBI refseqID NM_002302.2; NCBI Gene ID 3950 "leukocyte cell-derived chemotaxin 2") were designed using custom R and Python scripts. The LECT2 REFSEQ mRNA has a length of 1077 bases.

In Vitro Screening:

Cell Culture and Transfections:

Primary cynomolgus monkey hepatocytes (PCHs, Celsis # M003055, lot CBT) were transfected by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. 80 µl of phenol red-free Williams Medium E (Life Technologies #A1217601) containing ~2×10$^4$ PCH cells were then added to the siRNA mixture. Cells were incubated for 24 hours prior to RNA purification. Single dose experiments were performed at 10 nM.

Total RNA was isolated using DYNABEADS mRNA Isolation Kit (Invitrogen, part #: 610-12). Cells were harvested and lysed in 150 µl of Lysis/Binding Buffer then mixed for 5 minute at 850 rpm using an Eppendorf Thermomixer (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis:

cDNA was synthesized using ABI High capacity cDNA reverse transcription kit (Applied Biosystems, Foster City, Calif., Cat #4368813). A master mix of 2 µl 10× Buffer, 0.8 µl 25×dNTPs, 2 µl Random primers, 1 µl Reverse Transcriptase, 1 µl RNase inhibitor and 3.2 µl of H$_2$O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µl of cDNA were added to a master mix containing 0.5 µl of custom designed Cynomolgus monkey GAPDH TaqMan Probe (F-GCATCCTGGGCTACACTGA (SEQ ID NO: 494), R-TGGGTGTCGCTGTTGAAGTC (SEQ ID NO: 495), Probe-CCAGGTGGTCTCCTCC (SEQ ID NO: 496)), 0.5 µl human Lect2 (Hs01040204_m1—which is cross reactive with Cynomolgus monkey Lect2) and 5 µl Lightcycler 480 probe master mix (Roche Cat #04887301001) per well in a 384 well plates (Roche cat #04887301001). Real time PCR was done in a LightCycler480 Real Time PCR system (Roche) using the ΔΔCt(RQ) assay. Each duplex was tested in two independent transfections and each transfection was assayed in duplicate, unless otherwise noted in the summary tables. To calculate relative fold change, real time data were analyzed using the ΔΔCt method and normalized to assays performed with cells transfected with 10 nM AD-1955, or mock transfected cells.

The modified and unmodified LECT2 siRNA sequences are shown in Tables 9 and 10, respectively. Nucleic acid sequences provided herein are represented using standard nomenclature (see the abbreviations of Table 1).

TABLE 9

Modified LECT2 siRNA Sequences

| Target | Duplex Name | Sense Oligo Name | Sense Oligo Sequence | SEQ ID NO | Antisense Oligo Name | Antisense Oligo Sequence | SEQ ID NO |
|---|---|---|---|---|---|---|---|
| LECT2 | AD-65819.1 | A-131907.1 | GAAUAUUAGAACUUGACUUdTdT | 690 | A-131908.1 | AAGUCAAGUUCUAAUAUUCdTdT | 691 |
| LECT2 | AD-65825.1 | A-131909.1 | AACUUGACUUGCUCCAUCCdTdT | 692 | A-131910.1 | GGAUGGAGCAAGUCAAGUUdTdT | 693 |
| LECT2 | AD-65831.1 | A-131911.1 | CCAUCCUCUUAAACUUUUUdTdT | 694 | A-131912.1 | AAAAAGUUUAAGAGGAUGGdTdT | 695 |
| LECT2 | AD-65837.1 | A-131913.1 | UAAACUUUUUGUGUCUCACdTdT | 696 | A-131914.1 | GUGAGACACAAAAAGUUUAdTdT | 697 |
| LECT2 | AD-65843.1 | A-131915.1 | GUCUCACACUAAAGAAAUGdTdT | 698 | A-131916.1 | CAUUUCUUUAGUGUGAGACdTdT | 699 |
| LECT2 | AD-65849.1 | A-131917.1 | AAAGAAAUGAGAGAUGCAGdTdT | 700 | A-131918.1 | CUGCAUCUCUCAUUUCUUUdTdT | 701 |
| LECT2 | AD-65855.1 | A-131919.1 | AUGCAGAAUUCUAAGGCUAdTdT | 702 | A-131920.1 | UAGCCUUAGAAUUCUGCAUdTdT | 703 |
| LECT2 | AD-65861.1 | A-131921.1 | UCUAAGGCUAAAUAGCUAGdTdT | 704 | A-131922.1 | CUAGCUAUUUAGCCUUAGAdTdT | 705 |
| LECT2 | AD-65820.1 | A-131923.1 | AUAGCUAGGAAGUAUUCAUdTdT | 706 | A-131924.1 | AUGAAUACUUCCUAGCUAUdTdT | 707 |
| LECT2 | AD-65826.1 | A-131925.1 | AUUCAUUCAAACUUGAAUAdTdT | 708 | A-131926.1 | UAUUCAAGUUUGAAUGAAUdTdT | 709 |
| LECT2 | AD-65832.1 | A-131927.1 | CUUGAAUAUUCUUCAAAGAdTdT | 710 | A-131928.1 | UCUUUGAAGAAUAUUCAAGdTdT | 711 |
| LECT2 | AD-65838.1 | A-131929.1 | CUUCAAAGAGAGUGUGGGGdTdT | 712 | A-131930.1 | CCCCACACUCUCUUUGAAGdTdT | 713 |
| LECT2 | AD-65844.1 | A-131931.1 | GUGUGGGGGCAACUCUAAUdTdT | 714 | A-131932.1 | AUUAGAGUUGCCCCCACACdTdT | 715 |

TABLE 9-continued

Modified LECT2 siRNA Sequences

| Target | Duplex Name | Sense Oligo Name | Sense Oligo Sequence | SEQ ID NO | Antisense Oligo Name | Antisense Oligo Sequence | SEQ ID NO |
|---|---|---|---|---|---|---|---|
| LECT2 | AD-65850.1 | A-131933.1 | AACUCUAAUCAGAGGAAGAdTdT | 716 | A-131934.1 | UCUUCCUCUGAUUAGAGUUdTdT | 717 |
| LECT2 | AD-65856.1 | A-131935.1 | AGGAAGAAACUAAAGGAAGdTdT | 718 | A-131936.1 | CUUCCUUUAGUUUCUUCCUdTdT | 719 |
| LECT2 | AD-65862.1 | A-131937.1 | UAAAGGAAGUAAAACCAGAdTdT | 720 | A-131938.1 | UCUGGUUUUACUUCCUUUAdTdT | 721 |
| LECT2 | AD-65821.1 | A-131939.1 | AAACCAGAUGUUUUCCACCdTdT | 722 | A-131940.1 | GGUGGAAAACAUCUGGUUUdTdT | 723 |
| LECT2 | AD-65827.1 | A-131941.1 | UCCACCAAAGCCCUCCUUUdTdT | 724 | A-131942.1 | AAAGGAGGGCUUUGGUGGAdTdT | 725 |
| LECT2 | AD-65833.1 | A-131943.1 | CCUCCUUUUGGCUGGUCUGdTdT | 726 | A-131944.1 | CAGACCAGCCAAAAGGAGGdTdT | 727 |
| LECT2 | AD-65839.1 | A-131945.1 | GGCUGGUCUGAUUUCUACCdTdT | 728 | A-131946.1 | GGUAGAAAUCAGACCAGCCdTdT | 729 |
| LECT2 | AD-65845.1 | A-131947.1 | UUUCUACCGCACUGGCAGGdTdT | 730 | A-131948.1 | CCUGCCAGUGCGGUAGAAAdTdT | 731 |
| LECT2 | AD-65851.1 | A-131949.1 | GGCAGGGCCAUGGGCUAAUdTdT | 732 | A-131950.1 | AUUAGCCCAUGGCCCUGCCdTdT | 733 |
| LECT2 | AD-65857.1 | A-131951.1 | GGGCUAAUAUAUGUGCUGGdTdT | 734 | A-131952.1 | CCAGCACAUAUAUUAGCCCdTdT | 735 |
| LECT2 | AD-65863.1 | A-131953.1 | AUGUGCUGGCAAGUCUUCCdTdT | 736 | A-131954.1 | GGAAGACUUGCCAGCACAUdTdT | 737 |
| LECT2 | AD-65822.1 | A-131955.1 | AAGUCUUCCAAUGAGAUCCdTdT | 738 | A-131956.1 | GGAUCUCAUUGGAAGACUUdTdT | 739 |
| LECT2 | AD-65828.1 | A-131957.1 | AGAUCCGGACGUGUGACCGdTdT | 740 | A-131958.1 | CGGUCACACGUCCGGAUCUdTdT | 741 |
| LECT2 | AD-65834.1 | A-131959.1 | GUGUGACCGCCAUGGCUGUdTdT | 742 | A-131960.1 | ACAGCCAUGGCGGUCACACdTdT | 743 |
| LECT2 | AD-65840.1 | A-131961.1 | AUGGCUGUGGACAGUACUCdTdT | 744 | A-131962.1 | GAGUACUGUCCACAGCCAUdTdT | 745 |
| LECT2 | AD-65846.1 | A-131963.1 | AGUACUCUGCUCAAAGAAGdTdT | 746 | A-131964.1 | CUUCUUUGAGCAGAGUACUdTdT | 747 |
| LECT2 | AD-65852.1 | A-131965.1 | CAAAGAAGUCAGAGGCCUCdTdT | 748 | A-131966.1 | GAGGCCUCUGACUUCUUUGdTdT | 749 |
| LECT2 | AD-65858.1 | A-131967.1 | CAGAGGCCUCACCAGGGUGdTdT | 750 | A-131968.1 | CACCCUGGUGAGGCCUCUGdTdT | 751 |
| LECT2 | AD-65864.1 | A-131969.1 | CCAGGGUGUGGACAUCUUGdTdT | 752 | A-131970.1 | CAAGAUGUCCACACCCUGGdTdT | 753 |
| LECT2 | AD-65823.1 | A-131971.1 | ACAUCUUGUGCUCUGCUGGdTdT | 754 | A-131972.1 | CCAGCAGAGCACAAGAUGUdTdT | 755 |
| LECT2 | AD-65829.1 | A-131973.1 | CUGCUGGAUCUACUGUGUAdTdT | 756 | A-131974.1 | UACACAGUAGAUCCAGCAGdTdT | 757 |
| LECT2 | AD-65835.1 | A-131975.1 | CUGUGUACGCACCAUUCACdTdT | 758 | A-131976.1 | GUGAAUGGUGCGUACACAGdTdT | 759 |
| LECT2 | AD-65841.1 | A-131977.1 | CCAUUCACUGGAAUGAUUGdTdT | 760 | A-131978.1 | CAAUCAUUCCAGUGAAUGGdTdT | 761 |
| LECT2 | AD-65847.1 | A-131979.1 | AAUGAUUGUGGGCCAGGAGdTdT | 762 | A-131980.1 | CUCCUGGCCCACAAUCAUUdTdT | 763 |
| LECT2 | AD-65853.1 | A-131981.1 | GGGCCAGGAGAAACCUUAUdTdT | 764 | A-131982.1 | AUAAGGUUUCUCCUGGCCCdTdT | 765 |
| LECT2 | AD-65859.1 | A-131983.1 | CCUUAUCAAACAAGAAUGdTdT | 766 | A-131984.1 | CAUUCUUGUUUGAUAAGGdTdT | 767 |
| LECT2 | AD-65865.1 | A-131985.1 | CAAGAAUGCUAUCAAUAAUdTdT | 768 | A-131986.1 | AUUAUUGAUAGCAUUCUUGdTdT | 769 |
| LECT2 | AD-65824.1 | A-131987.1 | AUCAAUAAUGGUGUUCGAAdTdT | 770 | A-131988.1 | UUCGAACACCAUUAUUGAUdTdT | 771 |
| LECT2 | AD-65830.1 | A-131989.1 | GUUCGAAUAUCUGGAAGAGdTdT | 772 | A-131990.1 | CUCUUCCAGAUAUUCGAACdTdT | 773 |
| LECT2 | AD-65836.1 | A-131991.1 | UCUGGAAGAGGUUUUUGUGdTdT | 774 | A-131992.1 | CACAAAAACCUCUUCCAGAdTdT | 775 |
| LECT2 | AD-65842.1 | A-131993.1 | UUUUUGUGUCAAAAUGUUCdTdT | 776 | A-131994.1 | GAACAUUUUGACACAAAAAdTdT | 777 |
| LECT2 | AD-65848.1 | A-131995.1 | AUGUUCUACAUUAAGCCAAdTdT | 778 | A-131996.1 | UUGGCUUAAUGUAGAACAUdTdT | 779 |
| LECT2 | AD-65854.1 | A-131997.1 | UAAGCCAAUUAAGUAUAAAdTdT | 780 | A-131998.1 | UUUAUACUUAAUUGGCUUAdTdT | 781 |
| LECT2 | AD-65860.1 | A-131999.1 | AAGUAUAAAGGUCCUAUUAdTdT | 782 | A-132000.1 | UAAUAGGACCUUUAUACUUdTdT | 783 |
| LECT2 | AD-65866.1 | A-132001.1 | CCUAUUAAGAAGGGAGAAAdTdT | 784 | A-132002.1 | UUUCUCCCUUCUUAAUAGGdTdT | 785 |
| LECT2 | AD-65872.1 | A-132003.1 | AGGGAGAAAACUUGGAACdTdT | 786 | A-132004.1 | GUUCCAAGUUUUCUCCCUdTdT | 787 |
| LECT2 | AD-65878.1 | A-132005.1 | CUUGGAACUCUAUUGCCCUdTdT | 788 | A-132006.1 | AGGGCAAUAGAGUUCCAAGdTdT | 789 |

TABLE 9-continued

Modified LECT2 siRNA Sequences

| Target | Duplex Name | Sense Oligo Name | Sense Oligo Sequence | SEQ ID NO | Antisense Oligo Name | Antisense Oligo Sequence | SEQ ID NO |
|---|---|---|---|---|---|---|---|
| LECT2 | AD-65884.1 | A-132007.1 | UUGCCCUUGCAGAAAGUUUdTdT | 790 | A-132008.1 | AAACUUUCUGCAAGGGCAAdTdT | 791 |
| LECT2 | AD-65890.1 | A-132009.1 | AGAAAGUUUAUCCUGGCAUdTdT | 792 | A-132010.1 | AUGCCAGGAUAAACUUUCUdTdT | 793 |
| LECT2 | AD-65896.1 | A-132011.1 | CCUGGCAUACAAUCGCAUGdTdT | 794 | A-132012.1 | CAUGCGAUUGUAUGCCAGGdTdT | 795 |
| LECT2 | AD-65902.1 | A-132013.1 | AUCGCAUGUGCACAUUGAAdTdT | 796 | A-132014.1 | UUCAAUGUGCACAUGCGAUdTdT | 797 |
| LECT2 | AD-65907.1 | A-132015.1 | CAUUGAAAACUGUGACUCGdTdT | 798 | A-132016.1 | CGAGUCACAGUUUUCAAUGdTdT | 799 |
| LECT2 | AD-65867.1 | A-132017.1 | GUGACUCGAGUGACCCUACdTdT | 800 | A-132018.1 | GUAGGGUCACUCGAGUCACdTdT | 801 |
| LECT2 | AD-65873.1 | A-132019.1 | UGACCCUACUGCAUACCUGdTdT | 802 | A-132020.1 | CAGGUAUGCAGUAGGGUCAdTdT | 803 |
| LECT2 | AD-65879.1 | A-132021.1 | CAUACCUGUAAAUCGAAGGdTdT | 804 | A-132022.1 | CCUUCGAUUUACAGGUAUGdTdT | 805 |
| LECT2 | AD-65891.1 | A-132025.1 | UGGUCAGAUCUUCAAAAUAdTdT | 806 | A-132026.1 | UAUUUUGAAGAUCUGACCAdTdT | 807 |
| LECT2 | AD-65897.1 | A-132027.1 | CUUCAAAAUAAAAAGUCAUdTdT | 808 | A-132028.1 | AUGACUUUUUAUUUUGAAGdTdT | 809 |
| LECT2 | AD-65903.1 | A-132029.1 | AAGUCAUCUUAAAAACCUGdTdT | 810 | A-132030.1 | CAGGUUUUUAAGAUGACUUdTdT | 811 |
| LECT2 | AD-65908.1 | A-132031.1 | AAAACCUGGAUGCAUACCCdTdT | 812 | A-132032.1 | GGGUAUGCAUCCAGGUUUUdTdT | 813 |
| LECT2 | AD-65868.1 | A-132033.1 | GCAUACCCUUCUCUUCAAGdTdT | 814 | A-132034.1 | CUUGAAGAGAAGGGUAUGCdTdT | 815 |
| LECT2 | AD-65874.1 | A-132035.1 | CUUCAAGAAAUUUGUGUUCdTdT | 816 | A-132036.1 | GAACACAAAUUUCUUGAAGdTdT | 817 |
| LECT2 | AD-65880.1 | A-132037.1 | UUGUGUUCACAAAGGAAAAdTdT | 818 | A-132038.1 | UUUUCCUUUGUGAACACAAdTdT | 819 |
| LECT2 | AD-65886.1 | A-132039.1 | AAGGAAAAUGCAUGAAGGdTdT | 820 | A-132040.1 | CCUUCAUGCAUUUUCCUUdTdT | 821 |
| LECT2 | AD-65892.1 | A-132041.1 | UGCAUGAAGGGAUGGAUACdTdT | 822 | A-132042.1 | GUAUCCAUCCCUUCAUGCAdTdT | 823 |
| LECT2 | AD-65898.1 | A-132043.1 | UGGAUACCCCAUUUUCCAUdTdT | 824 | A-132044.1 | AUGGAAAAUGGGGUAUCCAdTdT | 825 |
| LECT2 | AD-65904.1 | A-132045.1 | UUUCCAUGACAUGAUUAUUdTdT | 826 | A-132046.1 | AAUAAUCAUGUCAUGGAAAdTdT | 827 |
| LECT2 | AD-65909.1 | A-132047.1 | CAUGAUUAUUACACAUUGCdTdT | 828 | A-132048.1 | GCAAUGUGUAAUAAUCAUGdTdT | 829 |
| LECT2 | AD-65869.1 | A-132049.1 | CACAUUGCAUGCCUGUAUCdTdT | 830 | A-132050.1 | GAUACAGGCAUGCAAUGUGdTdT | 831 |
| LECT2 | AD-65875.1 | A-132051.1 | CCUGUAUCAAAACAUCUCAdTdT | 832 | A-132052.1 | UGAGAUGUUUUGAUACAGGdTdT | 833 |
| LECT2 | AD-65881.1 | A-132053.1 | CAUCUCACGUACCUCAUAAdTdT | 834 | A-132054.1 | UUAUGAGGUACGUGAGAUGdTdT | 835 |
| LECT2 | AD-65887.1 | A-132055.1 | CCUCAUAAACAUAUACACCdTdT | 836 | A-132056.1 | GGUGUAUAUGUUUAUGAGGdTdT | 837 |
| LECT2 | AD-65893.1 | A-132057.1 | AUACACCUAUGUACCCACAdTdT | 838 | A-132058.1 | UGUGGGUACAUAGGUGUAUdTdT | 839 |
| LECT2 | AD-65899.1 | A-132059.1 | GUACCCACAAAAUUUUUUdTdT | 840 | A-132060.1 | AAAAAAUUUUGUGGGUACdTdT | 841 |
| LECT2 | AD-65905.1 | A-132061.1 | UAAAAAAGGAAAUUUGAGdTdT | 842 | A-132062.1 | CUCAAAUUCCUUUUUUAdTdT | 843 |
| LECT2 | AD-65910.1 | A-132063.1 | AAUUUGAGUUUAAAUAGAAdTdT | 844 | A-132064.1 | UUCUAUUUAAACUCAAAUUdTdT | 845 |
| LECT2 | AD-65870.1 | A-132065.1 | AUAGAAACAUGAUAAAUGCdTdT | 846 | A-132066.1 | GCAUUUAUCAUGUUUCUAUdTdT | 847 |
| LECT2 | AD-65876.1 | A-132067.1 | GAUAAAUGCAAGAAAGAAAdTdT | 848 | A-132068.1 | UUUCUUUCUUGCAUUUAUCdTdT | 849 |
| LECT2 | AD-65882.1 | A-132069.1 | GAAAGAAACAUUUUGAUUdTdT | 850 | A-132070.1 | AAUCAAAAUGUUUCUUUCdTdT | 851 |
| LECT2 | AD-65894.1 | A-132073.1 | ACUCAUUGUCACUCUGAUGdTdT | 852 | A-132074.1 | CAUCAGAGUGACAAUGAGUdTdT | 853 |
| LECT2 | AD-65900.1 | A-132075.1 | CUCUGAUGUUCAUGUGAACdTdT | 854 | A-132076.1 | GUUCACAUGAACAUCAGAGdTdT | 855 |
| LECT2 | AD-65906.1 | A-132077.1 | CAUGUGAACUGGUUGCUUCdTdT | 856 | A-132078.1 | GAAGCAACCAGUUCACAUGdTdT | 857 |
| LECT2 | AD-65911.1 | A-132079.1 | GUUGCUUCGGGCUCUUUGAdTdT | 858 | A-132080.1 | UCAAAGAGCCCGAAGCAACdTdT | 859 |
| LECT2 | AD-65871.1 | A-132081.1 | UCUUUGAUCUGUCACCUAUdTdT | 860 | A-132082.1 | AUAGGUGACAGAUCAAAGAdTdT | 861 |
| LECT2 | AD-65877.1 | A-132083.1 | CACCUAUGGAAUCUGAGUGdTdT | 862 | A-132084.1 | CACUCAGAUUCCAUAGGUGdTdT | 863 |

TABLE 9-continued

Modified LECT2 siRNA Sequences

| Target | Duplex Name | Sense Oligo Name | Sense Oligo Sequence | SEQ ID NO | Antisense Oligo Name | Antisense Oligo Sequence | SEQ ID NO |
|---|---|---|---|---|---|---|---|
| LECT2 | AD-65883.1 | A-132085.1 | AAUCUGAGUGGUUUUAUUUdTdT | 864 | A-132086.1 | AAAUAAACCACUCAGAUUdTdT | 865 |
| LECT2 | AD-65889.1 | A-132087.1 | UUUUUUAGAUUUCUCAGUCdTdT | 866 | A-132088.1 | GACUGAGAAAUCUAAAAAAdTdT | 867 |
| LECT2 | AD-65895.1 | A-132089.1 | CUCAGUCCCAAAGAUCUAAdTdT | 868 | A-132090.1 | UUAGAUCUUUGGGACUGAGdTdT | 869 |
| LECT2 | AD-65901.1 | A-132091.1 | GAUCUAAGAUAAAUAAACAdTdT | 870 | A-132092.1 | UGUUUAUUUAUCUUAGAUCdTdT | 871 |

TABLE 10

Unmodified LECT2 siRNA Sequences

| Target | Duplex Name | Sense Oligo Name | Sense Sequence | SEQ ID NO | Position in NM_002302.2 |
|---|---|---|---|---|---|
| LECT2 | AD-65819.1 | A-131907.1 | GAAUAUUAGAACUUGACUU | 872 | 011-29 |
| LECT2 | AD-65825.1 | A-131909.1 | AACUUGACUUGCUCCAUCC | 874 | 020-38 |
| LECT2 | AD-65831.1 | A-131911.1 | CCAUCCUCUUAAACUUUUU | 876 | 033-51 |
| LECT2 | AD-65837.1 | A-131913.1 | UAAACUUUUUGUGUCUCAC | 878 | 042-60 |
| LECT2 | AD-65843.1 | A-131915.1 | GUCUCACACUAAAGAAAUG | 880 | 054-72 |
| LECT2 | AD-65849.1 | A-131917.1 | AAAGAAAUGAGAGAUGCAG | 882 | 064-82 |
| LECT2 | AD-65855.1 | A-131919.1 | AUGCAGAAUUCUAAGGCUA | 884 | 077-95 |
| LECT2 | AD-65861.1 | A-131921.1 | UCUAAGGCUAAAUAGCUAG | 886 | 086-104 |
| LECT2 | AD-65820.1 | A-131923.1 | AUAGCUAGGAAGUAUUCAU | 888 | 097-115 |
| LECT2 | AD-65826.1 | A-131925.1 | AUUCAUUCAAACUUGAAUA | 890 | 110-128 |
| LECT2 | AD-65832.1 | A-131927.1 | CUUGAAUAUUCUUCAAAGA | 892 | 121-139 |
| LECT2 | AD-65838.1 | A-131929.1 | CUUCAAAGAGAGUGUGGGG | 894 | 131-149 |
| LECT2 | AD-65844.1 | A-131931.1 | GUGUGGGGGCAACUCUAAU | 896 | 142-160 |
| LECT2 | AD-65850.1 | A-131933.1 | AACUCUAAUCAGAGGAAGA | 898 | 152-170 |
| LECT2 | AD-65856.1 | A-131935.1 | AGGAAGAAACUAAAGGAAG | 900 | 164-182 |
| LECT2 | AD-65862.1 | A-131937.1 | UAAAGGAAGUAAAACCAGA | 902 | 174-192 |
| LECT2 | AD-65821.1 | A-131939.1 | AAACCAGAUGUUUUCCACC | 904 | 185-203 |
| LECT2 | AD-65827.1 | A-131941.1 | UCCACCAAAGCCCUCCUUU | 906 | 198-216 |
| LECT2 | AD-65833.1 | A-131943.1 | CCUCCUUUUGGCUGGUCUG | 908 | 209-227 |
| LECT2 | AD-65839.1 | A-131945.1 | GGCUGGUCUGAUUUCUACC | 910 | 218-236 |
| LECT2 | AD-65845.1 | A-131947.1 | UUUCUACCGCACUGGCAGG | 912 | 229-247 |
| LECT2 | AD-65851.1 | A-131949.1 | GGCAGGGCCAUGGGCUAAU | 914 | 242-260 |
| LECT2 | AD-65857.1 | A-131951.1 | GGGCUAAUAUAUGUGCUGG | 916 | 253-271 |
| LECT2 | AD-65863.1 | A-131953.1 | AUGUGCUGGCAAGUCUUCC | 918 | 263-281 |
| LECT2 | AD-65822.1 | A-131955.1 | AAGUCUUCCAAUGAGAUCC | 920 | 273-291 |
| LECT2 | AD-65828.1 | A-131957.1 | AGAUCCGGACGUGUGACCG | 922 | 286-304 |
| LECT2 | AD-65834.1 | A-131959.1 | GUGUGACCGCCAUGGCUGU | 924 | 296-314 |

TABLE 10-continued

Unmodified LECT2 siRNA Sequences

| | | | | | |
|---|---|---|---|---|---|
| LECT2 | AD-65840.1 | A-131961.1 | AUGGCUGUGGACAGUACUC | 926 | 307-325 |
| LECT2 | AD-65846.1 | A-131963.1 | AGUACUCUGCUCAAAGAAG | 928 | 319-337 |
| LECT2 | AD-65852.1 | A-131965.1 | CAAAGAAGUCAGAGGCCUC | 930 | 330-348 |
| LECT2 | AD-65858.1 | A-131967.1 | CAGAGGCCUCACCAGGGUG | 932 | 339-357 |
| LECT2 | AD-65864.1 | A-131969.1 | CCAGGGUGUGGACAUCUUG | 934 | 350-368 |
| LECT2 | AD-65823.1 | A-131971.1 | ACAUCUUGUGCUCUGCUGG | 936 | 361-379 |
| LECT2 | AD-65829.1 | A-131973.1 | CUGCUGGAUCUACUGUGUA | 938 | 373-391 |
| LECT2 | AD-65835.1 | A-131975.1 | CUGUGUACGCACCAUUCAC | 940 | 385-403 |
| LECT2 | AD-65841.1 | A-131977.1 | CCAUUCACUGGAAUGAUUG | 942 | 396-414 |
| LECT2 | AD-65847.1 | A-131979.1 | AAUGAUUGUGGGCCAGGAG | 944 | 407-425 |
| LECT2 | AD-65853.1 | A-131981.1 | GGGCCAGGAGAAACCUUAU | 946 | 416-434 |
| LECT2 | AD-65859.1 | A-131983.1 | CCUUAUCAAACAAGAAUG | 948 | 429-447 |
| LECT2 | AD-65865.1 | A-131985.1 | CAAGAAUGCUAUCAAUAAU | 950 | 440-458 |
| LECT2 | AD-65824.1 | A-131987.1 | AUCAAUAAUGGUGUUCGAA | 952 | 450-468 |
| LECT2 | AD-65830.1 | A-131989.1 | GUUCGAAUAUCUGGAAGAG | 954 | 462-480 |
| LECT2 | AD-65836.1 | A-131991.1 | UCUGGAAGAGGUUUUUGUG | 956 | 471-489 |
| LECT2 | AD-65842.1 | A-131993.1 | UUUUUGUGUCAAAAUGUUC | 958 | 482-500 |
| LECT2 | AD-65848.1 | A-131995.1 | AUGUUCUACAUUAAGCCAA | 960 | 495-513 |
| LECT2 | AD-65854.1 | A-131997.1 | UAAGCCAAUUAAGUAUAAA | 962 | 506-524 |
| LECT2 | AD-65860.1 | A-131999.1 | AAGUAUAAAGGUCCUAUUA | 964 | 516-534 |
| LECT2 | AD-65866.1 | A-132001.1 | CCUAUUAAGAAGGGAGAAA | 966 | 528-546 |
| LECT2 | AD-65872.1 | A-132003.1 | AGGGAGAAAACUUGGAAC | 968 | 538-556 |
| LECT2 | AD-65878.1 | A-132005.1 | CUUGGAACUCUAUUGCCCU | 970 | 549-567 |
| LECT2 | AD-65884.1 | A-132007.1 | UUGCCCUUGCAGAAAGUUU | 972 | 561-579 |
| LECT2 | AD-65890.1 | A-132009.1 | AGAAAGUUUAUCCUGGCAU | 974 | 571-589 |
| LECT2 | AD-65896.1 | A-132011.1 | CCUGGCAUACAAUCGCAUG | 976 | 582-600 |
| LECT2 | AD-65902.1 | A-132013.1 | AUCGCAUGUGCACAUUGAA | 978 | 593-611 |
| LECT2 | AD-65907.1 | A-132015.1 | CAUUGAAAACUGUGACUCG | 980 | 605-623 |
| LECT2 | AD-65867.1 | A-132017.1 | GUGACUCGAGUGACCCUAC | 982 | 616-634 |
| LECT2 | AD-65873.1 | A-132019.1 | UGACCCUACUGCAUACCUG | 984 | 626-644 |
| LECT2 | AD-65879.1 | A-132021.1 | CAUACCUGUAAAUCGAAGG | 986 | 637-655 |
| LECT2 | AD-65891.1 | A-132025.1 | UGGUCAGAUCUUCAAAAUA | 988 | 660-678 |
| LECT2 | AD-65897.1 | A-132027.1 | CUUCAAAAUAAAAAGUCAU | 990 | 669-687 |
| LECT2 | AD-65903.1 | A-132029.1 | AAGUCAUCUUAAAAACCUG | 992 | 681-699 |
| LECT2 | AD-65908.1 | A-132031.1 | AAAACCUGGAUGCAUACCC | 994 | 692-710 |
| LECT2 | AD-65868.1 | A-132033.1 | GCAUACCCUUCUCUUCAAG | 996 | 703-721 |
| LECT2 | AD-65874.1 | A-132035.1 | CUUCAAGAAAUUUGUGUUC | 998 | 715-733 |
| LECT2 | AD-65880.1 | A-132037.1 | UUGUGUUCACAAAGGAAAA | 1000 | 726-744 |
| LECT2 | AD-65886.1 | A-132039.1 | AAGGAAAAAUGCAUGAAGG | 1002 | 737-755 |

TABLE 10-continued

Unmodified LECT2 siRNA Sequences

| Target | | | Sequence | SEQ ID NO | Position |
|---|---|---|---|---|---|
| LECT2 | AD-65892.1 | A-132041.1 | UGCAUGAAGGGAUGGAUAC | 1004 | 746-764 |
| LECT2 | AD-65898.1 | A-132043.1 | UGGAUACCCCAUUUUCCAU | 1006 | 758-776 |
| LECT2 | AD-65904.1 | A-132045.1 | UUUCCAUGACAUGAUUAUU | 1008 | 770-788 |
| LECT2 | AD-65909.1 | A-132047.1 | CAUGAUUAUUACACAUUGC | 1010 | 779-797 |
| LECT2 | AD-65869.1 | A-132049.1 | CACAUUGCAUGCCUGUAUC | 1012 | 790-808 |
| LECT2 | AD-65875.1 | A-132051.1 | CCUGUAUCAAAACAUCUCA | 1014 | 801-819 |
| LECT2 | AD-65881.1 | A-132053.1 | CAUCUCACGUACCUCAUAA | 1016 | 813-831 |
| LECT2 | AD-65887.1 | A-132055.1 | CCUCAUAAACAUAUACACC | 1018 | 824-842 |
| LECT2 | AD-65893.1 | A-132057.1 | AUACACCUAUGUACCCACA | 1020 | 836-854 |
| LECT2 | AD-65899.1 | A-132059.1 | GUACCCACAAAAAUUUUUU | 1022 | 846-864 |
| LECT2 | AD-65905.1 | A-132061.1 | UAAAAAAGGAAAUUUGAG | 1024 | 856-874 |
| LECT2 | AD-65910.1 | A-132063.1 | AAUUUGAGUUUAAAUAGAA | 1026 | 867-885 |
| LECT2 | AD-65870.1 | A-132065.1 | AUAGAAACAUGAUAAAUGC | 1028 | 880-898 |
| LECT2 | AD-65876.1 | A-132067.1 | GAUAAAUGCAAGAAAGAAA | 1030 | 890-908 |
| LECT2 | AD-65882.1 | A-132069.1 | GAAAGAAAACAUUUUGAUU | 1032 | 901-919 |
| LECT2 | AD-65894.1 | A-132073.1 | ACUCAUUGUCACUCUGAUG | 1034 | 923-941 |
| LECT2 | AD-65900.1 | A-132075.1 | CUCUGAUGUUCAUGUGAAC | 1036 | 934-952 |
| LECT2 | AD-65906.1 | A-132077.1 | CAUGUGAACUGGUUGCUUC | 1038 | 944-962 |
| LECT2 | AD-65911.1 | A-132079.1 | GUUGCUUCGGGCUCUUUGA | 1040 | 955-973 |
| LECT2 | AD-65871.1 | A-132081.1 | UCUUUGAUCUGUCACCUAU | 1042 | 967-985 |
| LECT2 | AD-65877.1 | A-132083.1 | CACCUAUGGAAUCUGAGUG | 1044 | 979-997 |
| LECT2 | AD-65883.1 | A-132085.1 | AAUCUGAGUGGUUUUAUUU | 1046 | 988-1006 |
| LECT2 | AD-65889.1 | A-132087.1 | UUUUUUAGAUUUCUCAGUC | 1048 | 999-1017 |
| LECT2 | AD-65895.1 | A-132089.1 | CUCAGUCCCAAAGAUCUAA | 1050 | 1011-1029 |
| LECT2 | AD-65901.1 | A-132091.1 | GAUCUAAGAUAAAUAAACA | 1052 | 1023-1041 |

| Target | Antisense Oligo Name | Antisense Sequence | SEQ ID NO | Position in NM_002302.2 |
|---|---|---|---|---|
| LECT2 | A-131908.1 | AAGUCAAGUUCUAAUAUUC | 873 | 11-29 |
| LECT2 | A-131910.1 | GGAUGGAGCAAGUCAAGUU | 875 | 20-38 |
| LECT2 | A-131912.1 | AAAAGUUUAAGAGGAUGG | 877 | 33-51 |
| LECT2 | A-131914.1 | GUGAGACACAAAAAGUUUA | 879 | 42-60 |
| LECT2 | A-131916.1 | CAUUUCUUUAGUGUGAGAC | 881 | 54-72 |
| LECT2 | A-131918.1 | CUGCAUCUCUCAUUUCUUU | 883 | 64-82 |
| LECT2 | A-131920.1 | UAGCCUUAGAAUUCUGCAU | 885 | 77-95 |
| LECT2 | A-131922.1 | CUAGCUAUUUAGCCUUAGA | 887 | 86-104 |
| LECT2 | A-131924.1 | AUGAAUACUUCCUAGCUAU | 889 | 97-115 |
| LECT2 | A-131926.1 | UAUUCAAGUUUGAAUGAAU | 891 | 110-128 |
| LECT2 | A-131928.1 | UCUUUGAAGAAUAUUCAAG | 893 | 121-139 |
| LECT2 | A-131930.1 | CCCCACACUCUCUUUGAAG | 895 | 131-149 |

TABLE 10-continued

| | | Unmodified LECT2 siRNA Sequences | | |
|---|---|---|---|---|
| LECT2 | A-131932.1 | AUUAGAGUUGCCCCCACAC | 897 | 142-160 |
| LECT2 | A-131934.1 | UCUUCCUCUGAUUAGAGUU | 899 | 152-170 |
| LECT2 | A-131936.1 | CUUCCUUUAGUUUCUUCCU | 901 | 164-182 |
| LECT2 | A-131938.1 | UCUGGUUUUACUUCCUUUA | 903 | 174-192 |
| LECT2 | A-131940.1 | GGUGGAAAACAUCUGGUUU | 905 | 185-203 |
| LECT2 | A-131942.1 | AAAGGAGGGCUUUGGUGGA | 907 | 198-216 |
| LECT2 | A-131944.1 | CAGACCAGCCAAAAGGAGG | 909 | 209-227 |
| LECT2 | A-131946.1 | GGUAGAAAUCAGACCAGCC | 911 | 218-236 |
| LECT2 | A-131948.1 | CCUGCCAGUGCGGUAGAAA | 913 | 229-247 |
| LECT2 | A-131950.1 | AUUAGCCCAUGGCCCUGCC | 915 | 242-260 |
| LECT2 | A-131952.1 | CCAGCACAUAUAUUAGCCC | 917 | 253-271 |
| LECT2 | A-131954.1 | GGAAGACUUGCCAGCACAU | 919 | 263-281 |
| LECT2 | A-131956.1 | GGAUCUCAUUGGAAGACUU | 921 | 273-291 |
| LECT2 | A-131958.1 | CGGUCACACGUCCGGAUCU | 923 | 286-304 |
| LECT2 | A-131960.1 | ACAGCCAUGGCGGUCACAC | 925 | 296-314 |
| LECT2 | A-131962.1 | GAGUACUGUCCACAGCCAU | 927 | 307-325 |
| LECT2 | A-131964.1 | CUUCUUUGAGCAGAGUACU | 929 | 319-337 |
| LECT2 | A-131966.1 | GAGGCCUCUGACUUCUUUG | 931 | 330-348 |
| LECT2 | A-131968.1 | CACCCUGGUGAGGCCUCUG | 933 | 339-357 |
| LECT2 | A-131970.1 | CAAGAUGUCCACACCCUGG | 935 | 350-368 |
| LECT2 | A-131972.1 | CCAGCAGAGCACAAGAUGU | 937 | 361-379 |
| LECT2 | A-131974.1 | UACACAGUAGAUCCAGCAG | 939 | 373-391 |
| LECT2 | A-131976.1 | GUGAAUGGUGCGUACACAG | 941 | 385-403 |
| LECT2 | A-131978.1 | CAAUCAUUCCAGUGAAUGG | 943 | 396-414 |
| LECT2 | A-131980.1 | CUCCUGGCCCACAAUCAUU | 945 | 407-425 |
| LECT2 | A-131982.1 | AUAAGGUUUCUCCUGGCCC | 947 | 416-434 |
| LECT2 | A-131984.1 | CAUUCUUGUUUUGAUAAGG | 949 | 429-447 |
| LECT2 | A-131986.1 | AUUAUUGAUAGCAUUCUUG | 951 | 440-458 |
| LECT2 | A-131988.1 | UUCGAACACCAUUAUUGAU | 953 | 450-468 |
| LECT2 | A-131990.1 | CUCUUCCAGAUAUUCGAAC | 955 | 462-480 |
| LECT2 | A-131992.1 | CACAAAAACCUCUUCCAGA | 957 | 471-489 |
| LECT2 | A-131994.1 | GAACAUUUUGACACAAAAA | 959 | 482-500 |
| LECT2 | A-131996.1 | UUGGCUUAAUGUAGAACAU | 961 | 495-513 |
| LECT2 | A-131998.1 | UUUAUACUUAAUUGGCUUA | 963 | 506-524 |
| LECT2 | A-132000.1 | UAAUAGGACCUUUAUACUU | 965 | 516-534 |
| LECT2 | A-132002.1 | UUUCUCCCUUCUUAAUAGG | 967 | 528-546 |
| LECT2 | A-132004.1 | GUUCCAAGUUUUUCUCCCU | 969 | 538-556 |
| LECT2 | A-132006.1 | AGGGCAAUAGAGUUCCAAG | 971 | 549-567 |
| LECT2 | A-132008.1 | AAACUUUCUGCAAGGGCAA | 973 | 561-579 |

TABLE 10-continued

| | | Unmodified LECT2 siRNA Sequences | | |
|---|---|---|---|---|
| LECT2 | A-132010.1 | AUGCCAGGAUAAACUUUCU | 975 | 571-589 |
| LECT2 | A-132012.1 | CAUGCGAUUGUAUGCCAGG | 977 | 582-600 |
| LECT2 | A-132014.1 | UUCAAUGUGCACAUGCGAU | 979 | 593-611 |
| LECT2 | A-132016.1 | CGAGUCACAGUUUUCAAUG | 981 | 605-623 |
| LECT2 | A-132018.1 | GUAGGGUCACUCGAGUCAC | 983 | 616-634 |
| LECT2 | A-132020.1 | CAGGUAUGCAGUAGGGUCA | 985 | 626-644 |
| LECT2 | A-132022.1 | CCUUCGAUUUACAGGUAUG | 987 | 637-655 |
| LECT2 | A-132026.1 | UAUUUUGAAGAUCUGACCA | 989 | 660-678 |
| LECT2 | A-132028.1 | AUGACUUUUUAUUUUGAAG | 991 | 669-687 |
| LECT2 | A-132030.1 | CAGGUUUUUAAGAUGACUU | 993 | 681-699 |
| LECT2 | A-132032.1 | GGGUAUGCAUCCAGGUUUU | 995 | 692-710 |
| LECT2 | A-132034.1 | CUUGAAGAGAAGGGUAUGC | 997 | 703-721 |
| LECT2 | A-132036.1 | GAACACAAAUUUCUUGAAG | 999 | 715-733 |
| LECT2 | A-132038.1 | UUUUCCUUUGUGAACACAA | 1001 | 726-744 |
| LECT2 | A-132040.1 | CCUUCAUGCAUUUUUCCUU | 1003 | 737-755 |
| LECT2 | A-132042.1 | GUAUCCAUCCCUUCAUGCA | 1005 | 746-764 |
| LECT2 | A-132044.1 | AUGGAAAAUGGGGUAUCCA | 1007 | 758-776 |
| LECT2 | A-132046.1 | AAUAAUCAUGUCAUGGAAA | 1009 | 770-788 |
| LECT2 | A-132048.1 | GCAAUGUGUAAUAAUCAUG | 1011 | 779-797 |
| LECT2 | A-132050.1 | GAUACAGGCAUGCAAUGUG | 1013 | 790-808 |
| LECT2 | A-132052.1 | UGAGAUGUUUUGAUACAGG | 1015 | 801-819 |
| LECT2 | A-132054.1 | UUAUGAGGUACGUGAGAUG | 1017 | 813-831 |
| LECT2 | A-132056.1 | GGUGUAUAUGUUUAUGAGG | 1019 | 824-842 |
| LECT2 | A-132058.1 | UGUGGGUACAUAGGUGUAU | 1021 | 836-854 |
| LECT2 | A-132060.1 | AAAAAAUUUUGUGGGUAC | 1023 | 846-864 |
| LECT2 | A-132062.1 | CUCAAAUUUCCUUUUUUUA | 1025 | 856-874 |
| LECT2 | A-132064.1 | UUCUAUUUAAACUCAAAUU | 1027 | 867-885 |
| LECT2 | A-132066.1 | GCAUUUAUCAUGUUUCUAU | 1029 | 880-898 |
| LECT2 | A-132068.1 | UUUCUUUCUUGCAUUUAUC | 1031 | 890-908 |
| LECT2 | A-132070.1 | AAUCAAAAUGUUUUCUUUC | 1033 | 901-919 |
| LECT2 | A-132074.1 | CAUCAGAGUGACAAUGAGU | 1035 | 923-941 |
| LECT2 | A-132076.1 | GUUCACAUGAACAUCAGAG | 1037 | 934-952 |
| LECT2 | A-132078.1 | GAAGCAACCAGUUCACAUG | 1039 | 944-962 |
| LECT2 | A-132080.1 | UCAAAGAGCCCGAAGCAAC | 1041 | 955-973 |
| LECT2 | A-132082.1 | AUAGGUGACAGAUCAAAGA | 1043 | 967-985 |
| LECT2 | A-132084.1 | CACUCAGAUUCCAUAGGUG | 1045 | 979-997 |
| LECT2 | A-132086.1 | AAAUAAAACCACUCAGAUU | 1047 | 988-1006 |
| LECT2 | A-132088.1 | GACUGAGAAAUCUAAAAAA | 1049 | 999-1017 |

TABLE 10-continued

Unmodified LECT2 siRNA Sequences

| | | | | |
|---|---|---|---|---|
| LECT2 | A-132090.1 | UUAGAUCUUUGGGACUGAG | 1051 | 1011-1029 |
| LECT2 | A-132092.1 | UGUUUAUUUAUCUUAGAUC | 1053 | 1023-1041 |

Results

The results of single dose screen in primary monkey hepatocytes using modified LECT2 siRNA sequences are shown in Table 11. The single dose experiments were performed at 10 nM final duplex concentration and the data are expressed as percent message remaining relative to AD-1955 non-targeting control.

TABLE 11

Lect2 Single Dose Screen in Primary Monkey Hepatocytes

| Duplex Name | 10 nM avg | 10 nM stdev |
|---|---|---|
| AD-65819.1 | 11.7 | 8.5 |
| AD-65825.1 | 50.7 | 28.0 |
| AD-65831.1 | 75.3 | 49.5 |
| AD-65837.1 | 75.5 | 32.7 |
| AD-65843.1 | 5.5 | 3.0 |
| AD-65849.1 | 104.5 | 64.9 |
| AD-65855.1 | 114.1 | 36.7 |
| AD-65861.1 | 81.5 | 49.6 |
| AD-65820.1 | 3.3 | 1.4 |
| AD-65826.1 | 43.6 | 18.4 |
| AD-65832.1 | 6.5 | 2.2 |
| AD-65838.1 | 61.8 | 11.9 |
| AD-65844.1 | 4.2 | 2.1 |
| AD-65850.1 | 85.8 | 24.0 |
| AD-65856.1 | 105.4 | 24.0 |
| AD-65862.1 | 50.4 | 15.5 |
| AD-65821.1 | 56.1 | 32.5 |
| AD-65827.1 | 37.8 | 5.7 |
| AD-65833.1 | 4.7 | 2.6 |
| AD-65839.1 | 5.2 | 1.6 |
| AD-65845.1 | 65.1 | 19.1 |
| AD-65851.1 | 46.1 | 5.4 |
| AD-65857.1 | 35.0 | 5.4 |
| AD-65863.1 | 58.0 | 14.4 |
| AD-65822.1 | 82.7 | 10.4 |
| AD-65828.1 | 95.9 | 29.0 |
| AD-65834.1 | 7.9 | 2.9 |
| AD-65840.1 | 98.3 | 39.1 |
| AD-65846.1 | 33.8 | 16.1 |
| AD-65852.1 | 32.8 | 4.4 |
| AD-65858.1 | 73.4 | 29.3 |
| AD-65864.1 | 7.0 | 3.0 |
| AD-65823.1 | 54.5 | 18.8 |
| AD-65829.1 | 17.1 | 14.8 |
| AD-65835.1 | 100.4 | 31.8 |
| AD-65841.1 | 11.1 | 10.4 |
| AD-65847.1 | 165.1 | 39.2 |
| AD-65853.1 | 1.7 | 0.3 |
| AD-65859.1 | 39.9 | 6.3 |
| AD-65865.1 | 76.5 | 17.0 |
| AD-65824.1 | 66.0 | 10.5 |
| AD-65830.1 | 106.0 | 16.1 |
| AD-65836.1 | 67.5 | 19.2 |
| AD-65842.1 | 147.3 | 38.9 |
| AD-65848.1 | 20.1 | 4.5 |
| AD-65854.1 | 40.4 | 12.1 |
| AD-65860.1 | 62.8 | 19.0 |
| AD-65866.1 | 49.8 | 8.9 |
| AD-65872.1 | 45.6 | 15.8 |
| AD-65878.1 | 11.4 | 5.6 |
| AD-65884.1 | 6.1 | 2.5 |
| AD-65890.1 | 47.1 | 23.0 |
| AD-65896.1 | 108.3 | 58.2 |
| AD-65902.1 | 9.8 | 3.3 |
| AD-65907.1 | 19.6 | 4.7 |
| AD-65867.1 | 39.9 | 8.8 |
| AD-65873.1 | 14.8 | 5.1 |
| AD-65879.1 | 113.2 | 7.1 |
| AD-65891.1 | 2.5 | 1.5 |
| AD-65897.1 | 15.0 | 6.7 |
| AD-65903.1 | 44.8 | 14.0 |
| AD-65908.1 | 77.1 | 23.6 |
| AD-65868.1 | 32.7 | 3.9 |
| AD-65874.1 | 119.4 | 35.4 |
| AD-65880.1 | 117.6 | 30.6 |
| AD-65886.1 | 127.8 | 45.3 |
| AD-65892.1 | 80.0 | 20.6 |
| AD-65898.1 | 75.1 | 29.3 |
| AD-65904.1 | 123.8 | 31.5 |
| AD-65909.1 | 97.9 | 10.0 |
| AD-65869.1 | 34.3 | 8.4 |
| AD-65875.1 | 76.5 | 12.1 |
| AD-65881.1 | 35.7 | 6.4 |
| AD-65887.1 | 88.8 | 32.6 |
| AD-65893.1 | 141.7 | 5.5 |
| AD-65899.1 | 149.8 | 29.1 |
| AD-65905.1 | 167.5 | 36.8 |
| AD-65910.1 | 58.5 | 20.7 |
| AD-65870.1 | 92.3 | 33.3 |
| AD-65876.1 | 86.8 | 22.2 |
| AD-65882.1 | 65.5 | 10.6 |
| AD-65894.1 | 69.4 | 20.5 |
| AD-65900.1 | 125.0 | 57.8 |
| AD-65906.1 | 153.4 | 54.0 |
| AD-65911.1 | 114.4 | 24.2 |
| AD-65871.1 | 59.6 | 26.4 |
| AD-65877.1 | 58.1 | 18.5 |
| AD-65883.1 | 60.3 | 16.6 |
| AD-65889.1 | 74.1 | 25.1 |
| AD-65895.1 | 94.0 | 11.8 |
| AD-65901.1 | 92.4 | 6.2 |
| AD-1955 | 100.1 | 24.7 |

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A double-stranded ribonucleic acid (dsRNA) for inhibiting expression of LECT2, wherein said dsRNA comprises a sense strand and an antisense strand, each of which is 19-30 nucleotides in length, wherein the antisense strand comprises a region of complementarity to a LECT2 RNA transcript and is complementary to at least nucleotides 668-686 of SEQ ID NO: 1, and wherein the antisense strand comprises at least 19 contiguous nucleotides from SEQ ID NO: 682.

2. The dsRNA of claim 1, wherein said dsRNA comprises at least one modified nucleotide.

3. The dsRNA of claim of claim 1, wherein said dsRNA comprises a duplex region of 15-30, 17-23, 19-21, or 21-23 nucleotide pairs in length.

4. The dsRNA of claim 1, wherein the region of complementarity is 19-24 nucleotides in length.

5. The dsRNA of claim 1, wherein the region of complementarity is 19, 20, or 21 nucleotides in length.

6. The dsRNA of claim 1, wherein at least one strand comprises a 3' overhang of at least 1 or 2 nucleotides.

7. The dsRNA of claim 2, wherein the at least one modified nucleotide is chosen from a 2'-O-methyl modified nucleotide, a 2'-fluoro modified nucleotide, or both.

8. The dsRNA of claim 7, wherein the dsRNA comprises one or more phosphorothioate linkages.

9. The dsRNA of claim 2, wherein the dsRNA comprises at least 20 modified nucleotides.

10. The dsRNA of claim 1, wherein the sense strand is conjugated to at least one ligand.

11. The dsRNA of claim 10, wherein the ligand is attached to the 3' end of the sense strand.

12. The dsRNA of claim 10, wherein the ligand is a GalNAc ligand.

13. The dsRNA of claim 10, wherein the ligand is

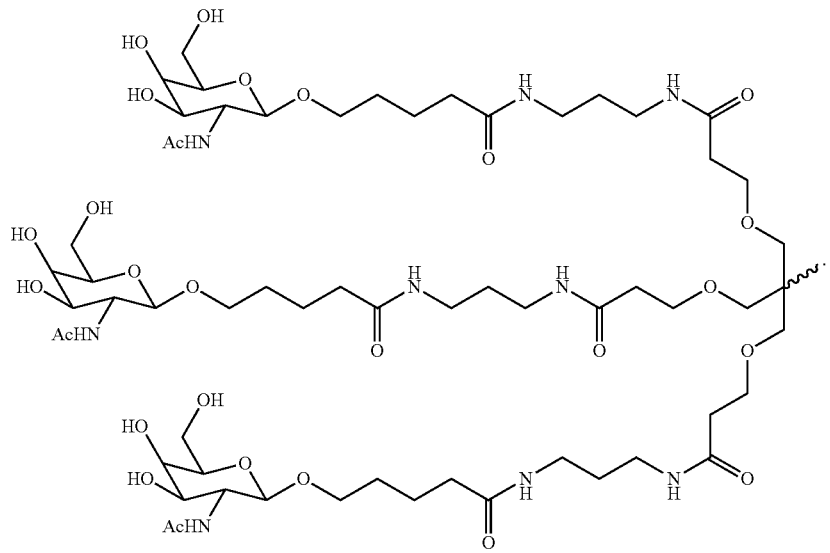 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

14. The dsRNA of claim 10, wherein the ligand is attached via a linker, and the ligand and linker are as shown in Formula XXIV:

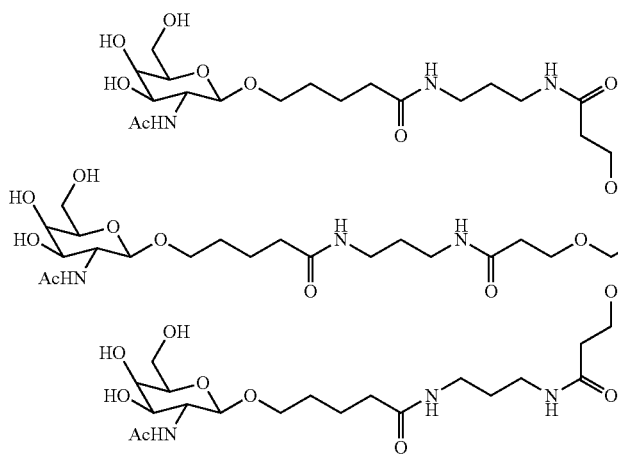
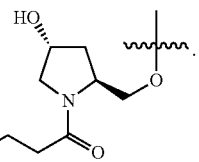

15. The dsRNA of claim 1, wherein the region of complementarity consists of an antisense sequence of SEQ ID NO: 682.

16. The dsRNA of claim 1, wherein the dsRNA comprises a sense strand consisting of a sense sequence of SEQ ID NO: 681 and an antisense strand consisting of an antisense sequence of SEQ ID NO: 682.

17. A cell containing the dsRNA of claim 1.

18. A pharmaceutical composition for inhibiting expression of a LECT2 gene, the composition comprising the dsRNA of claim 1.

19. The pharmaceutical composition of claim 18, wherein said composition comprises a lipid formulation.

20. The pharmaceutical composition of claim 19, wherein the lipid formulation is a LNP11 formulation.

21. A method of inhibiting LECT2 expression in a cell, the method comprising:
 (a) introducing into the cell the dsRNA of claim 1, and
 (b) maintaining the cell of step (a) for a time sufficient to obtain degradation of the mRNA transcript of a LECT2 gene, thereby inhibiting expression of the LECT2 gene in the cell.

22. The method of claim 21, wherein the cell is treated ex vivo, in vitro, or in vivo.

23. The method of claim 21, wherein the cell is a liver cell or a hepatocyte.

24. The method of claim 21, wherein the expression of LECT2 is inhibited by at least 30%.

25. A method of treating a LECT2 amyloidosis comprising administering to a subject in need of such treatment the dsRNA of claim 1.

26. The method of claim 25, wherein the dosing regimen is weekly, biweekly, or monthly.

27. The method of claim 25, wherein the dsRNA is administered at a dose of 0.05-50, 0.01-5, 0.1-0.5, or 1-10 mg/kg body weight of the subject.

28. The method of claim 27, wherein the dsRNA is conjugated to a GalNAc ligand.

29. The method of claim 25, wherein the antisense strand comprises an antisense sequence of SEQ ID NO: 682.

30. The dsRNA of claim 1, wherein the dsRNA comprises a sense strand consisting of the sequence and all of the modifications of SEQ ID NO: 587 and an antisense strand consisting of the sequence and all of the modifications of SEQ ID NO: 588.

31. The dsRNA of claim 1, wherein the antisense strand comprises an antisense sequence chosen from SEQ ID NOs: 682, 678, 680, or 684.

32. The dsRNA of claim 1, wherein the region of complementarity consists of an antisense sequence chosen from SEQ ID NOs: 682, 678, 680, or 684.

33. The dsRNA of claim 1, wherein the dsRNA comprises a sense strand consisting of a sense sequence chosen from SEQ ID NOs: 681, 677, 679, or 683, and an antisense strand consisting of an antisense sequence chosen from SEQ ID NOs: 682, 678, 680, or 684.

34. The dsRNA of claim 1, wherein the antisense strand comprises the sequence and all of the modifications of an antisense sequence chosen from SEQ ID NOs: 588, 584, 586, or 590.

35. The dsRNA of claim 1, wherein the region of complementarity consists of the sequence and all of the modifications of an antisense sequence chosen from SEQ ID NOs: 588, 584, 586, or 590.

36. The dsRNA of claim 1, wherein the dsRNA comprises a sense strand consisting of the sequence and all of the modifications of an antisense sequence chosen from SEQ ID NOs: 587, 583, 585, or 589 529, and an antisense strand consisting of the sequence and all of the modifications of an antisense sequence chosen from SEQ ID NOs: 588, 584, 586, or 590.

37. A dsRNA for inhibiting expression of LECT2, wherein said dsRNA comprises a sense strand and an antisense strand, each of which is 20-30 nucleotides in length, wherein the antisense strand comprises a region of complementarity to a LECT2 RNA transcript, wherein the antisense strand comprises at least 20 contiguous nucleotides from SEQ ID NOs: 682, 678, 680, or 684.

38. The dsRNA of claim 37, wherein the dsRNA comprises a sense strand consisting of a sense sequence chosen from SEQ ID NOs: 681, 677, 679, or 683.

39. The dsRNA of claim 37, wherein said dsRNA comprises at least one modified nucleotide.

40. The dsRNA of claim 37, wherein the antisense strand comprises the sequence and all of the modifications of an antisense sequence chosen from SEQ ID NOs: 588, 584, 586, or 590.

41. The dsRNA of claim 37, wherein the dsRNA comprises a sense strand consisting of the sequence and all of the modifications of an antisense sequence chosen from SEQ ID NOs: 587, 583, 585, or 589, and an antisense strand consisting of the sequence and all of the modifications of an antisense sequence chosen from SEQ ID NOs: 588, 584, 586, or 590.

42. The dsRNA of claim 37, wherein the sense strand is conjugated to at least one ligand.

43. A dsRNA for inhibiting expression of LECT2, wherein said dsRNA comprises a sense strand and an antisense strand, each of which is 20-30 nucleotides in length, wherein the antisense strand comprises a region of complementarity to a LECT2 RNA transcript, wherein the antisense strand comprises at least 20 contiguous nucleotides of one of the antisense sequences chosen from SEQ ID NOs: 660, 650, 654, 636, 676, or 624.

44. The dsRNA of claim 43, wherein said dsRNA comprises at least one modified nucleotide.

45. The dsRNA of claim 43, wherein the region of complementarity is 19-24 nucleotides in length.

46. The dsRNA of claim 43, wherein at least one strand comprises a 3' overhang of at least 1 or 2 nucleotides.

47. The dsRNA of claim 44, wherein the at least one modified nucleotide is chosen from a 2'-O-methyl modified nucleotide, a 2'-fluoro modified nucleotide, or both.

48. The dsRNA of claim 47, wherein the dsRNA comprises one or more phosphorothioate linkages.

49. The dsRNA of claim 43, wherein the sense strand is conjugated to at least one ligand.

50. The dsRNA of claim 49, wherein the ligand is attached to the 3' end of the sense strand.

51. The dsRNA of claim 49, wherein the ligand is a GalNAc ligand.

52. The dsRNA of claim 49, wherein the ligand is

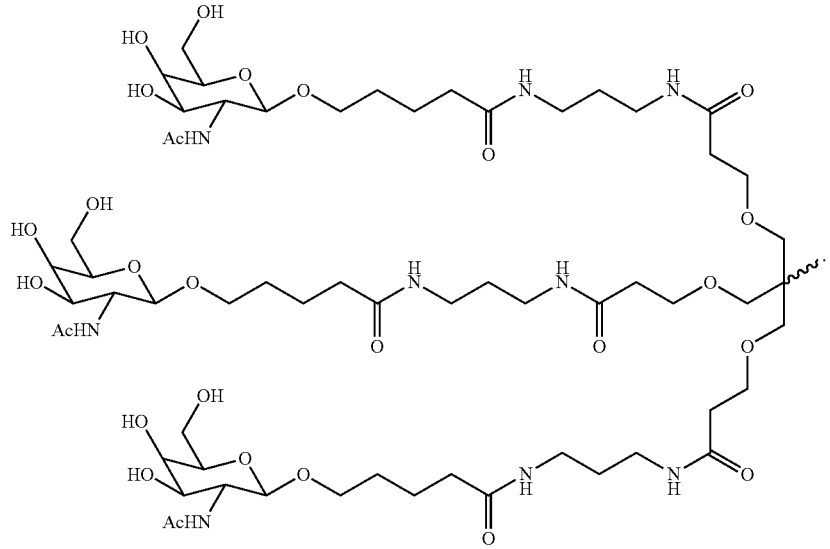 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

53. The dsRNA of claim 49, wherein the ligand is attached via a linker, and the ligand and linker are as shown in Formula XXIV:

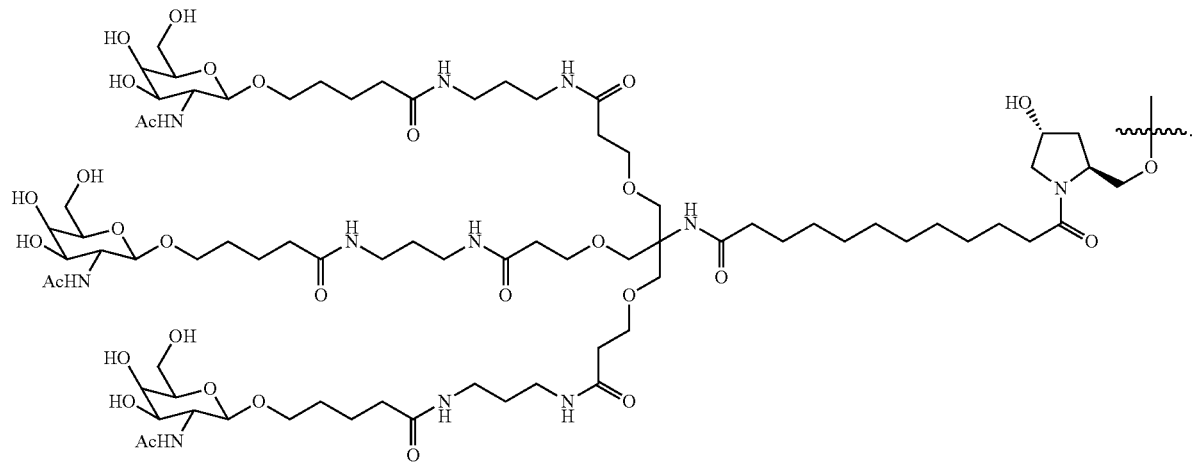 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

54. The dsRNA of claim 43, wherein the antisense strand comprises an antisense sequence chosen from SEQ ID NOs: 660, 650, 654, 636, 676, or 624.

55. The dsRNA of claim 43, wherein the region of complementarity consists of an antisense sequence chosen from SEQ ID NOs: 660, 650, 654, 636, 676, or 624.

56. The dsRNA of claim 43, wherein the dsRNA comprises a sense strand consisting of a sense sequence chosen from SEQ ID NOs: 659, 649, 653, 635, 675, or 623, and an antisense strand consisting of an antisense sequence chosen from SEQ ID NOs: 660, 650, 654, 636, 676, or 624.

57. The dsRNA of claim 43, wherein the antisense strand comprises the sequence and all of the modifications of an antisense sequence chosen from SEQ ID NOs: 566, 556, 560, 542, 582, or 530.

58. The dsRNA of claim 43, wherein the region of complementarity consists of the sequence and all of the modifications of an antisense sequence chosen from SEQ ID NOs: 566, 556, 560, 542, 582, or 530.

59. The dsRNA of claim 43, wherein the dsRNA comprises a sense strand consisting of the sequence and all of the modifications of an antisense sequence chosen from SEQ ID NOs: 565, 555, 559, 541, 581, or 529, and an antisense strand consisting of the sequence and all of the modifications of an antisense sequence chosen from SEQ ID NOs: 566, 556, 560, 542, 582, or 530.

60. A cell containing the dsRNA of claim 37.

61. A pharmaceutical composition for inhibiting expression of a LECT2 gene, the composition comprising the dsRNA of claim 37.

62. The pharmaceutical composition of claim 61, wherein said composition comprises a lipid formulation.

63. A method of inhibiting LECT2 expression in a cell, the method comprising:
   (a) introducing into the cell the dsRNA of claim 37, and
   (b) maintaining the cell of step (a) for a time sufficient to obtain degradation of the mRNA transcript of a LECT2 gene, thereby inhibiting expression of the LECT2 gene in the cell.

64. A method of treating a LECT2 amyloidosis comprising administering to a subject in need of such treatment the dsRNA of claim 37.

65. The method of claim 64, wherein the dsRNA is conjugated to a GalNAc ligand.

66. A cell containing the dsRNA of claim 43.

67. A pharmaceutical composition for inhibiting expression of a LECT2 gene, the composition comprising the dsRNA of claim 43.

68. The pharmaceutical composition of claim 67, wherein said composition comprises a lipid formulation.

69. A method of inhibiting LECT2 expression in a cell, the method comprising:
   (a) introducing into the cell the dsRNA of claim 43, and
   (b) maintaining the cell of step (a) for a time sufficient to obtain degradation of the mRNA transcript of a LECT2 gene, thereby inhibiting expression of the LECT2 gene in the cell.

70. A method of treating a LECT2 amyloidosis comprising administering to a subject in need of such treatment the dsRNA of claim 43.

71. The method of claim 70, wherein the dsRNA is conjugated to a GalNAc ligand.

* * * * *